(12) United States Patent
Simon et al.

(10) Patent No.: US 9,695,214 B2
(45) Date of Patent: *Jul. 4, 2017

(54) SOLID PHASE PEPTIDE SYNTHESIS PROCESSES AND ASSOCIATED SYSTEMS

(71) Applicant: Massachusetts Institute of Technology, Cambridge, MA (US)

(72) Inventors: Mark David Simon, Gainesville, FL (US); Bradley L. Pentelute, Cambridge, MA (US); Andrea Adamo, Cambridge, MA (US); Patrick Louis Heider, Midland, MI (US); Klavs F. Jensen, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/776,870

(22) PCT Filed: Feb. 24, 2014

(86) PCT No.: PCT/US2014/017970
§ 371 (c)(1),
(2) Date: Sep. 15, 2015

(87) PCT Pub. No.: WO2014/149387
PCT Pub. Date: Sep. 25, 2014

(65) Prior Publication Data
US 2016/0031931 A1    Feb. 4, 2016

Related U.S. Application Data

(63) Continuation-in-part of application No. 13/833,745, filed on Mar. 15, 2013, now Pat. No. 9,169,287.

(51) Int. Cl.
| | | |
|---|---|---|
| A61K 38/00 | (2006.01) | |
| C07K 5/00 | (2006.01) | |
| C07K 7/00 | (2006.01) | |
| C07K 16/00 | (2006.01) | |
| C07K 17/00 | (2006.01) | |
| C07K 1/04 | (2006.01) | |
| C07K 1/06 | (2006.01) | |
| C07K 1/08 | (2006.01) | |

(52) U.S. Cl.
CPC ............ *C07K 1/042* (2013.01); *C07K 1/045* (2013.01); *C07K 1/061* (2013.01); *C07K 1/08* (2013.01)

(58) Field of Classification Search
CPC .......... A61K 38/00; C07K 2/00; C07K 16/00
See application file for complete search history.

(56) References Cited

U.S. PATENT DOCUMENTS

| | | | |
|---|---|---|---|
| 4,192,798 A | 3/1980 | Verlander et al. | |
| 4,746,490 A | 5/1988 | Saneii | |
| 4,816,513 A | 3/1989 | Bridgham et al. | |
| 5,807,525 A | 9/1998 | Allen et al. | |
| 6,028,172 A | 2/2000 | Stepaniuk et al. | |
| 7,348,404 B2 | 3/2008 | Holm et al. | |
| 7,902,488 B2 | 3/2011 | Collins et al. | |
| 8,535,947 B2 | 9/2013 | Menakuru et al. | |
| 9,169,287 B2 | 10/2015 | Simon et al. | |
| 2014/0275481 A1 | 9/2014 | Simon et al. | |
| 2016/0102118 A1 | 4/2016 | Simon et al. | |

FOREIGN PATENT DOCUMENTS

| | | |
|---|---|---|
| EP | 1923396 A2 | 5/2008 |
| WO | WO 82/03077 A1 | 9/1982 |
| WO | WO 98/34633 A1 | 8/1998 |

OTHER PUBLICATIONS

Bacsa et al., J. Pept. Sci. 2006; 12: 633-638.*
Synthesis of Crosslinked Polymers, chapter 4, Results and Discussion, Jun. 18, 2010, available online at: http://shodhganga.inflibnet.ac.in/bitstream/10603/146/11/11_chapter4.pdf.*
[No Author Listed], CS Bio Specifications for CS336X. Last Accessed Jun. 20, 2016. http://www.csbio.com/peptide-synthesizers/cs-336x/.
[No Author Listed], We Have the Art of Peptide Synthesis Down to a Science. 2010. CEM Corporation. Complete Peptide Brochure. 9 pages.
Goodman et al., Synthesis of Peptides and Peptidomimetics. New York: Thieme Stuttgart. 2004; vol. E22a; Section 2.1 Amino Group. p. 65.
Goodman et al., Synthesis of Peptides and Peptidomimetics. New York: Thieme Stuttgart. 2004; vol. E22b; Section 5.3 Examples of Protein Synthesis on Solid Support. p. 65.
Goodman et al., Synthesis of Peptides and Peptidomimetics. New York: Thieme Stuttgart. 2004; vol. E22c; Section 9.2 Synthesis of Peptides Containing Proline Analogues. p. 65.
Krchnak et al., Continuous-flow solid-phase peptide synthesis. Tetrahedron Letters. 1987;28(38):4469-4472.
Mong et al., Rapid total synthesis of DARPin pE59 and barnase. Chembiochem. Mar. 21, 2014;15(5):721-33. doi: 10.1002/cbic.201300797. Epub Mar. 11, 2014.
Quibell et al., Preparation and purification of beta-Amyloid (1-43) via soluble, amide backbone protected intermediates. J Org Chem. Mar. 1994;59(7):1745-50.
Reid et al., Automated solid-phase peptide synthesis: use of 2-(1H-benzotriazol-1-yl)-1,1,3,3-tetramethyluronium tetrafluoroborate for coupling of tert-butyloxycarbonyl amino acids. Anal Biochem. Feb. 1, 1992;200(2):301-9.

(Continued)

*Primary Examiner* — Hasan Ahmed
*Assistant Examiner* — Kaipeen Yang
(74) *Attorney, Agent, or Firm* — Wolf, Greenfield & Sacks, P.C.

(57) ABSTRACT

Systems and processes for performing solid phase peptide synthesis are generally described. Solid phase peptide synthesis is a known process in which amino acid residues are added to peptides that have been immobilized on a solid support. In certain embodiments, the inventive systems and methods can be used to perform solid phase peptide synthesis quickly while maintaining high yields. Certain embodiments relate to processes and systems that may be used to heat, transport, and/or mix reagents in ways that reduce the amount of time required to perform solid phase peptide synthesis.

13 Claims, 33 Drawing Sheets

(56) References Cited

OTHER PUBLICATIONS

Simon et al., Rapid flow-based peptide synthesis. Chembiochem. Mar. 21, 2014;15(5):713-20. doi: 10.1002/cbic.201300796. Epub Mar. 11, 2014.
Invitation to Pay Additional Fees mailed Jun. 17, 2014 for PCT/US2014/017970.
International Search Report and Written Opinion for PCT/US2014/017970 mailed Sep. 22, 2014.
International Preliminary Report on Patentability for PCT/US2014/017970 mailed Sep. 24, 2015.
[No Author Listed] Apogee: Totally automated single peptide synthesizer. Advanced Automated Peptide Protein Technologies. Product Description. 2006. Louisville, KY. 4 pages.
[No Author Listed] Applied Biosystems User Bulletin No. 35: Model 431A Peptide Synthesizer. Nov. 1993. 26 pages. Updated Jul. 2002.
[No Author Listed] Bachem: The Bachem Practice of SPPS. Edition 2005. 84 pages.
[No Author Listed] Endeavor 90: Tabletop peptide synthesizer. Advanced Automated Peptide Protein Technologies. Product Description. 2006. Louisville, KY. 4 pages.
[No Author Listed] Focus XC: Automated peptide synthesizer. Advanced Automated Peptide Protein Technologies. Product Description. 2006. Louisville, KY. 4 pages.
[No Author Listed] Liberty 1: Advantages. CEM Corporation. 2011. Last accessed online at <http://www.cem.com/liberty-1-advantages.html> on May 9, 2013.
[No Author Listed] Liberty Blue. Microwave Peptide Synthesizer: peptide synthesis made fast and efficient. CEM Sales Literature LibBlue B105. 9 pages. accessible via: www.brs.be/pdf/525_broch_libblue_b105.pdf; dated Feb. 18, 2010.
[No Author Listed] Liberty. Microwave Peptide Synthesis. CEM Sales Literature Liberty, accessible via: www.cem.hu/pdf/liberty_eng.pdf; dated Mar. 6, 2005. 3 pages.
[No Author Listed] Liberty: Advantages. CEM Corporation. 2011. Last accessed online at <http://www.cem.com/liberty-advantages.html> on May 9, 2013.
[No Author Listed] Liberty: Liberty Overview. CEM Corporation. 2011. Last accessed online at <http://www.cem.com/liberty.html> on May 9, 2013.
[No Author Listed] PL-Wang Resin, Sales Literature, accessible via: www.cypress-international.com/imagepolymerlabs/wang.pdf; dated Apr. 27, 2003. 3 pages.

[No Author Listed] Pseudoproline Dipeptides, Corden Pharm Switzerland, Sales Literature, 2011. 4 pages.
Bacsa et al., Rapid solid-phase synthesis of a calmodulin-binding peptide using controlled microwave irradiation. Nature Protocols. 2007; 2(9):2222-2227.
Collins et al., High-efficiency solid phase peptide synthesis (HE-SPPS). Organic Letters. Jan. 23, 2014; 16:940-943.
Collins et al., Microwave energy: a versatile tool for the biosciences. Org Biomol Chem. 2007; 5:1141-1150.
Dryland et al., Peptide synthesis. Part 8. A system for solid-phase synthesis under low pressure continuous flow conditions. J Chem Soc, Perkin Trans 1. Jan. 1, 1986:125-37.
Fuentes et al., Fast conventional synthesis of $^{65\text{-}74}$ACP on the Symphony® and Prelude™ Protein Technologies, Inc. Tuscon, AZ. 1 page. 2006.
Hood et al., Fast conventional Fmoc solid-phase peptide synthesis with HCTU. J Pept Sci. Jan. 2008;14(1):97-101. Published online Sep. 24, 2007 in Wiley InterScience.
Lukas et al., Solid-phase peptide synthesis under continuous-flow conditions. Proc Natl Acad Sci U S A. May 1981;78(5):2791-5.
Meldal et al., PEGA: A flow stable polyethylene glycol dimethyl acrylamide copolymer for solid phase synthesis. Tetrahedron Letters. May 19, 1992;33(21):3077-80.
Miranda et al., Accelerated chemical synthesis of peptides and small proteins. Proc Natl Acad Sci U S A. Feb. 16, 1999;96(4):1181-6.
Pedersen et al., Microwave heating in solid-phase peptide synthesis. Chem Soc Rev. 2012;41:1826-44. Published online Oct. 20, 2011 on http://pubs.rsc.org.
Schnölzer et al., In situ neutralization in boc-chemistry solid phase peptide synthesis. International Journal of Peptide Research and Therapeutics. 1992;40:180-193. Published online Jun. 2007.
International Search Report and Written Opinion for PCT/US2016/052179 mailed Dec. 2, 2016.
Dang et al., Enhanced Solvation of Peptides Attached to "Solid-Phase" Resins: Straightforward Syntheses of the Elastin Sequence Pro-Gly-Val-Gly-Val-Pro-Gly-Val-Gly-Val. Org Lett. Jul. 17, 2015;17(14):3521-3. doi: 10.1021/acs.orglett.5b01632. Epub Jun. 25, 2015.
Gude et al., An accurate method for the quantitation of Fmoc-derivatized solid phase supports. Letters in Peptide Science; 2002; 9(4): 203-206.
Quade, Solid Phase Peptide Synthesis, Strategies and Resins, modified on May 28, 2006, available online at: http://wwwoc.chemie.uni-regensburg.de/OCP/ch/chv/oc22/script/006.pdf.

\* cited by examiner

PnIA(A10L) Conotoxin GCCSLPPCALNNPDYC-CONH$_2$ $[M+2H]^{2+}$ 834.83

$[M+H]^{+}$ 1668.66

Obs. 1667.66 Da
Calc. 1667.65 Da

*FIG. 5A*

HIV-1 PR (81-99) PVNIIGRNLLTQIGCTLNF-CONH$_2$ $[M+3H]^{3+}$ 696.06

$[M+2H]^{2+}$ 1043.59

Obs. 2085.17 Da
Calc. 2085.15 Da

*FIG. 5B*

SEQUENCE LISTING

```
<160> NUMBER OF SEQ ID NOS: 48

<210> SEQ ID NO 1
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with Fmoc

<400> SEQUENCE: 1

Ala Leu Phe Ala Leu Phe Ala
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 2

Leu Tyr Arg Ala Gly
1               5

<210> SEQ ID NO 3
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 3

Val Gln Ala Ala Ile Asp Tyr Ile Asn Gly
1               5                   10

<210> SEQ ID NO 4
<211> LENGTH: 16
<212> TYPE: PRT
```

```
<213> ORGANISM: Artificial Sequence
<220> FEATURE:
<223> OTHER INFORMATION: Synthetic Polypeptide

<400> SEQUENCE: 4

Gly Cys Cys Ser Leu Pro Pro Cys Ala Leu Asn Asn Pro Asp Tyr Cys
1               5                   10                  15

<210> SEQ ID NO 5
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 5

Pro Val Asn Ile Ile Gly Arg Asn Leu Leu Thr Gln Ile Gly Cys Thr
1               5                   10                  15

Leu Asn Phe

<210> SEQ ID NO 6
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 6

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg
            20                  25

<210> SEQ ID NO 7
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with Thz

<400> SEQUENCE: 7

Ala Phe Ile Gln Ser Leu Lys Asp Asp Pro Ser
1               5                   10

<210> SEQ ID NO 8
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 8

Cys Ser Ala Asn Leu Leu Ala Glu Ala Lys Lys Leu Asn Asp Ala Gln
1               5                   10                  15

Ala Pro Lys

<210> SEQ ID NO 9
<211> LENGTH: 27
<212> TYPE: PRT
<213> ORGANISM: Artificial Sequence
<220> FEATURE:
<223> OTHER INFORMATION: Synthetic Polypeptide
```

```
<220> FEATURE:
<221> NAME/KEY: MISC_FEATURE
<222> LOCATION: (1)..(1)
<223> OTHER INFORMATION: Modified with Fmoc

<400> SEQUENCE: 9

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg
            20                  25

<210> SEQ ID NO 10
<211> LENGTH: 33
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with Boc
<220> FEATURE:
<221> NAME/KEY: misc_feature
<222> LOCATION: (33)..(33)
<223> OTHER INFORMATION: Xaa can be any naturally occurring amino acid

<400> SEQUENCE: 10

Gly Gly Gly Gly Gly Val Asp Asn Lys Phe Asn Lys Glu Gln Gln Asn
1               5                   10                  15

Ala Phe Tyr Glu Ile Leu His Leu Pro Asn Leu Asn Glu Glu Gln Arg
            20                  25                  30

Xaa

<210> SEQ ID NO 11
<211> LENGTH: 11
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with Fmoc and Thz

<400> SEQUENCE: 11

Ala Phe Ile Gln Ser Leu Lys Asp Asp Pro Ser
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with Boc and Thz
<220> FEATURE:
<221> NAME/KEY: misc_feature
<222> LOCATION: (12)..(12)
<223> OTHER INFORMATION: Xaa can be any naturally occurring amino acid

<400> SEQUENCE: 12

Ala Phe Ile Gln Ser Leu Lys Asp Asp Pro Ser Xaa
1               5                   10

<210> SEQ ID NO 13
```

```
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with Fmoc

<400> SEQUENCE: 13

Cys Ser Ala Asn Leu Leu Ala Glu Ala Lys Lys Leu Asn Asp Ala Gln
1               5                   10                  15

Ala Pro Lys

<210> SEQ ID NO 14
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified with Boc

<400> SEQUENCE: 14

Cys Ser Ala Asn Leu Leu Ala Glu Ala Lys Lys Leu Asn Asp Ala Gln
1               5                   10                  15

Ala Pro Lys

<210> SEQ ID NO 15
<211> LENGTH: 39
<212> TYPE: PRT
<213> ORGANISM: Artificial Sequence
<220> FEATURE:
<223> OTHER INFORMATION: Synthetic Polypeptide

<400> SEQUENCE: 15

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Cys Ala Phe Ile Gln
                20                  25                  30

Ser Leu Lys Asp Asp Pro Ser
        35

<210> SEQ ID NO 16
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 16

Ala Gly Gln Gly Gly Tyr Gly Gly Leu Gly Ser Gln Gly Thr Ser Gly
1               5                   10                  15

Arg Gly Gly Leu Gly Gly Gln Gly
            20

<210> SEQ ID NO 17
<211> LENGTH: 11
<212> TYPE: PRT
<213> ORGANISM: Artificial Sequence
<220> FEATURE:
<223> OTHER INFORMATION: Synthetic Polypeptide
```

```
<400> SEQUENCE: 17

Gly Gly Gly Gly Gly Ala Arg Leu Leu Arg Leu
1               5                   10

<210> SEQ ID NO 18
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (6)..(6)
<223> OTHER INFORMATION: Xaa is bAla
<220> FEATURE:
<221> NAME/KEY: misc_feature
<222> LOCATION: (15)..(15)
<223> OTHER INFORMATION: Xaa is bAla
<220> FEATURE:
<221> NAME/KEY: misc_feature
<222> LOCATION: (18)..(18)
<223> OTHER INFORMATION: Xaa is bAla
<220> FEATURE:
<221> NAME/KEY: MISC_FEATURE
<222> LOCATION: (19)..(19)
<223> OTHER INFORMATION: Alloc protected

<400> SEQUENCE: 18

Gly Gly Gly Gly Gly Xaa Leu Val Pro Arg Gly Ser Gly Gly Xaa Gly
1               5                   10                  15

Gly Xaa Lys

<210> SEQ ID NO 19
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (13)..(13)
<223> OTHER INFORMATION: Xaa is bAla
<220> FEATURE:
<221> NAME/KEY: misc_feature
<222> LOCATION: (16)..(16)
<223> OTHER INFORMATION: Xaa is bAla
<220> FEATURE:
<221> NAME/KEY: MISC_FEATURE
<222> LOCATION: (19)..(19)
<223> OTHER INFORMATION: Biotinylated

<400> SEQUENCE: 19

Gly Gly Gly Gly Gly Glu Asn Leu Tyr Phe Gln Ser Xaa Gly Gly Xaa
1               5                   10                  15

Gly Gly Lys

<210> SEQ ID NO 20
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 20

Cys Ala Phe Ile Gln Ser Leu Lys Asp Asp Pro Ser
1               5                   10

<210> SEQ ID NO 21
<211> LENGTH: 6
```

```
<212> TYPE: PRT
<213> ORGANISM: Artificial Sequence
<220> FEATURE:
<223> OTHER INFORMATION: Synthetic Polypeptide

<400> SEQUENCE: 21

Glu Cys Gly Gly Leu Leu
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Glutamic acid coupled to polypeptide through
      side chain carboxylate

<400> SEQUENCE: 22

Glu Cys Gly Gly Leu Leu
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 23

Asp Cys Gly Pro Leu Leu
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Glutamic acid coupled to polypeptide through
      side chain carboxylate

<400> SEQUENCE: 24

Glu Cys Gly Pro Leu Leu
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 25

Asp Glu Cys Gly Lys Leu Leu
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic Polypeptide
```

```
<220> FEATURE:
<221> NAME/KEY: MISC_FEATURE
<222> LOCATION: (1)..(1)
<223> OTHER INFORMATION: Glutamic acid coupled to polypeptide through
      side chain carboxylate

<400> SEQUENCE: 26

Glu Cys Gly Lys Leu Leu
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 27

Asn Cys Gly His Leu Leu
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Glutamic acid coupled to polypeptide through
      side chain carboxylate

<400> SEQUENCE: 28

Glu Cys Gly His Leu Leu
1               5

<210> SEQ ID NO 29
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 29

Gln Cys Gly Leu Leu Leu
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Glutamic acid coupled to polypeptide through
      side chain carboxylate

<400> SEQUENCE: 30

Glu Cys Gly Leu Leu Leu
1               5

<210> SEQ ID NO 31
<211> LENGTH: 17
<212> TYPE: PRT
<213> ORGANISM: Artificial Sequence
<220> FEATURE:
```

<223> OTHER INFORMATION: Synthetic Polypeptide

<400> SEQUENCE: 31

Cys Ala Cys Gly Ala Leu Tyr Lys Lys Gly Ser Phe Ala Gly Cys Ala
1               5                   10                  15

Cys

<210> SEQ ID NO 32
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 32

Cys Ala Gly Cys Ala Leu Tyr Lys Lys Gly Ser Phe Ala Cys Gly Ala
1               5                   10                  15

Cys

<210> SEQ ID NO 33
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 33

Cys Cys Ala Gly Ala Leu Tyr Lys Lys Gly Ser Phe Ala Gly Ala Cys
1               5                   10                  15

Cys

<210> SEQ ID NO 34
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 34

Ala Leu Phe Ala Leu Phe Ala Leu Phe Ala Leu Phe Ala Leu Phe Ala
1               5                   10                  15

Leu Phe Ala Leu Phe
            20

<210> SEQ ID NO 35
<211> LENGTH: 37
<212> TYPE: PRT
<213> ORGANISM: Artificial Sequence
<220> FEATURE:
<223> OTHER INFORMATION: Synthetic Polypeptide

<400> SEQUENCE: 35

Cys Asp Ile Asn Tyr Thr Ser Gly Phe Arg Asn Ser Asp Arg Ile Leu
1               5                   10                  15

Tyr Ser Ser Asp Trp Leu Ile Tyr Lys Thr Thr Asp His Tyr Gln Thr
            20                  25                  30

Phe Thr Lys Ile Arg
        35

<210> SEQ ID NO 36
<211> LENGTH: 130
<212> TYPE: PRT
<213> ORGANISM: Artificial Sequence

```
<220> FEATURE:
<223> OTHER INFORMATION: Synthetic Polypeptide
<220> FEATURE:
<221> NAME/KEY: misc_feature
<222> LOCATION: (28)..(28)
<223> OTHER INFORMATION: Xaa is Nle

<400> SEQUENCE: 36
```

Gly Gly Gly Gly Gly Ser Asp Leu Gly Lys Lys Leu Leu Glu Ala Ala
1               5                   10                  15

Arg Ala Gly Gln Asp Asp Glu Val Arg Ile Leu Xaa Ala Asn Gly Ala
            20                  25                  30

Asp Val Asn Ala Leu Asp Glu Asp Gly Leu Thr Pro Leu His Leu Ala
        35                  40                  45

Ala Gln Leu Gly His Leu Glu Ile Val Glu Val Leu Leu Lys Tyr Gly
    50                  55                  60

Ala Asp Val Asn Ala Glu Asp Asn Phe Gly Ile Thr Pro Leu His Leu
65                  70                  75                  80

Ala Ala Ile Arg Gly His Leu Glu Ile Val Glu Val Leu Leu Lys His
                85                  90                  95

Gly Ala Asp Val Asn Ala Gln Asp Lys Phe Gly Lys Thr Ala Phe Asp
            100                 105                 110

Ile Ser Ile Asp Asn Gly Asn Glu Asp Leu Ala Glu Ile Leu Gln Lys
        115                 120                 125

Leu Asn
    130

```
<210> SEQ ID NO 37
<211> LENGTH: 31
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (28)..(28)
<223> OTHER INFORMATION: Xaa is Nle

<400> SEQUENCE: 37
```

Gly Gly Gly Gly Gly Ser Asp Leu Gly Lys Lys Leu Leu Glu Ala Ala
1               5                   10                  15

Arg Ala Gly Gln Asp Asp Glu Val Arg Ile Leu Xaa Ala Asn Gly
            20                  25                  30

```
<210> SEQ ID NO 38
<211> LENGTH: 33
<212> TYPE: PRT
<213> ORGANISM: Artificial Sequence
<220> FEATURE:
<223> OTHER INFORMATION: Synthetic Polypeptide

<400> SEQUENCE: 38
```

Cys Asp Val Asn Ala Leu Asp Glu Asp Gly Leu Thr Pro Leu His Leu
1               5                   10                  15

Ala Ala Gln Leu Gly His Leu Glu Ile Val Glu Val Leu Leu Lys Tyr
            20                  25                  30

Gly

```
<210> SEQ ID NO 39
<211> LENGTH: 33
<212> TYPE: PRT
<213> ORGANISM: Artificial Sequence
```

```
<220> FEATURE:
<223> OTHER INFORMATION: Synthetic Polypeptide

<400> SEQUENCE: 39

Cys Asp Val Asn Ala Glu Asp Asn Phe Gly Ile Thr Pro Leu His Leu
1               5                   10                  15

Ala Ala Ile Arg Gly His Leu Glu Ile Val Glu Val Leu Leu Lys His
            20                  25                  30

Gly

<210> SEQ ID NO 40
<211> LENGTH: 33
<212> TYPE: PRT
<213> ORGANISM: Artificial Sequence
<220> FEATURE:
<223> OTHER INFORMATION: Synthetic Polypeptide

<400> SEQUENCE: 40

Cys Asp Val Asn Ala Gln Asp Lys Phe Gly Lys Thr Ala Phe Asp Ile
1               5                   10                  15

Ser Ile Asp Asn Gly Asn Glu Asp Leu Ala Glu Ile Leu Gln Lys Leu
            20                  25                  30

Asn

<210> SEQ ID NO 41
<211> LENGTH: 113
<212> TYPE: PRT
<213> ORGANISM: Artificial Sequence
<220> FEATURE:
<223> OTHER INFORMATION: Synthetic Polypeptide

<400> SEQUENCE: 41

Gly Gly Gly Ala Gln Val Ile Asn Thr Phe Asp Gly Val Ala Asp Tyr
1               5                   10                  15

Leu Gln Thr Tyr His Lys Leu Pro Asp Asn Tyr Ile Thr Lys Ser Glu
            20                  25                  30

Ala Gln Ala Leu Gly Trp Val Ala Ser Lys Gly Asn Leu Ala Asp Val
        35                  40                  45

Ala Pro Gly Lys Ser Ile Gly Gly Asp Ile Phe Ser Asn Arg Glu Gly
    50                  55                  60

Lys Leu Pro Gly Lys Ser Gly Arg Thr Trp Arg Glu Ala Asp Ile Asn
65                  70                  75                  80

Tyr Thr Ser Gly Phe Arg Asn Ser Asp Arg Ile Leu Tyr Ser Ser Asp
                85                  90                  95

Trp Leu Ile Tyr Lys Thr Thr Asp His Tyr Gln Thr Phe Thr Lys Ile
            100                 105                 110

Arg

<210> SEQ ID NO 42
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 42

Gly Gly Gly Ala Gln Val Ile Asn Thr Phe Asp Gly Val
1               5                   10

<210> SEQ ID NO 43
```

```
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 43

Cys Asp Tyr Leu Gln Thr Tyr His Lys Leu Pro Asp Asn Tyr Ile Thr
1               5                   10                  15

Lys Ser Glu Ala Gln Ala Leu Gly Trp Val
            20                  25

<210> SEQ ID NO 44
<211> LENGTH: 37
<212> TYPE: PRT
<213> ORGANISM: Artificial Sequence
<220> FEATURE:
<223> OTHER INFORMATION: Synthetic Polypeptide

<400> SEQUENCE: 44

Cys Ser Lys Gly Asn Leu Ala Asp Val Ala Pro Gly Lys Ser Ile Gly
1               5                   10                  15

Gly Asp Ile Phe Ser Asn Arg Glu Gly Lys Leu Pro Gly Lys Ser Gly
            20                  25                  30

Arg Thr Trp Arg Glu
        35

<210> SEQ ID NO 45
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 45

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 46
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 46

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 47
<211> LENGTH: 33
<212> TYPE: PRT
<213> ORGANISM: Artificial Sequence
<220> FEATURE:
<223> OTHER INFORMATION: Synthetic Polypeptide

<400> SEQUENCE: 47

Gly Cys Asx Arg Pro Arg Gly Asp Asn Pro Pro Leu Asx Cys Ser Gln
1               5                   10                  15

Asp Ser Asp Cys Leu Ala Gly Cys Val Cys Gly Pro Asn Gly Phe Cys
```

```
                      20              25              30
Gly

<210> SEQ ID NO 48
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 48

Ala Leu Phe Ala Leu Phe Ala
1               5
```

SOLID PHASE PEPTIDE SYNTHESIS PROCESSES AND ASSOCIATED SYSTEMS

RELATED APPLICATIONS

This application is a national stage filing under 35 U.S.C. §371 of International Application Number PCT/US2014/017970, filed Feb. 24, 2014, entitled "Solid Phase Peptide Synthesis Processes And Associated Systems," which is a continuation-in-part of U.S. patent application Ser. No. 13/833,745, filed Mar. 15, 2013, and entitled "Solid Phase Peptide Synthesis Processes and Associated Systems," each of which is incorporated herein by reference in its entirety for all purposes.

TECHNICAL FIELD

Systems and processes for performing solid phase peptide synthesis are generally described.

BACKGROUND

Solid phase peptide synthesis is a process used to chemically synthesize peptides on solid supports. In solid phase peptide synthesis, an amino acid or peptide is bound, usually via the C-terminus, to a solid support. New amino acids are added to the bound amino acid or peptide via coupling reactions. Due to the possibility of unintended reactions, protection groups are typically used. To date, solid phase peptide synthesis has become standard practice for chemical peptide synthesis. The broad utility of solid phase peptide synthesis has been demonstrated by the commercial success of automated solid phase peptide synthesizers. Though solid phase peptide synthesis has been used for over 30 years, fast synthesis techniques have not yet been developed. Accordingly, improved processes and systems are needed.

SUMMARY

Solid phase peptide synthesis processes and associated systems are generally described. Certain embodiments relate to systems and methods which can be used to perform solid phase peptide synthesis quickly while maintaining high yield. In some embodiments, reagents can be heated, transported, and/or mixed in ways that reduce the amount of time required to perform solid phase peptide synthesis. The subject matter of the present invention involves, in some cases, interrelated products, alternative solutions to a particular problem, and/or a plurality of different uses of one or more systems and/or articles.

In some embodiments, a process for adding amino acid residues to peptides is provided. The process, in certain embodiments, comprises heating a stream comprising amino acids such that the temperature of the amino acids is increased by at least about 1° C.; and exposing the heated amino acids to a plurality of peptides immobilized on a solid support, wherein the heating step is performed prior to and within about 30 seconds of exposing the heated amino acids to the peptides.

In certain embodiments, the process comprises providing a plurality of peptides comprising protection groups, each peptide immobilized on a solid support; performing a first amino acid addition cycle comprising exposing amino acids to the immobilized peptides such that an amino acid residue is added to at least about 99% of the immobilized peptides; and performing a second amino acid addition cycle comprising exposing amino acids to the immobilized peptides such that an amino acid residue is added to at least about 99% of the immobilized peptides. In some embodiments, the total amount of time between the ends of the first and second amino acid addition cycles is about 10 minutes or less and the protection groups comprise fluorenylmethyloxycarbonyl protection groups and/or the total amount of time between the ends of the first and second amino acid addition cycles is about 5 minutes or less.

In certain embodiments, the process comprises providing a plurality of peptides immobilized on a solid support; and exposing activated amino acids to the immobilized peptides such that at least a portion of the activated amino acids are bonded to the immobilized peptides to form newly-bonded amino acid residues; wherein an amino acid residue is added to at least about 99% of the immobilized peptides within about 1 minute or less.

In certain embodiments, the process comprises flowing a first stream comprising amino acids; flowing a second stream comprising an amino acid activating agent; merging the first and second streams to form a mixed fluid comprising activated amino acids; and within about 30 seconds after merging the first and second streams to form the mixed fluid, exposing the mixed fluid to a plurality of peptides immobilized on a solid support.

In certain embodiments, the process comprises providing a plurality of peptides comprising protection groups, each peptide immobilized on a solid support; exposing a deprotection reagent to the immobilized peptides to remove protection groups from at least a portion of the immobilized peptides; removing at least a portion of the deprotection reagent; exposing activated amino acids to the immobilized peptides such that at least a portion of the activated amino acids are bonded to the immobilized peptides to form newly-bonded amino acid residues; and removing at least a portion of activated amino acids that do not bond to the immobilized peptides. In some embodiments, an amino acid residue is added to at least about 99% of the immobilized peptides during the amino acids exposing step. In certain embodiments, the total amount of time taken to perform the combination of all of the deprotection reagent exposing step, the deprotection reagent removal step, the activated amino acid exposing step, and the activated amino acid removal step is about 10 minutes or less and the protection groups comprise fluorenylmethyloxycarbonyl protection groups and/or the total amount of time taken to perform the combination of all of the deprotection reagent exposing step, the deprotection reagent removal step, the activated amino acid exposing step, and the activated amino acid removal step is about 5 minutes or less.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 5A-5B are, according to one set of embodiments, (A) a chromatogram and mass spectrum for a synthesized PnIA (A10L) peptide (SEQ ID NO: 4) and (B) a chromatogram and mass spectrum for a synthesized HIV-1 PR (81-99) peptide (SEQ ID NO: 5);

DETAILED DESCRIPTION

Systems and processes for performing solid phase peptide synthesis are generally described. Solid phase peptide synthesis is a known process in which amino acid residues are added to peptides that have been immobilized on a solid support. In certain embodiments, the inventive systems and methods can be used to perform solid phase peptide synthesis quickly while maintaining high yields. Certain embodiments relate to processes and systems that may be used to heat, transport, and/or mix reagents in ways that reduce the amount of time required to perform solid phase peptide synthesis.

Figure 1:
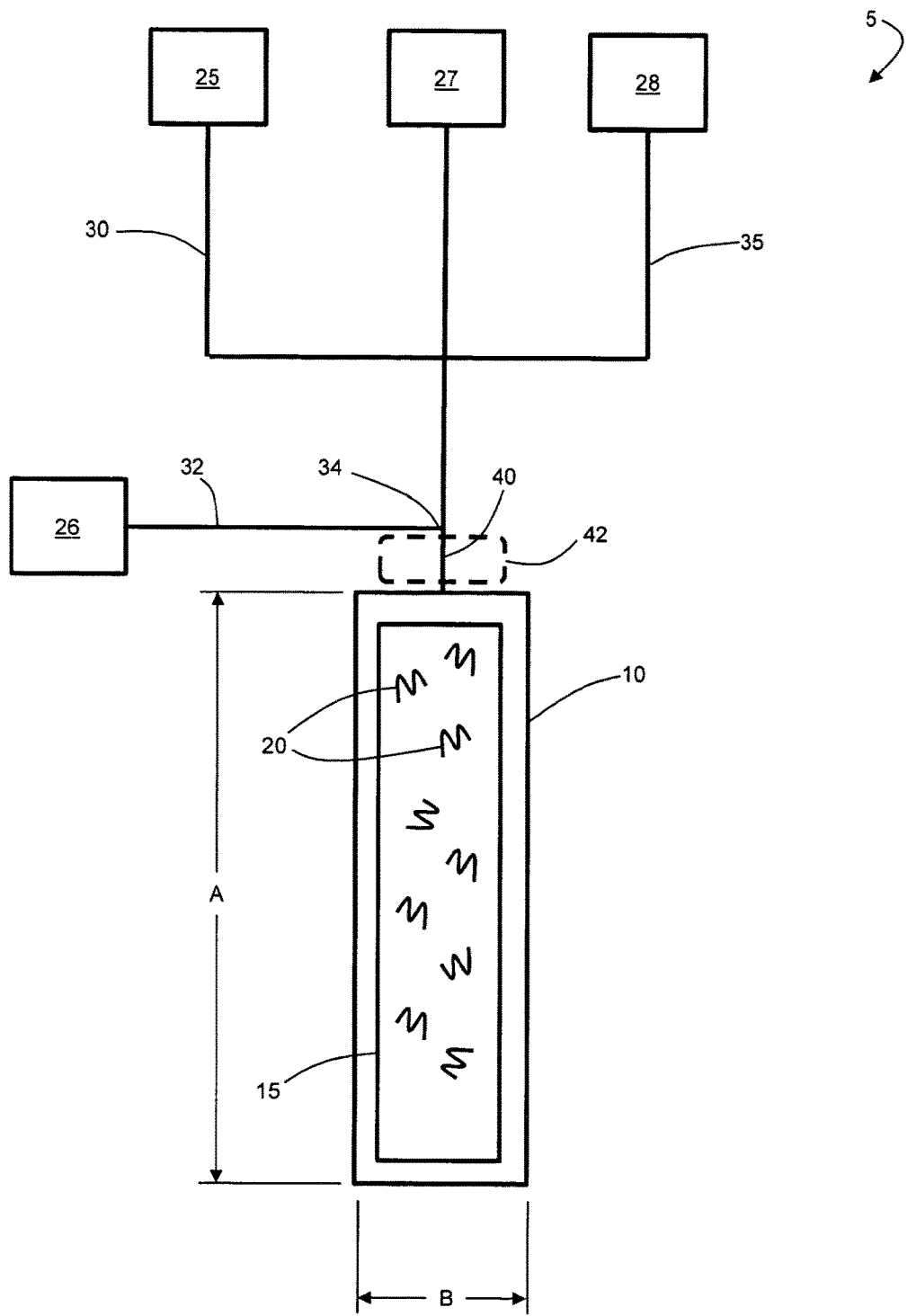
FIG. 1 is a schematic illustration of a system for performing peptide synthesis, according to one set of embodiments.

Certain embodiments relate to a process for adding amino acid(s) to an immobilized peptide. FIG. 1 is a schematic illustration of an exemplary system 5 which can be used to perform certain of the inventive processes described herein. The systems and methods described herein (e.g. system 5 in FIG. 1) can, in certain embodiments, involve flow-based synthesis (as opposed to batch-based synthesis, which is employed in many traditional solid phase peptide synthesis systems). In some such embodiments, continuous peptide synthesis can be performed, in which fluid (of one form or another) is substantially continuously transported over the immobilized peptides. For example, reagents and rinsing fluids may be alternatively and continuously transported over the immobilized peptides, in certain embodiments.

In some embodiments, peptides 20 may be immobilized on a solid support 15. Solid support 15 may be contained within a vessel, such as reactor 10. In some embodiments, and as shown in FIG. 1, a plurality of reagent reservoirs may be located upstream of and fluidically connected to reactor 10. In some embodiments, a reagent reservoir 25 contains amino acids (e.g., pre-activated amino acids and/or amino acids that are not fully activated). In some instances, a reagent reservoir 26 contains an amino acid activating agent (e.g., an alkaline liquid, a carbodiimide, and/or an uronium activating agent), capable of completing the activation of the amino acids. In certain embodiments, a reagent reservoir 27 contains a deprotection reagent, such as piperidine or trifluoroacetic acid. A reagent reservoir 28 may contain a solvent, such as dimethylformamide (DMF), that may be used, e.g., in a reagent removal step. While single reservoirs have been illustrated in FIG. 1 for simplicity, it should be understood that in FIG. 1, where single reservoirs are illustrated, multiple reservoirs (e.g., each containing different types of amino acids, different types of deprotection agents, etc.) could be used in place of the single reservoir.

In certain embodiments, peptides 20 comprise protection groups, for example, on the N-termini of the peptides. As used herein, the term "protection group" is given its ordinary meaning in the art. Protection groups include chemical moieties that are attached to or are configured to be attached to reactive groups (i.e., the protected groups) within a molecule (e.g., peptides) such that the protection groups prevent or otherwise inhibit the protected groups from reacting. Protection may occur by attaching the protection group to the molecule. Deprotection may occur when the protection group is removed from the molecule, for example, by a chemical transformation which removes the protection group.

In some embodiments, a plurality of peptides comprising protection groups may be bound to a solid support such that each peptide is immobilized on the solid support. For example, the peptides may be bound to the solid support via their C termini, thereby immobilizing the peptides.

In some embodiments, the process of adding amino acid residues to immobilized peptides comprises exposing a deprotection reagent to the immobilized peptides to remove at least a portion of the protection groups from at least a portion of the immobilized peptides. The deprotection reagent exposure step can be configured, in certain embodiments, such that side-chain protection groups are preserved, while N-terminal protection groups are removed. For instance, in certain embodiments, the protection group used to protect the peptides comprises fluorenylmethyloxycarbonyl (Fmoc). In some such embodiments, a deprotection reagent comprising piperidine (e.g., a piperidine solution) may be exposed to the immobilized peptides such that the Fmoc protection groups are removed from at least a portion of the immobilized peptides. In some embodiments, the protection group used to protect the peptides comprises tert-butyloxycarbonyl (Boc). In some such embodiments, a deprotection reagent comprising trifluoroacetic acid may be exposed to the immobilized peptides such that the Boc protection groups are removed from at least a portion of the immobilized peptides. In some instances, the protection groups (e.g., tert-butoxycarbonyl, i.e., Boc) may be bound to the N-termini of the peptides.

In some embodiments, the process of adding amino acid residues to immobilized peptides comprises removing at least a portion of the deprotection reagent. In some embodiments, at least a portion of any reaction byproducts (e.g., removed protection groups) that may have formed during the deprotection step can be removed. In some instances, the deprotection reagent (and, in certain embodiments byproducts) may be removed by washing the peptides, solid support, and/or surrounding areas with a fluid (e.g., a liquid such as an aqueous or non-aqueous solvent, a supercritical fluid, and/or the like), for example stored in optional reservoir 28. In some instances, removing the deprotection reagent and reaction byproducts may improve the performance of subsequent steps (e.g., by preventing side reactions). In certain embodiments, the performance of subsequent steps is not dependent on the removal of at least a portion (e.g., substantially all) of the deprotection reagent and/or reaction byproducts. In some such cases, the removal step is optional. In embodiments in which the removal step is optional, the removal step may be reduced (e.g., reduction in time of the removal step, reduction in the amount of solvent used in the removal step) and/or eliminated. The reduction or elimination of one or more removal steps may reduce the overall cycle time. It should be understood that if an optional removal step is reduced or eliminated the subsequent step in the addition cycle may serve to remove at least a portion of the deprotection reagent and/or reaction byproducts, e.g., due to fluid flow in the system.

The process of adding amino acid residues to immobilized peptides comprises, in certain embodiments, exposing activated amino acids to the immobilized peptides such that at least a portion of the activated amino acids are bonded to the immobilized peptides to form newly-bonded amino acid residues. For example, the peptides may be exposed to activated amino acids that react with the deprotected N-termini of the peptides. In certain embodiments, amino acids can be activated for reaction with the deprotected peptides by mixing an amino acid-containing stream with an activation agent stream, as discussed in more detail below. In some instances, the amine group of the activated amino acid may be protected, such that addition of the amino acid results in an immobilized peptide with a protected N-terminus.

In some embodiments, the process of adding amino acid residues to immobilized peptides comprises removing at least a portion of the activated amino acids that do not bond to the immobilized peptides. In some embodiments, at least a portion of the reaction byproducts that may form during the activated amino acid exposure step may be removed. In some instances, the activated amino acids and byproducts may be removed by washing the peptides, solid support, and/or surrounding areas with a fluid (e.g., a liquid such as an aqueous or non-aqueous solvent, a supercritical fluid, and/or the like), for example stored in optional reservoir 28. In some instances, removing at least a portion of the activated amino acids and reaction byproducts may improve the performance of subsequent steps (e.g., by preventing side reactions). In certain embodiments, the performance of subsequent steps is not dependent on the removal of at least a portion (e.g., substantially all) of the activated amino acids and/or reaction byproducts. In some such cases, the removal step is optional. In embodiments in which the removal step is optional, the removal step may be reduced (e.g., reduction in time of the removal step, reduction in the amount of solvent used in the removal step) and/or eliminated. The reduction or elimination of one or more removal step may reduce the overall cycle time. It should be understood that if an optional removal step is reduced or eliminated the subsequent step in the addition cycle may serve to remove at least a portion of the activated amino acids and/or reaction byproducts, e.g., due to fluid flow in the system.

It should be understood that the above-referenced steps are exemplary and an amino acid addition cycle need not necessarily comprise all of the above-referenced steps. For example, an amino acid addition cycle may not include the deprotection reagent removal step and/or the activated amino acid removal step. Generally, an amino acid addition cycle includes any series of steps that results in the addition of an amino acid residue to a peptide.

In certain embodiments, during the amino acid addition steps, adding the amino acid can result in the peptide incorporating a single additional amino acid residue (i.e., a single amino acid residue can be added to the immobilized peptides such that a given peptide includes a single additional amino acid residue after the addition step). In some such embodiments, subsequent amino acid addition steps can be used to build peptides by adding amino acid residues individually until the desired peptide has been synthesized. In some embodiments, more than one amino acid residue (e.g., in the form of a peptide) may be added to a peptide immobilized on a solid support (i.e., a peptide comprising multiple amino acid residues can be added to a given immobilized peptide). Addition of peptides to immobilized peptides can be achieved through processes know to those of ordinary skill in the art (e.g., fragment condensation, chemical ligation). That is to say, during the amino acid addition step, adding an amino acid to an immobilized peptide can comprise adding a single amino acid residue to an immobilized peptide or adding a plurality of amino acid residues (e.g., as a peptide) to an immobilized peptide.

In some embodiments, amino acids can be added to peptides significantly faster than conventional methods. In certain embodiments, the total amount of time taken to perform the combination of steps may be influenced by the protection group. For instance, in certain embodiments in which the protection groups comprise fluorenylmethyloxycarbonyl (Fmoc), the total amount of time taken to perform the combination of all of the deprotection reagent exposing step, the deprotection reagent removal step, the activated amino acid exposing step, and the activated amino acid removal step is about 10 minutes or less, about 9 minutes or less, about 8 minutes or less, about 7 minutes or less, about 6 minutes or less, about 5 minutes or less, about 4 minutes or less, about 3 minutes or less, about 2 minutes or less, about 1 minute or less, from about 10 seconds to about 10 minutes, from about 10 seconds to about 9 minutes, from about 10 seconds to about 8 minutes, from about 10 seconds to about 7 minutes, from about 10 seconds to about 6 minutes, from about 10 seconds to about 5 minutes, from about 10 seconds to about 4 minutes, from about 10 seconds to about 3 minutes, from about 10 seconds to about 2 minutes, or from about 10 seconds to about 1 minute. In certain embodiments (including embodiments in which the protection groups comprise tert-butyloxycarbonyl (Boc), fluorenylmethyloxycarbonyl (Fmoc), and/or other types of protection groups), the total amount of time taken to perform the combination of all of the deprotection reagent exposing step, the deprotection reagent removal step, the activated amino acid exposing step, and the activated amino acid removal step is about 5 minutes or less, about 4 minutes or less, about 3 minutes or less, about 2 minutes or less, about 1 minute or less, from about 10 seconds to about 5 minutes, from about 10 seconds to about 4 minutes, from about 10 seconds to about 3 minutes, from about 10 seconds to about 2 minutes, or from about 10 seconds to about 1 minute.

In general, the total amount of time taken to perform the combination of all of the deprotection reagent exposing step, the deprotection reagent removal step, the activated amino acid exposing step, and the activated amino acid removal step is calculated by adding the amount of time it takes to perform the deprotection reagent exposing step to the amount of time it takes to perform the deprotection reagent removal step and to the amount of time it takes to perform the activated amino acid exposing step and to the amount of time it takes to perform the activated amino acid removal step.

In embodiments in which an addition cycle lacks one or more removal steps, as described herein, and the protection groups comprise fluorenylmethyloxycarbonyl (Fmoc), the total amount of time taken to perform the combination of all of the steps of the addition cycle (e.g., the deprotection reagent exposing step, the activated amino acid exposing step, and the activated amino acid removal step; the deprotection reagent exposing step, the deprotection reagent removal step, and the activated amino acid exposing step; the deprotection reagent exposing step and the activated amino acid exposing step) is about 10 minutes or less, about 9 minutes or less, about 8 minutes or less, about 7 minutes or less, about 6 minutes or less, about 5 minutes or less, about 4 minutes or less, about 3 minutes or less, about 2 minutes or less, about 1 minute or less, about 0.75 minute or less, from about 10 seconds to about 10 minutes, from about 10 seconds to about 9 minutes, from about 10 seconds to about 8 minutes, from about 10 seconds to about 7 minutes, from about 10 seconds to about 6 minutes, from about 10 seconds to about 5 minutes, from about 10 seconds to about 4 minutes, from about 10 seconds to about 3 minutes, from about 10 seconds to about 2 minutes, or from about 10 seconds to about 1 minute. In certain embodiments (including embodiments in which the protection groups comprise tert-butyloxycarbonyl (Boc), fluorenylmethyloxycarbonyl (Fmoc), and/or other types of protection groups), the total amount of time taken to perform the combination of all of the steps in an addition cycle lacking one or more removal steps is about 5 minutes or less, about 4 minutes or less, about 3 minutes or less, about 2 minutes or less, about 1 minute or less, from about 10 seconds to about 5 minutes, from about 10 seconds to about 4 minutes, from about 10 seconds to about 3 minutes, from about 10 seconds to about 2 minutes, or from about 10 seconds to about 1 minute.

In general, the total amount of time taken to perform the combination of all of the steps in an addition cycle lacking one or more removal steps is calculated by adding the amount of time it takes to perform the deprotection reagent exposing step to the amount of time it takes to perform the deprotection reagent removal step, if present, and to the amount of time it takes to perform the activated amino acid exposing step and to the amount of time it takes to perform the activated amino acid removal step, if present.

In certain embodiments, the first amino acid addition step (and/or subsequent amino acid addition steps) may add amino acids at a relatively high yield. For example, certain embodiments include exposing amino acids to the immobilized peptides such that an amino acid residue is added to at least about 99%, at least about 99.9%, at least about 99.99%, or substantially 100% of the immobilized peptides. In certain embodiments, a second (and, in some embodiments, a third, a fourth, a fifth, and/or a subsequent) amino acid addition cycle can be performed which may include exposing amino acids to the immobilized peptides such that an amino acid residue is added to at least about 99%, at least about 99.9%, at least about 99.99%, or substantially 100% of the immobilized peptides. In certain embodiments, the use of processes and systems of the present invention may allow the addition of more than one amino acid to the immobilized peptides to occur relatively quickly (including within any of the time ranges disclosed above or elsewhere herein), while maintaining a high reaction yield.

In certain embodiments, one or more amino acid addition steps can be performed while little or no double incorporation (i.e., adding multiple copies of a desired amino acid (e.g., single amino acid residues or peptides) during a single addition step). For example, in certain embodiments, multiple copies of the desired amino acid are bonded to fewer than about 1% (or fewer than about 0.1%, fewer than about 0.01%, fewer than about 0.001%, fewer than about 0.0001%, fewer than about 0.00001%, or substantially none) of the immobilized peptides during a first (and/or second, third, fourth, fifth, and/or subsequent) amino acid addition step.

In some embodiments, multiple amino acid addition cycles can be performed. Performing multiple amino acid addition cycles can result in more than one single-amino-acid residue (or more than one peptide, and/or at least one single-amino-acid residue and at least one peptide) being added to a peptide. In certain embodiments a process for adding more than one amino acid to immobilized peptides may comprise performing a first amino acid addition cycle to add a first amino acid and performing a second amino acid addition cycle to add a second amino acid. In certain embodiments, third, fourth, fifth, and subsequent amino acid addition cycles may be performed to produce an immobilized peptide of any desired length. In some embodiments, at least about 10 amino acid addition cycles, at least about 50 amino acid addition cycles, or at least about 100 amino acid addition cycles are performed, resulting in the addition of at least about 10 amino acid residues, at least about 50 amino acid residues, or at least about 100 amino acid residues to the immobilized peptides. In certain such embodiments, a relatively high percentage of the amino acid addition cycles (e.g., at least about 50%, at least about 75%, at least about 90%, at least about 95%, or at least about 99% of such amino acid addition cycles) can be performed at high yield (e.g., at least about 99%, at least about 99.9%, at least about 99.99%, or substantially 100%). In some such embodiments, a relatively high percentage of the amino acid addition cycles (e.g., at least about 50%, at least about 75%, at least about 90%, at least about 95%, or at least about 99% of such amino acid addition cycles) can be performed quickly, for example, within any of the time ranges specified above or elsewhere herein. In some such embodiments, a relatively high percentage of the amino acid addition cycles (e.g., at least about 50%, at least about 75%, at least about 90%, at least about 95%, or at least about 99% of such amino acid addition cycles) can be performed with limited or no double incorporation, for example, within any of the double incorporation ranges specified above or elsewhere herein.

In embodiments in which there are more than one addition cycles, the total amount of time that passes between the end of an amino acid addition cycle and a subsequent amino acid addition cycle may be relatively short. For example, in certain embodiments in which fluorenylmethyloxycarbonyl protection groups are employed, the total amount of time between the ends of the first and second amino acid addition cycles is about 10 minutes or less, about 9 minutes or less, about 8 minutes or less, about 7 minutes or less, about 6 minutes or less, about 5 minutes or less, about 4 minutes or less, about 3 minutes or less, about 2 minutes or less, about 1 minute or less, from about 10 seconds to about 10 minutes, from about 10 seconds to about 9 minutes, from about 10 seconds to about 8 minutes, from about 10 seconds to about 7 minutes, from about 10 seconds to about 6 minutes, from about 10 seconds to about 5 minutes, from about 10 seconds to about 4 minutes, from about 10 seconds to about 3 minutes, from about 10 seconds to about 2 minutes, or from about 10 seconds to about 1 minute. In certain embodiments in which protection groups comprising fluorenylmethyloxycarbonyl, tert-butyloxycarbonyl, and/or any other suitable protection group are employed, the total amount of time between the end of an amino acid addition cycle and a subsequent amino acid addition cycle may be about 5 minutes or less, about 4 minutes or less, about 3 minutes or less, about 2 minutes or less, about 1 minute or less, from about 10 seconds to about 5 minutes, from about 10 seconds to about 4 minutes, from about 10 seconds to about 3 minutes, from about 10 seconds to about 2 minutes, or from about 10 seconds to about 1 minute.

As mentioned above, certain aspects relate to processes and systems that allow the total time required for one or more addition cycles to be significantly reduced compared to previous solid phase peptide synthesis methods. Since the advent of continuous solid phase peptide synthesis over 30 years ago, continual efforts have focused on improving its utility and applicability. While these improvements have contributed to the commercial success of automated solid phase peptide synthesizers, reducing synthesis time still remains a significant barrier. Over 30 years of research and development in the field have been unable to produce fast synthesis techniques. Typical continuous solid phase peptide synthesis using Fmoc or Boc protection groups require 30 to 90 minutes to add a single amino acid. Certain processes and techniques have been discovered, with the context of the present invention, that address the long felt need to decrease synthesis time. For example, fast synthesis times may be achieved by employing specialized techniques for mixing, heating, and/or controlling pressure drop.

Certain steps in the amino acid addition cycle may require mixing of reagents. In some conventional systems, reagents are mixed a long time before exposure to the immobilized peptides, which may result in undesirable side reactions and/or reagent degradation prior to exposure to the immobilized peptides. In some instances, the side reactions and/or degradation adversely affects the yield and kinetics of one or more steps in the amino acid addition cycle (e.g., amino acid exposing step). In some conventional systems, reagents are mixed in the presence of the immobilized peptides, which may result, e.g., in slower reaction kinetics. One technique for achieving rapid peptide synthesis may involve merging reagent streams prior to, but within a short amount of time of, arrival at the immobilized peptides, as shown in FIG. 1.

In some embodiments, a process for adding amino acid residues to peptides comprises flowing a first stream comprising amino acids, flowing a second stream comprising an amino acid activating agent (e.g., an alkaline liquid, a carbodiimide, and/or an uronium activating agent). For example, referring back to FIG. 1, reagent reservoir 25 may comprise amino acids. Reagent reservoir 26 may comprise, in some such embodiments, an amino acid activating agent. The first and second streams may be merged to form a mixed fluid comprising activated amino acids. For example, referring to FIG. 1, amino acids from reservoir 25 can be flowed in first stream 30, and amino acid activating agent can be flowed in second stream 32. First stream 30 and second stream 32 can be mixed, for example, at point 34 of stream 40. The mixed fluid may comprise activated amino acids due to the activation of the amino acids by the amino acid activating agent.

In certain embodiments, after the amino acids have been activated, the immobilized peptides may be exposed to the mixed fluid within a relatively short period of time. For example, in certain embodiments, the plurality of peptides immobilized on the solid support may be exposed to the mixed fluid within about 30 seconds (or within about 15 seconds, within about 10 seconds, within about 5 seconds, within about 3 seconds, within about 2 seconds, within about 1 second, within about 0.1 seconds, or within about 0.01 seconds) after merging the first and second streams to form the mixed fluid.

In certain embodiments, merging reagent streams may be used in an amino acid addition cycle, as described herein. For example, a first fluid stream comprising amino acids and a second stream comprising an amino acid activating agent may be merged to form a mixed fluid comprising the activated amino acids within about 30 seconds prior to exposing the activated amino acids to peptides immobilized on a solid support. In some embodiments, in which more than one amino acid addition cycle is performed, one or more amino acid addition cycles (e.g., a first and a second amino acid addition cycle) may comprise merging a first fluid stream comprising amino acids and a second stream comprising an amino acid activating agent to form a mixed fluid comprising activated amino acids within about 30 seconds prior to exposing the amino acids to the solid support. It should be understood that merging reagent streams may be used in connection with any suitable step in the addition cycle and may be used in connection with one or more steps in an amino acid addition cycle.

In general, streams may be merged using any suitable technique known to those of skill in the art. In some embodiments, the streams may be merged by flowing the first stream and the second stream substantially simultaneously into a single stream (e.g., by merging channels through which the streams flow). Other merging methods may also be used.

Another technique for achieving fast synthesis times may involve heating a stream prior to, but within a short period of time of, arrival at the reactor. Supplying the reactor with a heated stream may alter the kinetics of a process occurring in the reactor. For example, exposing immobilized peptides, solid supports, or other synthesis components to a heated stream may alter the reaction kinetics and/or diffusion kinetics of the amino acid addition process. For example, exposing the peptides to a heated stream comprising activated amino acids may increase the rate at which amino acids are added to the peptides. In some embodiments, heating the stream prior to, but within a short period of time of arrival at the reactor may substantially reduce or eliminate the need to supply auxiliary heat (i.e., heat that is not from one or more pre-heated streams) to the reactor. In some instances, most or substantially all of the heat supplied to the reactor originates from the pre-heated stream. For example, in some embodiments, the percentage of thermal energy that is used to heat the reactor that originates from the pre-heated stream(s) may be greater than or equal to about 50%, greater than or equal to about 60%, greater than or equal to about 70%, greater than or equal to about 80%, greater than or equal to about 90%, greater than or equal to about 95%, or greater than or equal to about 99%. In some such embodiments, heating the system in this way can reduce the time required to heat the reactor, immobilized peptides, solid support, activated amino acids, deprotection reagents, wash fluids, and/or other synthesis components to a desirable reaction temperature.

Thus, in some embodiments, a process for adding amino acid residues to peptides may comprise heating a stream comprising activated amino acids such that the temperature of the activated amino acids is increased by at least about 1° C. (or at least about 2° C., at least about 5° C., at least about 10° C., at least about 25° C., at least about 50° C., and/or less than or equal to about 450° C., less than or equal to about 300° C., less than or equal to about 200° C., less than or equal to about 100° C., and/or less than or equal to about 75° C.) prior to the heated amino acids being exposed to the immobilized peptides. In certain embodiments, a stream comprising any other component (e.g., a washing agent, a deprotection agent, or any other components) may be heated such that the temperature of the stream contents is increased by at least about 1° C. (or at least about 2° C., at least about 5° C., at least about 10° C., at least about 25° C., at least about 50° C., and/or less than or equal to about 450° C., less than or equal to about 300° C., less than or equal to about 200° C., less than or equal to about 100° C., and/or less than or equal to about 75° C.) prior to the stream contents being exposed to the immobilized peptides. In some instances, the heating step (e.g., the heating of the activated amino acids and/or the heating of any other component within a stream transported to the immobilized peptides) may be performed within about 30 seconds (or within about 15 seconds, within about 10 seconds, within about 5 seconds, within about 3 seconds, within about 2 seconds, within about 1 second, within about 0.1 seconds, or within about 0.01 seconds) of exposing the stream contents (e.g., the heated activated amino acids) to the immobilized peptides. In some such embodiments, and as illustrated in the exemplary embodiment of FIG. 1, such heating may be achieved by heating a location upstream of the immobilized peptides. In some such embodiments, the heating of the amino acids begins at least about 0.01 seconds, at least about 0.05 seconds, at least about 0.1 seconds, at least about 0.5 seconds, at least about 1 second, at least about 5 seconds, or at least about 10 seconds prior to exposure of the amino acids to the immobilized peptides. In certain embodiments, the amino acids are heated by at least about 1° C. (or at least about 2° C., at least about 5° C., at least about 10° C., at least about 25° C., at least about 50° C., and/or less than or equal to about 450° C., less than or equal to about 300° C., less than or equal to about 200° C., less than or equal to about 100° C., and/or less than or equal to about 75° C.) at least about 0.1 seconds, at least about 1 second, at least about 5 seconds, or at least about 10 seconds prior to the amino acids being exposed to the immobilized peptides.

Referring back to FIG. 1, for example, system 5 may comprise heating zone 42, within which the contents of stream 40 may be heated. Heating zone 42 may comprise a heater. In general, any suitable method of heating may be used to increase the temperature of a stream. One advantage of certain of the systems and methods described herein, is the ability to use simple and/or inexpensive heating methods and/or apparatus. For example, heating zone 42 may comprise a liquid bath (e.g., a water bath), a resistive heater, a gas convection-based heating element, or any other suitable heater. In some embodiments, a relatively low percentage of the thermal energy used to heat the inlet stream (and/or the reactor) may originate from electromagnetic radiation (e.g., microwave radiation). For example, in some embodiments, the percentage of the thermal energy used to heat the inlet stream(s) and/or the reactor that originates from electromagnetic radiation may be less than or equal to about 20%, less than or equal to about 15%, less than or equal to about 10%, less than or equal to about 5%, less than or equal to about 1%, or less than or equal to about 0.5%. In some embodiments, inlet stream(s) and/or the reactor may be heated without the use of electromagnetic radiation. In certain embodiments, the percentage of the thermal energy used to heat the inlet stream(s) and/or the reactor that originates from microwave radiation may be less than or equal to about 20%, less than or equal to about 15%, less than or equal to about 10%, less than or equal to about 5%, less than or equal to about 1%, or less than or equal to about 0.5%. In some embodiments, inlet stream(s) and/or the reactor may be heated without the use of microwave radiation. In some instances, the heating mechanism may be within a short distance of the immobilized peptides, for example, within about 5 meters, within about 1 meter, within about 50 cm, or within about 10 cm.

In some embodiments, including those illustrated in FIG. 1, both the heating of the amino acids and the merging of the amino acids with the amino acid activating agent (e.g., an alkaline liquid, a carbodiimide, and/or a uronium activating agent) can be performed before and within a relatively short time of the amino acids contacting the immobilized peptides. Heating the amino acids may be performed before, during, and/or after merging the stream comprising the amino acids with the stream comprising the amino acid activating agent.

In certain embodiments, heating a stream just prior to being exposed to the immobilized peptides (as opposed to heating the stream long before transport of the stream contents to the immobilized peptides) may minimize the thermal degradation of one or more reagents (such as, for example, the amino acids that are to be added to the peptides and/or the deprotection reagent) in the stream. Of course, as discussed above, heating a stream prior to arrival of the stream components can enhance the speed with which a reaction or washing step may be performed.

In some embodiments, a heating step may be used in an amino acid addition cycle, as described herein. For example, heating the activated amino acids, such that the temperature of the activated amino acids is increased by at least about 1° C., may be performed prior to and within about 30 seconds (or within any of the other time ranges mentioned elsewhere) of exposing the activated amino acids to the immobilized peptides. It should be understood that a heating step may be used prior to and within 30 seconds of any step of an amino acid addition cycle (e.g., deprotection reagent exposing step, deprotection reagent removal step, activated amino acid exposing step, activated amino acid removal step). In some embodiments, an amino acid addition cycle may comprise more than one heating step. For example, a heating step may be performed before a deprotection reagent exposing step and an activated amino acid exposing step.

In certain embodiments, in which more than one amino acid addition cycle is performed, one or more amino acid addition cycles (e.g., a first and a second amino acid addition cycle) may comprise one or more heating steps prior to and within about 30 seconds (or within any of the other time ranges mentioned elsewhere) of performing a step (e.g. deprotection reagent exposing step, deprotection reagent removal step, activated amino acid exposing step, activated amino acid removal step). For example, one or more amino acid addition cycles (e.g., a first and a second amino acid addition cycle) may comprise heating the activated amino acids prior to and within about 30 seconds (or within any of the other time ranges mentioned elsewhere) of exposing the activated amino acids to the immobilized peptides. In general, a heating step may be used in connection with any suitable step in the addition cycle and may be used in connection with one or more steps of any individual addition cycle or with all steps of a series of addition cycles.

As noted above, in some embodiments, heating a stream may increase the temperature of the stream contents (e.g., may increase the temperature of amino acids within the stream) by at least about 1° C., at least about 2° C., at least about 5° C., at least about 10° C., at least about 25° C., or at least about 50° C. It should be understood that the temperature of the stream after heating may be the same or different for different addition cycle steps and/or addition cycles. In some instances, the temperature of the stream after heating may be the same for one or more addition cycle steps and/or addition cycles. In some instances, heating a stream may increase the temperature of the stream contents (e.g., may increase the temperature of amino acids within the stream) by less than or equal to about 450° C., less than or equal to about 300° C., less than or equal to about 200° C., less than or equal to about 100° C. or less than or equal to about 75° C. Combinations of the above-referenced ranges are also possible (e.g., at least about 1° C. and less than or equal to about 100° C., at least about 1° C. and less than or equal to about 450° C., etc.).

Systems and methods for reducing pressure drop across the immobilized peptides may be used, according to certain embodiments, to improve the speed of peptide synthesis. In some embodiments, the flow rate of reagents across the immobilized peptides may influence the speed of peptide synthesis. For example, the time required for one or more steps in an amino acid addition cycle (e.g., deprotection reagent exposing step, deprotection reagent removal step, activated amino acid exposing step, activated amino acid removal step) may decrease with increasing flow rate. In general, the use of high flow rates ensures that the concentration of reagent near the immobilized peptides is not depleted as severely as might be observed when low flow rates are employed. In many traditional continuous solid phase peptide synthesis systems, the flow rate is limited by the pressure drop across the reactor. Pressure drop may occur due to expansion of the solid support during synthesis and/or due to improper sizing of process equipment. In certain embodiments, the pressure drop across the solid support during an amino acid addition cycle may not exceed about 700 psi for more than about 5% (or for more than about 1%) of the time period during which the cycle is performed. For example, in certain embodiments, during each step of an amino acid addition cycle (e.g. the deprotection reagent exposing step, the deprotection reagent removal step, the activated amino acid exposing step, and the activated amino acid removal step) the pressure drop across the solid support may not exceed about 700 psi for more than about 5% (or for more than about 1%) of the time period during which the step is performed. In embodiments in which more than one addition cycle is performed, the pressure drop during one or more addition cycles (e.g., the first and second amino acid addition cycle) may not exceed about 700 psi for more than about 5% (or for more than about 1%) of the time period during which the cycle is performed.

In some embodiments, the pressure drop across reactor during each step of an amino acid addition cycle and/or during one or more addition cycles may not exceed about 700 psi, about 600 psi, about 500 psi, about 400 psi, about 250 psi, about 100 psi, or about 50 psi for more than about 5% (or for more than about 1%) of the time period during which the step is performed.

In certain embodiments, the pressure drop across reactor may be reduced by using a process vessel (e.g., the column of a packed column) with a desirable aspect ratio. Generally, the aspect ratio of a process vessel is the ratio of the length of the vessel (substantially parallel to the direction of flow through the vessel) to the shortest width of the vessel (measured perpendicular to the length of the vessel). As an example, in the case of a cylindrical vessel, the aspect ratio would be the ratio of the height of the cylinder to the cross-sectional diameter of the cylinder. Referring back to FIG. 1, for example, the aspect ratio of reactor 10 would be the ratio of the length of dimension A to the length of dimension B (i.e., A:B). In some embodiments, the aspect ratio of the reactor may be less than or equal to about 20:1, less than or equal to about 10:1, less than or equal to about 5:1, less than or equal to about 3:1, less than or equal to about 2:1, less than or equal to about 1:1, less than or equal to about 0.5:1, less than or equal to about 0.2:1, or less than or equal to about 0.1:1 (and/or, in certain embodiments, as low as 0.01:1, or lower).

In some embodiments, relatively short addition cycles with high yields and/or limited and/or no double incorporation may be achieved by employing one or more of the techniques described herein. For example, certain of the systems and methods described herein may allow the amino acid exposing step (i.e., the step of exposing the activated amino acids to the immobilized peptides) to be performed (e.g., while achieving the high yields and/or avoiding double incorporation to any of the degrees described herein) in about 1 minute or less (e.g., about 30 seconds or less, about 15 seconds or less, about 10 seconds or less, about 7 seconds or less, or about 5 seconds or less, and/or, in certain embodiments, in as little as 1 second, or less). In some instances, certain of the systems and methods described herein may allow the deprotection reagent removal step and/or the activated amino acid removal step to be performed in about 2 minutes or less (e.g., about 1.5 minutes or less, about 1 minute or less, about 45 seconds or less, about 30 seconds or less, about 15 seconds or less, about 10 seconds or less, about 5 seconds or less, and/or, in certain embodiments, in as little as 1 second, or less). In certain embodiments, certain of the systems and methods described herein may allow the deprotection reagent exposing step (i.e., the step of exposing the immobilized peptides to the deprotection reagent) to be performed in about 20 seconds or less (e.g., about 15 seconds or less, about 10 seconds or less, about 8 seconds or less, about 5 seconds or less, about 1 second or less, and/or, in certain embodiments, in as little as 0.5 seconds, or less).

In certain cases, the time required for peptide synthesis may be influenced by the choice of protection group. For example, the use of Fmoc protection groups is generally understood to require longer synthesis cycle times. However, the systems and methods described herein can be used to perform fast amino acid addition, even when Fmoc protection group chemistries are employed. In some embodiments, the total time for an amino acid addition cycle may be low, regardless of the type of protection group that is being used.

In general, any protection group known to those of ordinary skill in the art can be used. Non-limiting examples of protection groups (e.g., n-terminal protection groups) include fluorenylmethyloxycarbonyl, tert-butyloxycarbonyl, allyloxycarbonyl (alloc), carboxybenzyl, and photolabile protection groups. In certain embodiments, immobilized peptides comprise fluorenylmethyloxycarbonyl protection groups. In some embodiments, immobilized peptides comprise tert-butyloxycarbonyl protection groups.

As described elsewhere, an amino acid activating agent may be used to activate or complete the activation of amino acids prior to exposing the amino acids to immobilized peptides. Any suitable amino acid activating agent may be used. In certain embodiments, the amino acid activating agent comprises an alkaline liquid. The amino acid activating agent comprises, in some embodiments, a carbodiimide, such as N,N'-dicyclohexylcarbodiimide (DCC), 1-ethyl-3-(3-dimethylaminopropyl)carbodiimide (EDC), and the like. In certain embodiments, the amino acid activating agent comprises a uronium activating agent, such as O-(Benzotriazol-1-yl)-N,N,N',N'-tetramethyluronium hexafluorophosphate (HBTU); 2-(7-Aza-1H-benzotriazole-1-yl)-1,1,3,3-tetramethyluronium hexafluorophosphate (HATU); 1-[(1-

(Cyano-2-ethoxy-2-oxoethylideneaminooxy) dimethylaminomorpholino)] uronium hexafluorophosphate (COMU); and the like.

As described elsewhere, peptides may be immobilized on a solid support. In general, any solid support may be used with any of the addition cycles described herein. Non-limiting examples of solid support materials include polystyrene (e.g., in resin form such as microporous polystyrene resin, mesoporous polystyrene resin, macroporous polystyrene resin), glass, polysaccharides (e.g., cellulose, agarose), polyacrylamide resins, polyethylene glycol, or copolymer resins (e.g., comprising polyethylene glycol, polystyrene, etc.).

The solid support may have any suitable form factor. For example, the solid support can be in the form of beads, particles, fibers, or in any other suitable form factor.

In some embodiments, the solid support may be porous. For example, in some embodiments macroporous materials (e.g., macroporous polystyrene resins), mesoporous materials, and/or microporous materials (e.g., microporous polystyrene resin) may be employed as a solid support. The terms "macroporous," "mesoporous," and "microporous," when used in relation to solid supports for peptide synthesis, are known to those of ordinary skill in the art and are used herein in consistent fashion with their description in the International Union of Pure and Applied Chemistry (IUPAC) Compendium of Chemical Terminology, Version 2.3.2, Aug. 19, 2012 (informally known as the "Gold Book"). Generally, microporous materials include those having pores with cross-sectional diameters of less than about 2 nanometers. Mesoporous materials include those having pores with cross-sectional diameters of from about 2 nanometers to about 50 nanometers. Macroporous materials include those having pores with cross-sectional diameters of greater than about 50 nanometers and as large as 1 micrometer.

One advantage of the inventive systems and methods described herein is that they can be used with standard solid support materials without degradation in performance. For example, in certain embodiments, a standard commercial polystyrene resin support can be used. In many previous systems, such supports collapsed when used in flow-based solid phase peptide synthesis systems, causing an increase in pressure drop. As the resin swells during synthesis, it becomes increasingly likely to collapse, which causes an increase in the pressure drop across the resin, requiring an increase in applied pressure to maintain a constant flow rate. The increase in applied pressure can lead to more severe collapse of the resin, leading to a positive feedback effect in which the pressure applied to the fluid must be repeatedly increased. At sufficiently high pressures, the resin may extrude through any frit or other system used to confine it. The systems and methods described herein can be used to manage pressure drop such that the resin (including standard polystyrene resins and other standard resins) do not collapse during synthesis or collapse only to a degree that does not result in the positive feedback effect described above, leading to a more stable and controllable system. In certain embodiments, the solid support is contained within a packed column.

In general, any peptide and/or protein may be synthesized using the methods and systems described herein. Non-limiting examples of peptides and/or proteins that may be synthesized using the methods and/or systems, described herein, include Glucagon-like peptides (e.g., GLP-1), Exenatide, Liraglutide, GLP-1 analogs (e.g., ZP10), Pramlinitide, Peptide YY, Glucagon, Teduglutide, Delmitide, Calcitonin (e.g., Salmon Calcitonin), parathyroid hormone, Bortezomib, Cilengitide, Leuprorelin, Histrelin, Goserelin, Stimuvax, Primovax, Nesiritide, Eptifibatide, Bivalirudin, Icatibant, Rotigaptide, Cyclosporin, MPB8298, Octreotide, Lanreotide, Desmopressin, Lypressin, Terlipressin, Oxytocin, Atosiban, Enfuvirtide, Thymalfasin, Daptamycin, Dentonin, Bacitracin, Gramidicin, Colistin, Pexiganan, Omiganan, Caspofungin, Micafungin, Anidulafungin, Histatin, Lactoferrin, Conotoxin, Nemifitide, natriuretic peptide, Vasopressin, Vasopressin analogs (e.g., Arg vasopressin, Lys vasopressin), Ziconotide, Echinocandins, Thymalfasin, and Somatostatin analogs (e.g., Octreotide, Lanreotide). Peptides and/or proteins for the treatment of diseases, such as, but not limited to, diabetes, gastroenterological disorders, orthopedic disorders (e.g., osteoporosis), cancer, cardiovascular disease, immunological disorders (i.e., autoimmune disorders), acromegaly, enuresis, infections (e.g., bacterial infections, fungal infections, viral infections), and central nervous system disorders, may be synthesized using the methods and systems described herein.

As used herein, the term "peptide" has its ordinary meaning in the art and may refer to amides derived from two or more amino carboxylic acid molecules (the same or different) by formation of a covalent bond from the carbonyl carbon of one to the nitrogen atom of another with formal loss of water. An "amino acid residue" also has its ordinary meaning in the art and refers to the composition of an amino acid (either as a single amino acid or as part of a peptide) after it has combined with a peptide, another amino acid, or an amino acid residue. Generally, when an amino acid combines with another amino acid or amino acid residue, water is removed, and what remains of the amino acid is called an amino acid residue. The term "amino acid" also has its ordinary meaning in the art and may include proteogenic and non-proteogenic amino acids.

The following examples are intended to illustrate certain embodiments of the present invention, but do not exemplify the full scope of the invention.

EXAMPLES

Standard solid phase peptide synthesis methods utilizing, e.g., Fmoc as a protecting group may require about 60 to 100 minutes to incorporate each amino acid residue and some specialized procedures use complex microwave systems to reduce this to about 20 minutes per residue. These examples describe the development of a flow platform that incorporates an amino acid residue in less than 10 minutes (e.g., every five minutes, every three minutes, every two minutes) under manual control or 1.8 minutes under automatic control, without microwave irradiation.

The flow based platform, described herein, further accelerates SPPS chemistry, far beyond what is believed to be currently possible with microwave assisted or other rapid peptide synthesizers, by leveraging a flow based approach. In addition to constantly supplying high concentration reagents, the flow-based platform overcomes a number of significant obstacles that can hinder standard and microwave-assisted approaches. First, the completely sealed reactor and heat exchanger can be immersed in a temperature controlled bath which allows solvents and reagents to be heated in a consistent and controlled manner immediately before reaching the resin bed. Rapid preheating is, according to certain embodiments, important to avoid thermal degradation of reagents while quickly reaching the desired temperature. However, this is extremely difficult in a batch system. Second, the flow platform can be scaled without increasing the cycle times. As demonstrated in the transition from the first to second generation reactors, increasing the diameter and flow rate effectively increases the maximum scale, without slowing the synthesis. Third, stirring is not required to effect adequate mass transfer, eliminating failure-prone moving parts, and facilitating scale up. Fourth, high quality peptides can be obtained quickly without double coupling, double deprotection, or colorimetric tests of coupling efficiency. Finally, automation of this system can allow for faster cycle times, in contrast to the often slow automation of batch synthesis.

Example 1

This example describes a flow based platform for rapid Fmoc solid phase peptide synthesis, in which each amino acid addition cycle was completed in less than five minutes. In this example, each step for amino acid addition (e.g., amide bond formation, washes, and N-termini deprotection) was carried out under a constant stream of fluid passed over a resin confined in a small, fritted plastic tube. Flow methods, as opposed to commonly used batch methods, allowed for the consistent rapid preheating, addition, and removal of solvents and reagents. The consistent rapid preheating, addition, and removal of solvents and reagents allowed a 5 minute cycle time, which included a 30 second amide-bond formation step. A number of model peptides were prepared, without double coupling or double deprotection. In addition, good yields and high purity, as shown by liquid chromatography-mass spectrometry (LC-MS), were achieved. This approach was also applied to the synthesis of a 58-residue protein from three polypeptide segments. The longest fragment, a 27 residue peptide, was prepared in 2.3 hours, which was 10 fold faster than conventional Fmoc methods. It is believed that automating various processing steps, increasing flow rate, reducing unnecessarily long wash times, and using a smaller aspect ratio reactor would substantially reduce the synthesis times reported here.

Figure 2A:
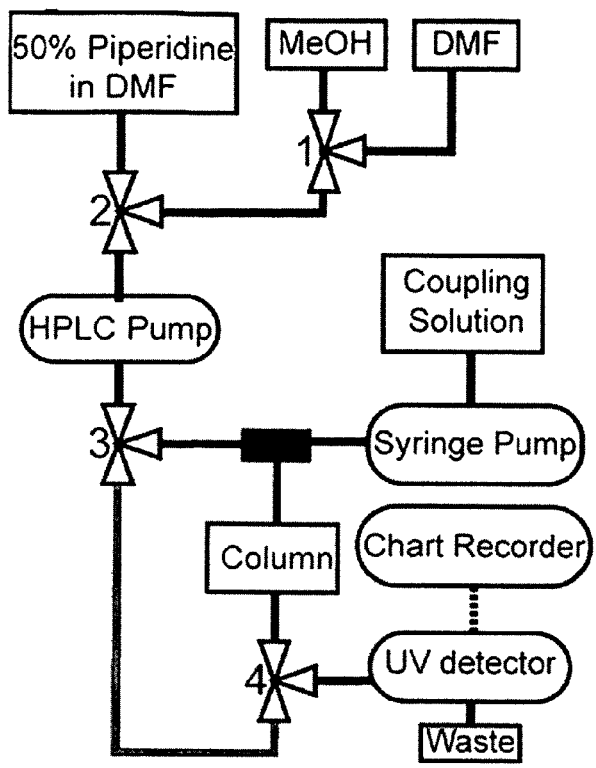
FIGS. 2A-2D are, according to certain embodiments, (A) an exemplary schematic diagram of a peptide synthesis system, (B) a photograph of an exemplary peptide synthesis system, (C) a chromatogram for a synthesized peptide Fmoc-ALFALFA-CONH$_2$, (SEQ ID NO: 1) and (D) an exemplary schematic diagram of a reactor.
Figure 2B:
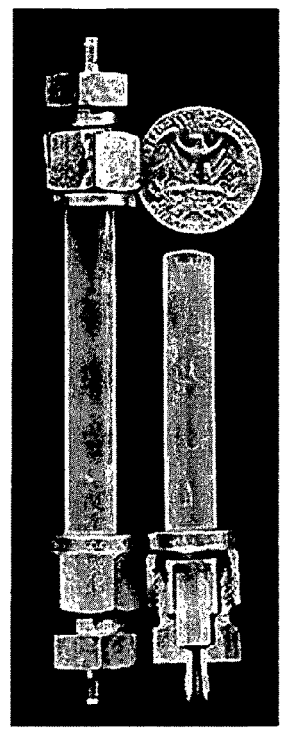

As shown in FIG. 2A, a high pressure liquid chromatography (HPLC) pump was used to deliver either a piperidine deprotection solution or a dimethylformamide (DMF) wash solvent to the reactor. A manually actuated 3-way valve was used to select which reagent was delivered to the reactor. The HPLC pump outlet was attached to the reactor via a luerlock quick connect. There was eight feet of 1/16" OD×0.03" ID tubing between the luerlock quick connect and reactor that served as a heat exchanger, or "preheat loop". For the coupling step, the quick connect was manually moved to a syringe pump, which delivered a solution of activated amino acid. It is believed that even faster performance than that reported here could be achieved by automating this step. The reactor effluent was passed through a UV detector to continuously monitor the absorbance at 304 nm, a region where Fmoc amino acids absorb strongly. The reactor was designed to be simple and easy to construct. A ¼" "inner diameter by 3.5" long perfluoroalkoxy tube with Swagelok reducing unions as the inlet and outlet was used. A frit was positioned in the outlet using a short piece of tubing with a ¼ in. outer diameter. Installation of the outlet fitting and concurrent compression of the ferrule and tube sealed the frit in place as seen in FIG. 2B. The total volume of the reactor was about 2.5 ml. This design held up to 100 mg of resin and was used to prepare peptides up to 27 residues in length.

Figure 2C:
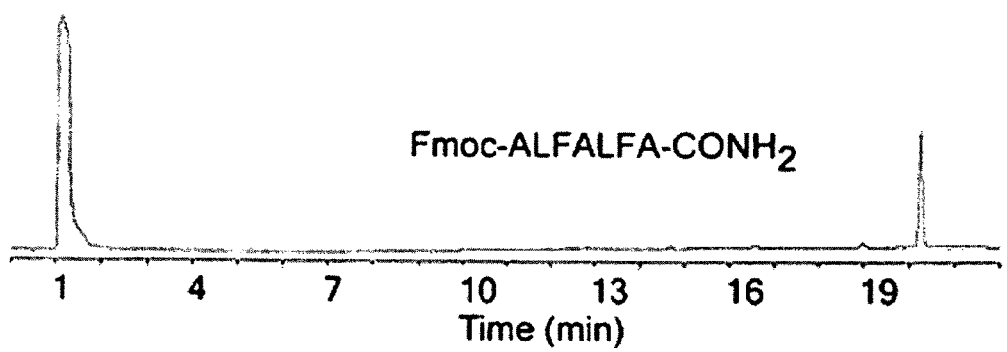
Figure 2D:
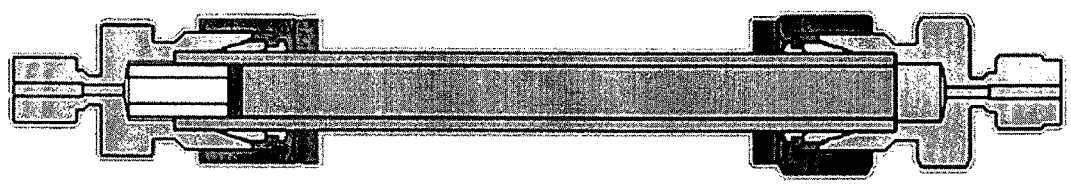

To verify the feasibility of Fmoc SPPS with this flow based SPPS system, the model peptide Fmoc-ALFALFA-CONH2 (SEQ ID NO: 1) was synthesized on a 0.1 mmol scale using 100 mg of resin. Based on an initial estimate, a 2 minute DMF wash at 10 mL/min, a 2 minute Fmoc deprotection step at 6 mL/min, and another DMF wash, and a 6 minute room temperature coupling with activated amino acid delivered at 1 mL/min were chosen as the starting point for an amino acid addition cycle. This sequence allowed efficient peptide synthesis in 12 minutes per residue. The reverse phase (RP)-HPLC trace for the crude peptide is shown in FIG. 2C.

Figure 3A:
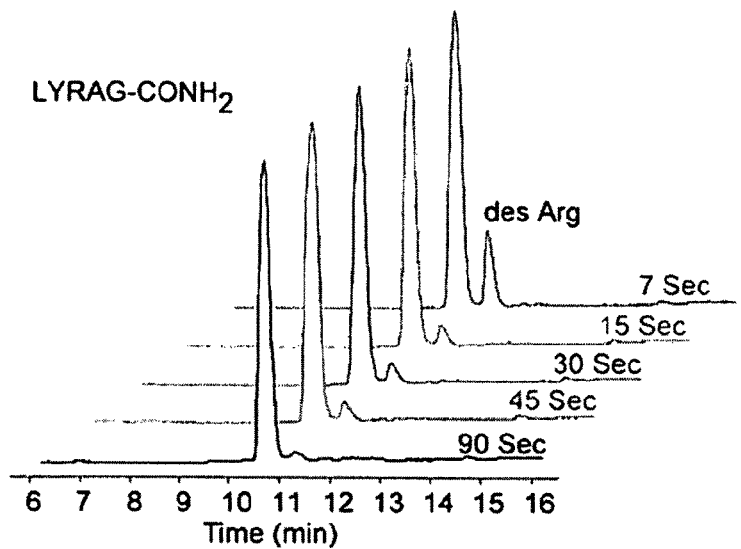
FIGS. 3A-3C are, according to one set of embodiments, (A) chromatograms of LYRAG-CONH$_2$ (SEQ ID NO: 2) peptides synthesized with different activated amino acid exposing times, (B) chromatograms of Fmoc-ALF-CONH$_2$ peptides synthesized with different activated amino acid exposing times, and (C) an exemplary synthetic timeline.
Figure 3B:
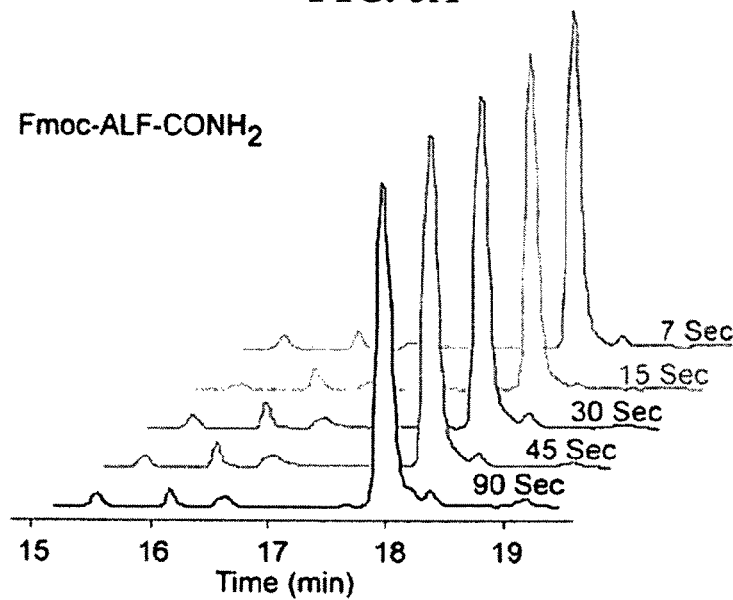
Figure 3C:
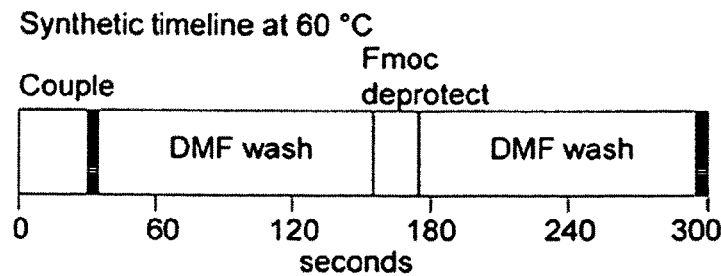

After validating this approach, improved wash step, Fmoc removal, and coupling times were determined. All subsequent studies were carried out at 60° C. to reduce the cycle time without significantly increasing formation of side products. It is believed that higher temperatures may improve synthetic outcomes and/or reduce the total time required for each amino acid addition cycle. The final synthetic timeline, which was used in all subsequent experiments in this example, is shown in FIG. 3C. The final synthetic timeline has a 2 minute DMF wash at 10 mL/min, a 20 second Fmoc deprotection step at 10 mL/min, another 2 minute DMF wash, and a 30 second coupling step with activated amino acid delivered at 12 mL/min. This approach was studied by synthesizing the peptide ACP (65-74). This peptide served as a model to validate the flow based SPPS platform, because ACP (65-74) was considered difficult to prepare. It is believed that substantial reductions in synthesis times could be achieved when synthesizing peptides that are easier to prepare.

In conventional systems, the main synthetic impurity in the synthesis of ACP (65-74) is a chromatographically resolved Val deletion. The LCMS data for the synthesis of ACP (65-74) with the flow based SPPS platform methodology, as well as two controls, is shown in FIGS. 4A-4D. Using the above protocol and the HATU coupling agent, a minor Val deletion product was observed. When using HBTU, more Val deletion was observed, which is consistent with prior reports. ACP (65-74) synthesized with the flow based SPPS platform, but at room temperature, showed large Val and Gln deletions, confirming that temperature is important. No major differences between the product composition from the room temperature synthesis and an analogous batch synthesis were observed. Two additional "difficult" peptides, a conotoxin variant and a fragment of the HIV-1 protease, were also synthesized. The LCMS data is shown in FIGS. 5A-5B. Both of these peptides contained cysteine residues that were observed to racemize during activation. Therefore, model studies using the peptide GCF were carried out. During the model study, several conditions that produced less than 1% diastereomer, as shown in FIGS. 6A-6E, were found. This level of racemization is consistent with literature for Fmoc protocols.

Figure 7A:
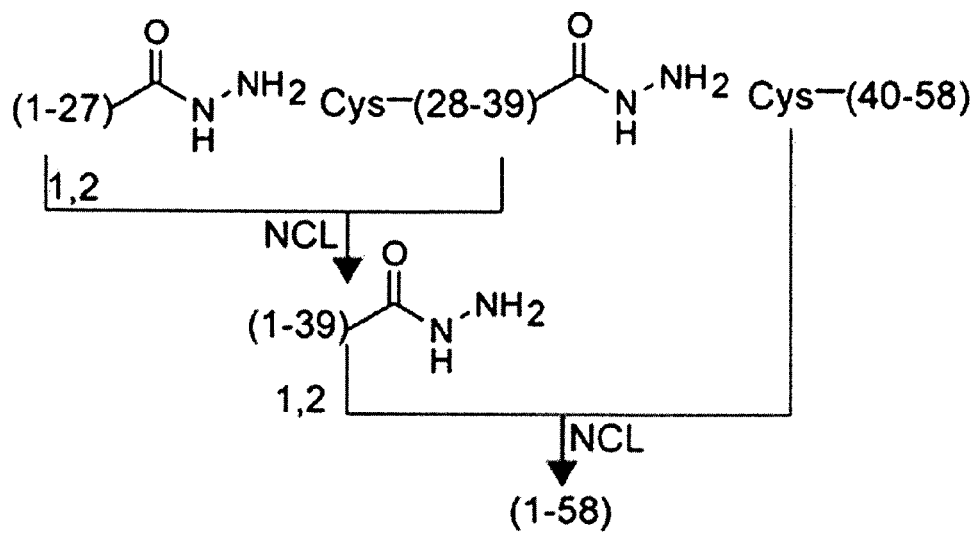
FIGS. 7A-7E are, according to certain embodiments, (A) an exemplary scheme for the chemical ligation of an affibody protein from three peptide fragments, (B) chromatogram and mass spectrum for a first affibody fragment (SEQ ID NO: 6), (C) chromatogram and mass spectrum for a second affibody fragment (SEQ ID NO: 7), (D) chromatogram and mass spectrum for a third affibody peptide fragment (SEQ ID NO: 8), and (E) chromatogram and mass spectrum for the purified affibody.
Figure 7B:
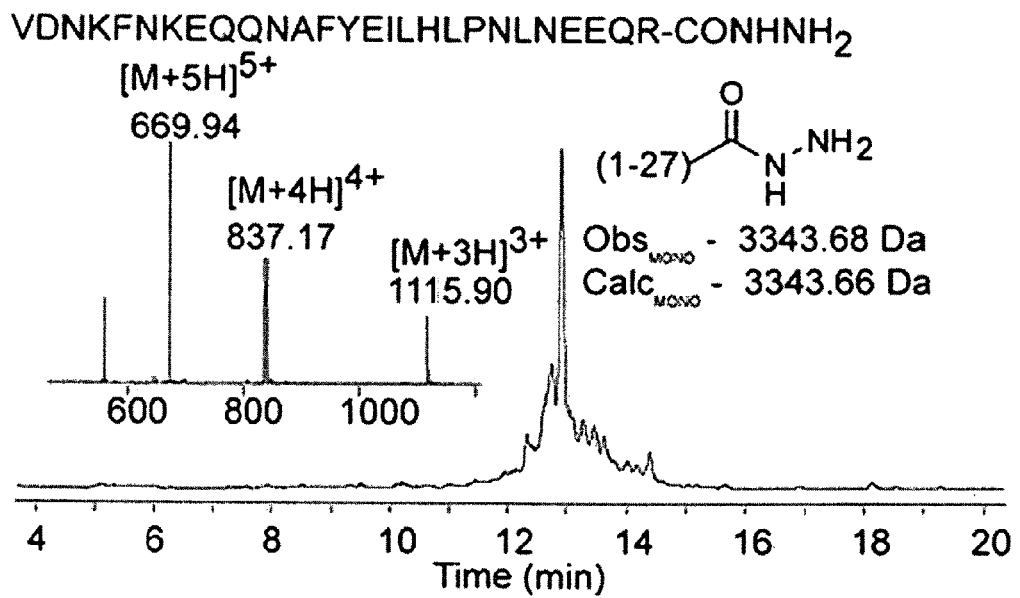
Figure 7C:
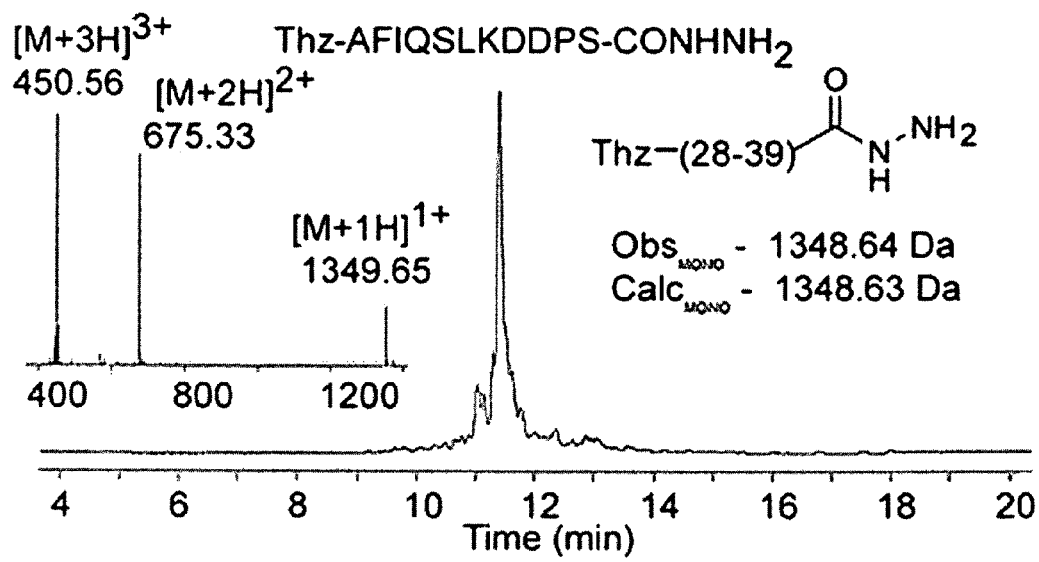
Figure 7D:
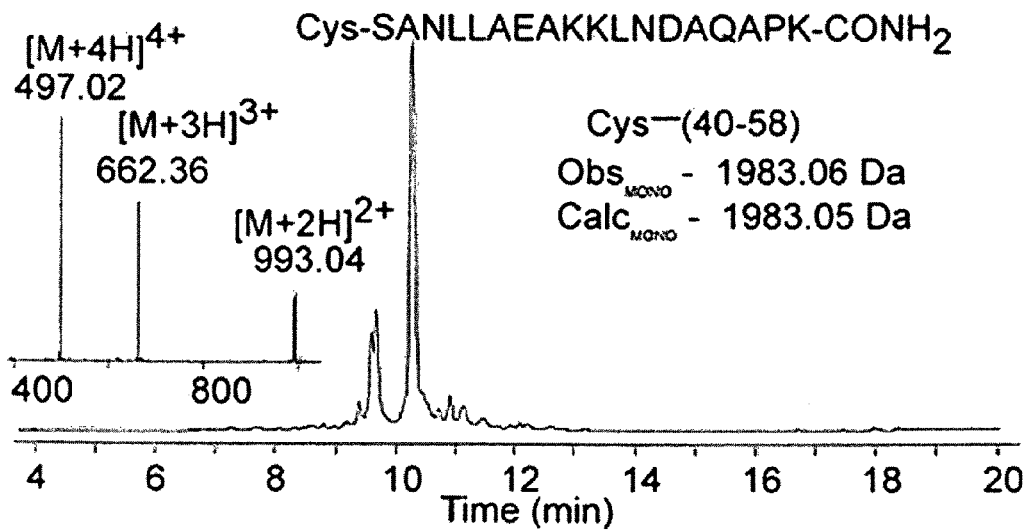
Figure 7E:
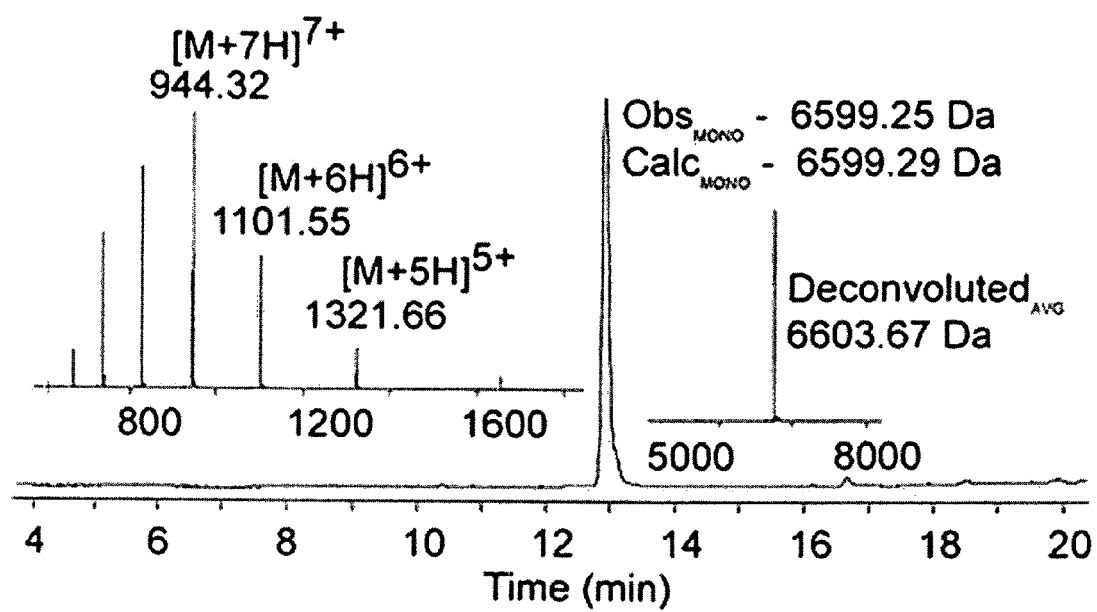
Figure 8A:
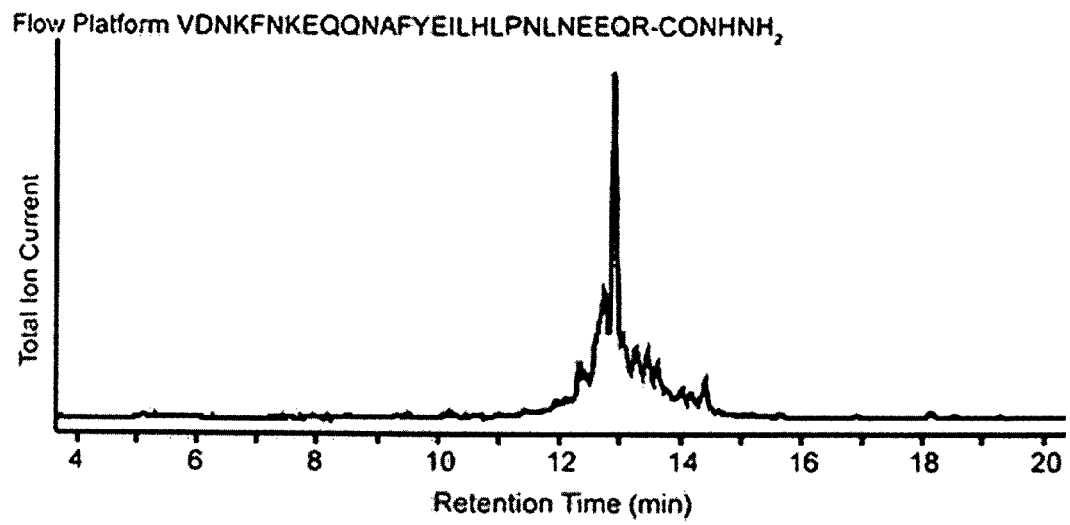
FIGS. 8A-8F are, according to certain embodiments, (A-B) total ion chromatograms for the N-terminal affibody fragment using Fmoc N-terminal protecting groups and a traditional manual arrangement using Boc N-terminal protecting groups, respectively (sequences in FIGS. 8A and 8B correspond to SEQ ID NOs.: 9 and 10, respectively), (C-D) total ion chromatograms for the middle affibody fragment using Fmoc N-terminal protecting groups and a traditional manual arrangement using Boc N-terminal protecting groups, respectively (sequences in FIGS. 8C and 8D correspond to SEQ ID NOs.: 11 and 12, respectively), and (E-F) total ion chromatograms for the C-terminal affibody fragment using Fmoc N-terminal protecting groups and a traditional manual arrangement using Boc N-terminal protecting groups, respectively (sequences in FIGS. 8E and 8F correspond to SEQ ID NOs.: 13 and 14, respectively)
Figure 8B:
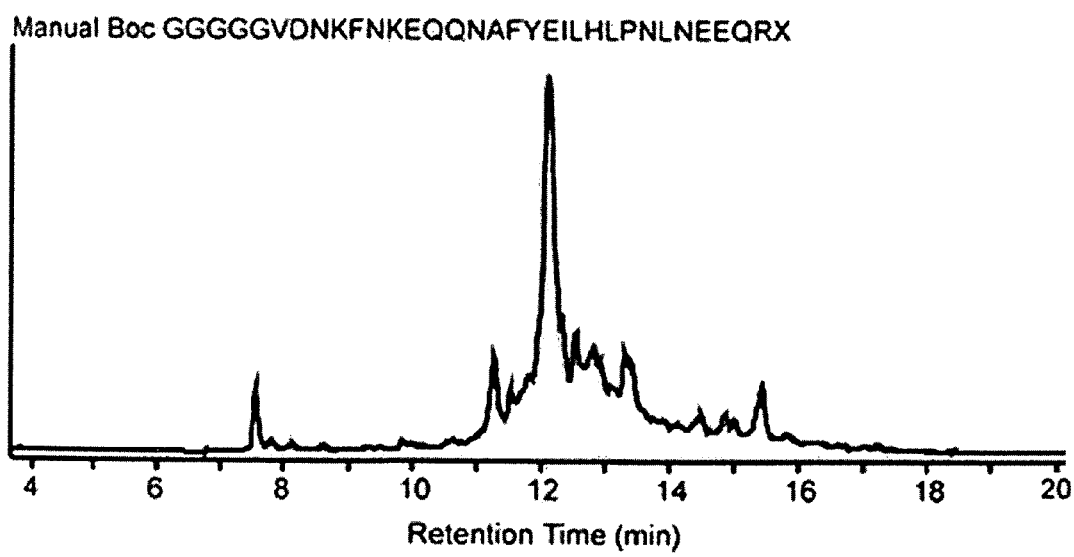
Figure 8C:
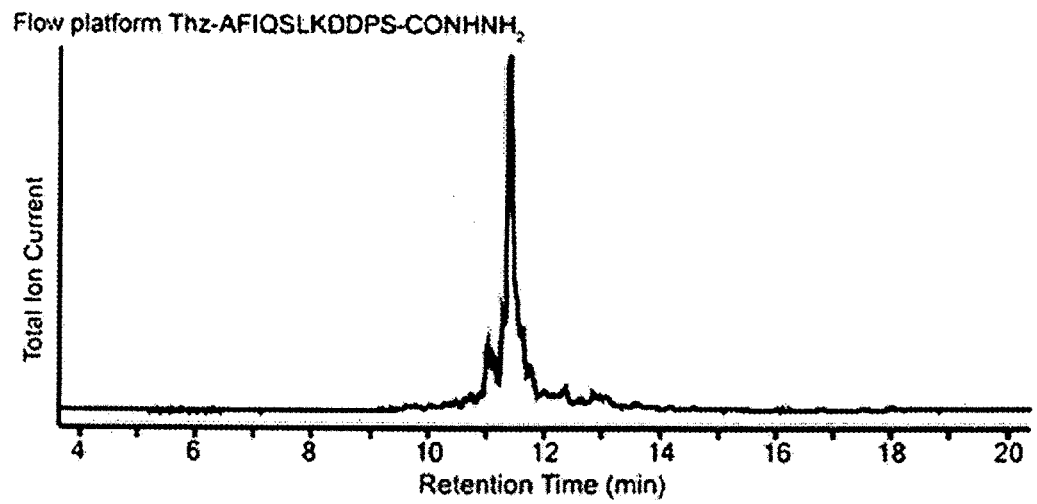
Figure 8D:
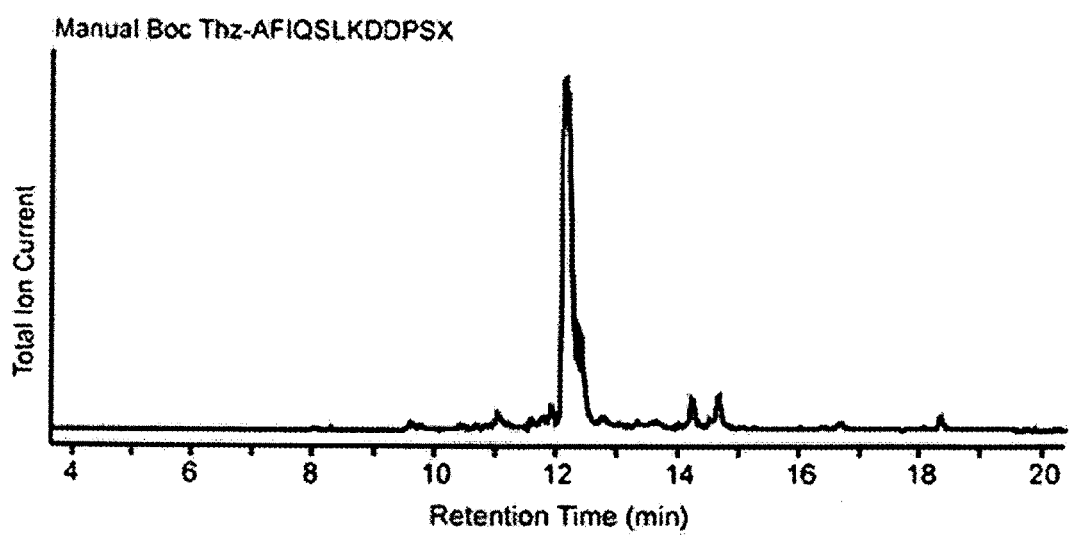
Figure 8E:
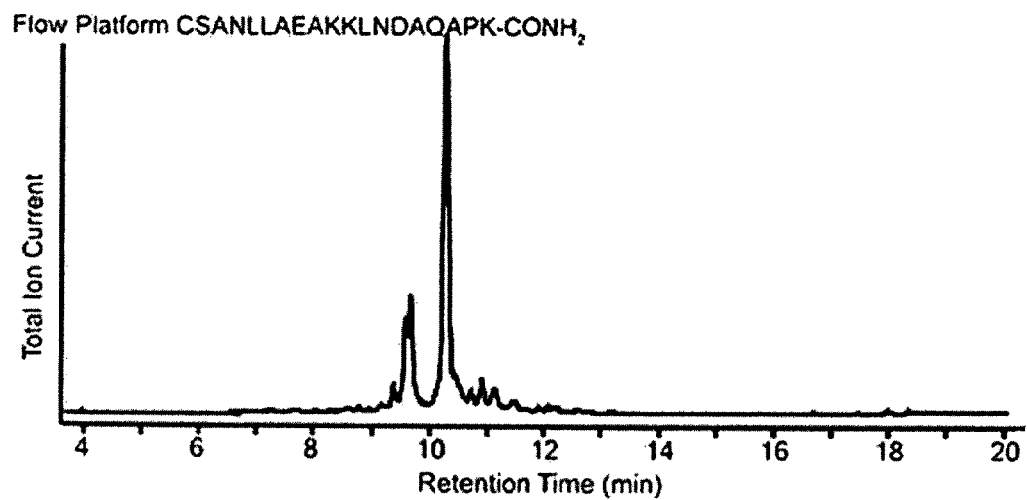
Figure 8F:
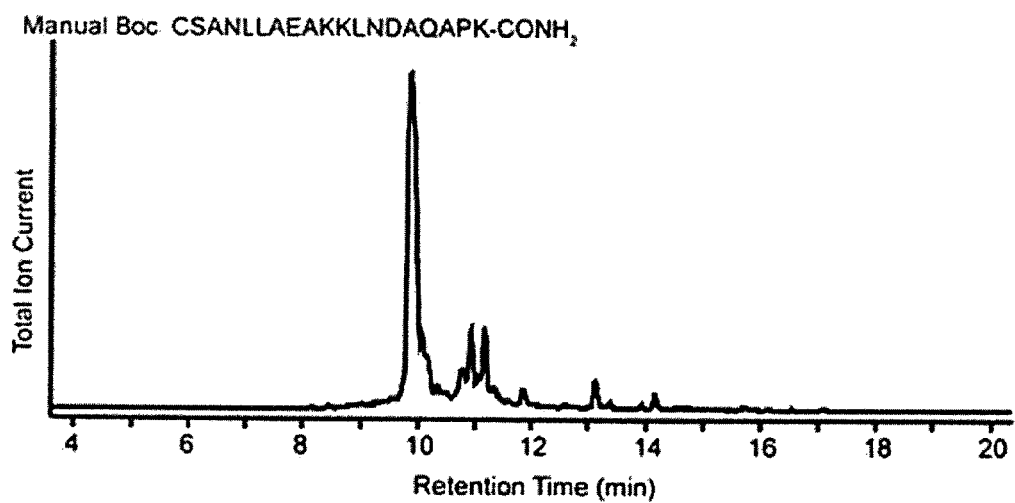
Figure 9A:
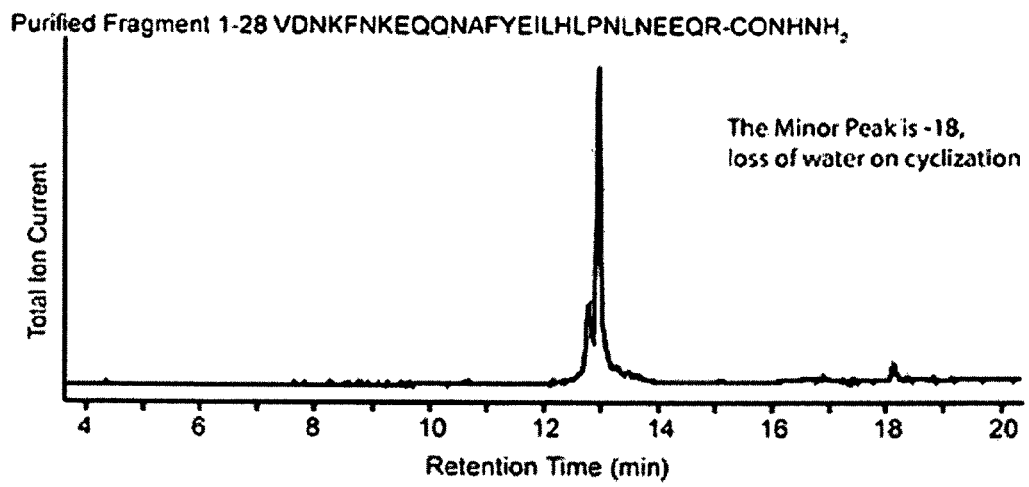
FIGS. 9A-9E are, according to certain embodiments, (A) a total ion chromatogram for a purified first affibody fragment (SEQ ID NO: 6), (B) a total ion chromatogram for a purified second affibody fragment (SEQ ID NO: 7), (C) a total ion chromatogram for a purified third affibody fragment (SEQ ID NO: 8), (D) a total ion chromatogram for the purified affibody fragment from the ligation of the first and second fragment (SEQ ID NO: 15), and (E) a chromatogram and mass spectrum for the purified affibody.
Figure 9B:
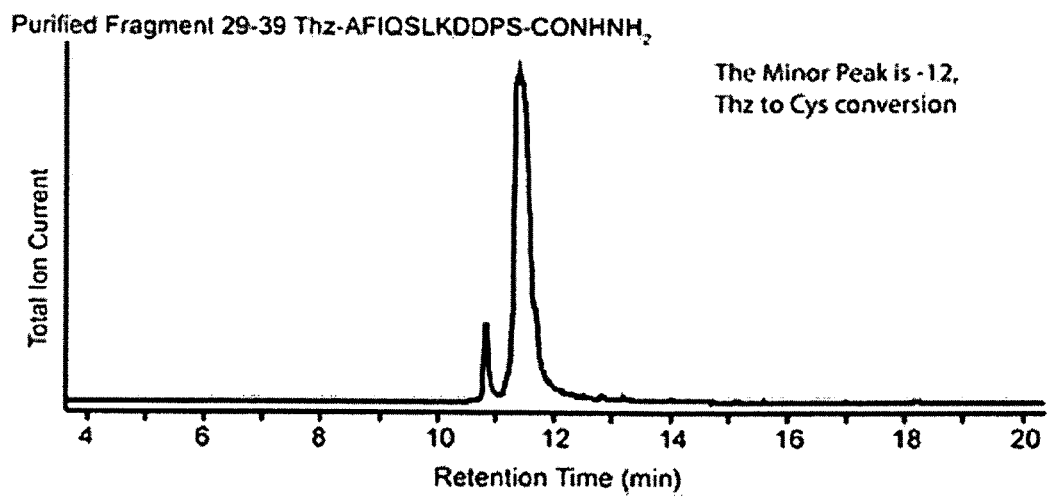
Figure 9C:
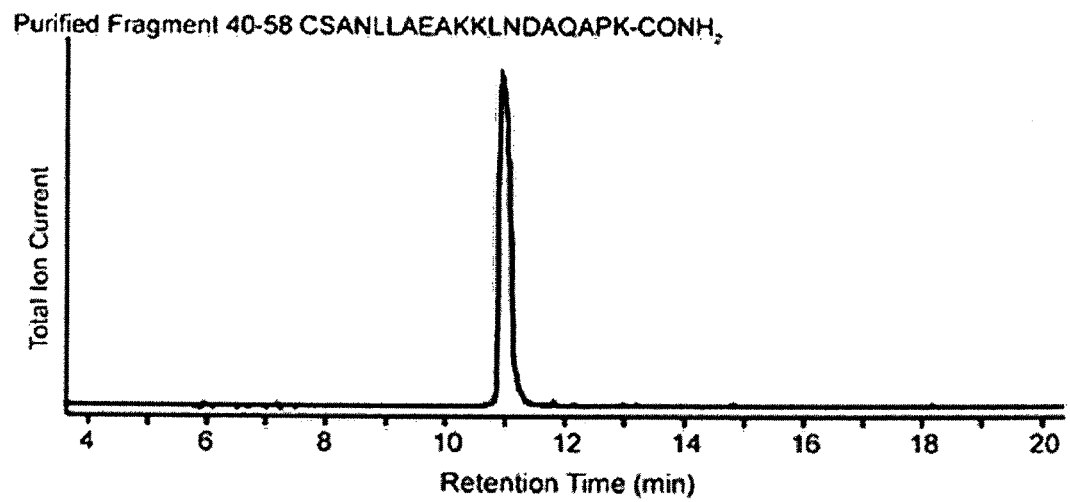
Figure 9D:
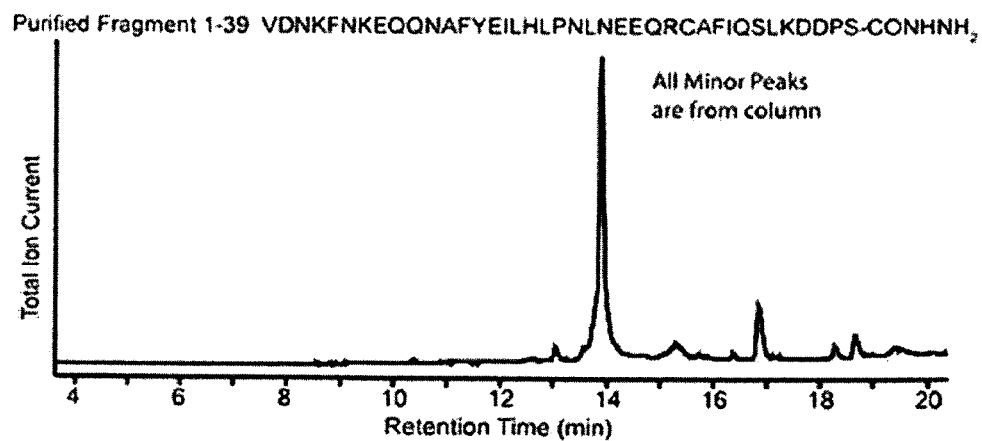
Figure 9E:
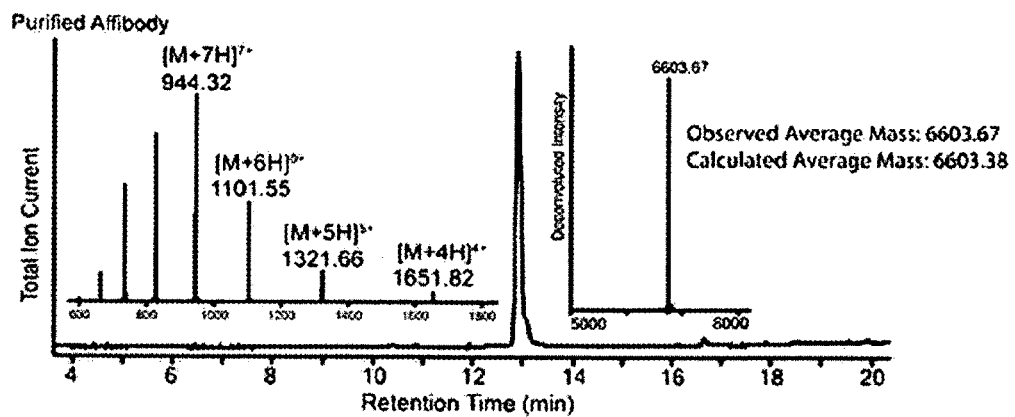

Using the modified coupling conditions for cysteine, the conotoxin variant and a fragment of the HIV-1 protease were prepared on a 0.1 mmol scale. Eighty nine milligrams (53%) of the crude conotoxin and 90 mg (43%) of the crude HIV-I protease fragment were isolated. To explore the utility of the flow platform in the preparation of synthetic proteins, a 58 residue tri-helical protein based on the Z domain of protein A (referred to as the affibody) was prepared. The synthetic strategy, which can be seen in FIG. 7A, used peptide-hydrazides as thioester precursors for use in native chemical ligation. Peptide hydrazides can be oxidized with $NaNO_2$ to form a C-terminal peptide-azide, which can react with a thiol to form a peptide thioester. The LCMS data for the crude synthetic peptides are shown in FIGS. 7B-D. Variants of these peptides were also prepared using Boc in-situ neutralization methods and the peptides were found to be of similar crude quality (FIGS. 8A-8F). Retention time shifts are due to different chromatographic conditions and slight variations in peptides prepared for native chemical ligation with Boc and Fmoc strategies. Each peptide for the affibody was purified (FIG. 9), the affibody was then synthesized, and the highly pure, full-length affibody was isolated after purification (FIG. 7E).

Although it was possible to implement this protocol in a batch mode, the flow based platform overcame a number of significant obstacles. First, the completely sealed reactor and a preheat loop were immersed in a temperature controlled bath which allowed reagents to be heated in a consistent and controlled manner immediately before reaching the resin bed. This would be difficult in some batch systems. Second, the use of a low volume reactor (about 2.5 mL) and narrow tubing for delivery of solvents and reagents allowed efficient washing with only 20 mL of solvent. In contrast, batch mode automated and manual syntheses typically use large volumes of solvent (about 70 mL per wash). Third, the flow platform was assembled from common laboratory equipment at low cost without machine or glass shop support. Fourth, high quality peptides were obtained quickly without double coupling, double deprotection, colorimetric tests, or resin mixing. During the studies with ACP (65-74), no decrease in the Val deletion peptide was observed after double coupling Val and double deprotecting the preceding Gln. These additional steps are often employed in batch mode syntheses. Finally, the flow based SPPS system was capable of being adapted to larger synthetic scales by increasing the diameter of the reactor. For example, the reactor diameter was doubled and the resulting reactor used to synthesize ACP (65-74) on a 0.2 mmol scale using exactly the same protocol. Another option for increasing the synthetic scale was to simply increase the reactor length. However, this strategy significantly increased the backpressure, which may pose difficulties during synthesis. The flow based SPPS platform in this example allowed for the rapid Fmoc synthesis of polypeptides. It was found that, under flow at 60° C., amide-bond formation and Fmoc removal were fast (within seconds) and did not improve with increased reaction time. Using the flow based Fmoc system in this example, three affibody segments were able to be synthesized and cleaved in one working day. By contrast, the production of similar peptides using optimized Boc in-situ neutralization methods, with 15 minute cycle times, required more than three days. In addition, the purified peptides were ligated to generate synthetic proteins. This approach allowed for the rapid production of highly pure, moderately sized peptides that were easily ligated to obtain larger fragments.

Example 2

This example describes the determination of the deprotection step time. Real-time monitoring of the effluent with an inline UV-Vis detector allowed the deprotection step to be reduced in length. The rate of Fmoc removal was investigated by monitoring the UV absorbance of the reactor effluent at 304 nm. To determine the minimum treatment time for robust Fmoc removal, the deprotection solution was flowed in at 10 mL/min for 60 seconds, 30 second, 15 seconds, or 6 seconds. Twenty seconds at 10 mL/min was found to be sufficient for complete Fmoc removal. Effective Fmoc removal was also achieved during the 6 second steps.

In developing a Nα deprotection protocol, piperidine in DMF was selected as the standard deblocking reagent. A concentration of 50% (v/v) in DMF was selected over the more common 20% (v/v) in DMF because the deprotection solution was diluted as it entered the column. A higher concentration was therefore desirable. The flow rate was set at 10 mL/min (maximum) to reach an effective concentration in the minimum time. To determine the length of the deprotection step, ALF peptide was synthesized with a double deprotection of every residue, and the UV absorbance of the effluent was monitored at 304 nm. Piperidine and DMF did not absorb well at this wavelength, but piperidine-DBF, the deprotection product, did. Therefore, the presence of a second peak after the second deprotection indicated that the initial deprotection was inadequate. No second peak was observed after 60 seconds, 30 seconds, and 15 seconds of deprotection, and only a very small peak was observed after a 6 second initial deprotection. In all cases, the first deprotection was at 10 mL/min, and the second was for one minute at 10 mL/min. Since Fmoc removal has been reported to be sequence dependent, a final deprotection time of 20 seconds was selected. However, it is believed that the 6 second deprotection step (and even faster deprotection steps) would be suitable for many peptide synthesis processes. Additionally, it is believed that, by increasing the flow rate of the deprotection agent and/or the temperature of the stream comprising the deprotection agent, robust Fmoc removal can be achieved in one second or less.

The double deprotection protocol had to be used to determine deprotection time because it took significantly longer to wash the piperidine-DBF adduct out of the resin than to remove the Nα Fmoc group. If the effluent was simply monitored until the absorbance returned to near-baseline, most of the "deprotection" time would have been spent washing the resin with deprotection reagent after the deprotection was complete.

Figure 10:
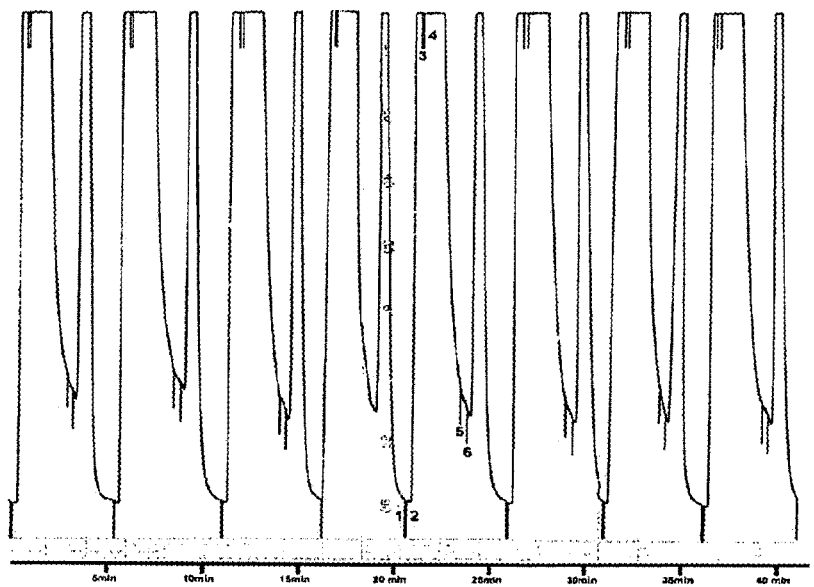
FIG. 10 is a plot of ultraviolet absorbance as a function of time recorded during the synthesis of a peptide, according to one set of embodiments.

FIG. 10 shows the UV record of the incorporation of the final eight residues during the conotoxin synthesis. Negative marks represent manual actions. The scanned trace has been color enhanced and a time-line added, taking zero to be the beginning of the trace. The marks of one cycle have been annotated with 1 indicating the end of the previous wash, 2 indicating the beginning of coupling, 3 indicating the end of coupling, 4 indicating the start of the first wash, 5 indicating the end of the first wash and start of the deprotection, and 6 indicating the end of the deprotection and start of the second wash. The quick connect was moved between 1 and 2, and between 3 and 4. Inconsistencies in cycle time and missing marks were due to human error.

Example 3

This example describes the determination of the wash step time. Real-time monitoring of the effluent with an inline UV-Vis detector allowed the wash step to be reduced in time. The efficiency of the wash step was systematically investigated by monitoring the UV absorbance of the reactor effluent at 304 nm. The time required to wash the amino acid out of the reactor as a function of flow-rate was then investigated. It was determined that the wash efficiency was principally determined by the total volume of solvent used, with about 16 mL of DMF required to remove 99% of the amino acid precursor. However, at flow rates greater than about 6 mL/min, marginally less solvent was required. It was concluded that a 2 minute DMF wash at 10 mL/min was sufficient. Double incorporation of amino acids, which could theoretically occur if the DMF wash did not completely remove the amino acid or deprotection solution, was not observed for the 2 minute wash time. Increasing the wash volume did not improve the crude peptide quality. It is believed that even faster wash times could be observed by, for example, increasing flow rate, changing the geometry of the inlet to reduce recirculation, and/or reducing the aspect ratio of the reactor. Without wishing to be bound by theory, it is further believed that, in some cases, there may not be an unacceptable decrease in crude peptide quality if the wash is reduced or eliminated. In some such cases, an amino acid addition cycle may be employed that does not remove substantially all of an activated amino acid prior to the deprotection step and/or does not remove substantially all of the deprotection reagent prior to the amino acid coupling step.

Figure 11:
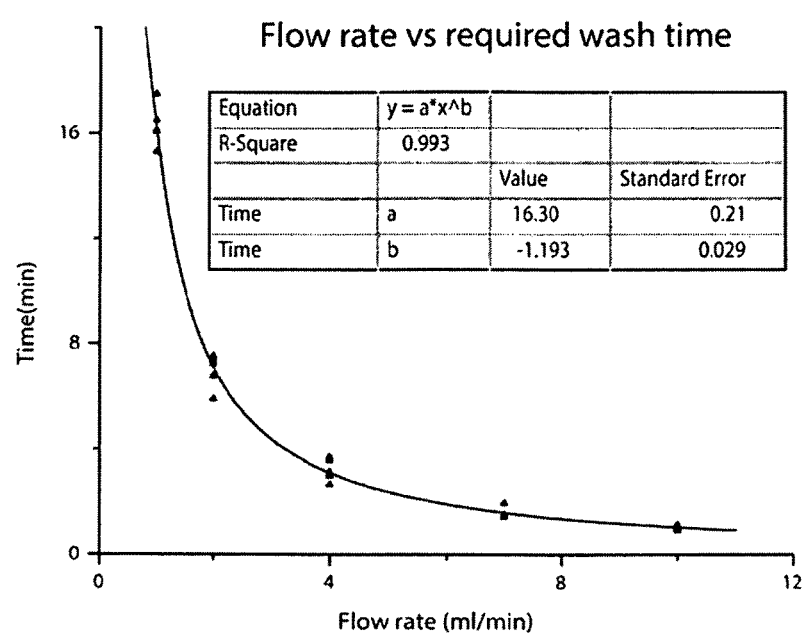
FIG. 11 is a graph of flow rate versus wash time, according to one set of embodiments.

Visual observation of the reactor during wash cycles showed recirculation and mixing of DMF wash solvent and coupling solution. Other solvent exchanges showed the same behavior. Differences in color and refractive indices allowed the direct observation of all exchanges. Based on these observations, it was expected that the wash efficiency was primarily dependent on the volume of solvent used, as predicted by a continuous dilution model. To test this theory, the UV absorbance of the reactor effluent was monitored at 304 nm during the triplicate synthesis of ACP (65-74). During each synthesis, two consecutive residues were washed at 10 mL/min, two at 7 mL/min, two at 4 mL/min, two at 2 mL/min, and the final two at 1 mL/min. Wash rates were randomly assigned to blocks of amino acids, ensuring that no block was washed at the same rate twice. The time required for the detector to desaturate was measured for each residue. Desaturation represents approximately 99% reduction in amino acid concentration. This wash efficiency was selected because the wash was essentially complete, but air and particulate contamination in the detector were less significant than at lower signal levels. The data are shown in FIG. 11. The exponent (parameter b) was significantly below negative one. The value of the exponent meant that less solvent was required to desaturate the detector at higher flow rates. The relationship between desaturation and flow rate was not consistent with the proposed continuous dilution model.

Based on these results, a maximum flow rate (10 mL/min) was selected for the wash. The wash time was set at two minutes, which reliably reduced the final concentration of coupling solution to 0.2% of the initial concentration. This trend is valid with wash rates up to at least 100 ml/min resulting in effective washing observed in 10 seconds. It is believed that even faster washing times could be achieved, for example, by increasing the wash liquid flow rate. No double incorporation, a possible outcome of an inadequate wash, was observed. The apparatus used did not provide a direct way to monitor the removal of piperidine (the UV absorbance is similar to DMF at accessible wavelengths), so the same wash cycle was used for the second wash. If it was assumed that piperidine is removed at the same rate as piperidine-DVB, the two minute wash was an overestimate of the necessary wash time as shown by the UV trace in FIG. 10. The total time of an amino acid addition cycle may be reduced by substantially reducing the washing step.

Example 4

This example describes the determination of minimum coupling time. The effect of coupling time was investigated by synthesizing two model peptides: LYRAG-CONH2 (SEQ ID NO: 2) and Fmoc-ALF-CONH2. For each of five amino acid addition cycles, every amino acid was coupled for a nominal time of 90 seconds, 45 seconds, 30 seconds, 15 seconds, or 7 seconds at 60° C. as shown in FIG. 3. For LYRAG-CONH2 (SEQ ID NO: 2), a significant increase in the Arg deletion peptide was observed when all residues were coupled for 7 seconds. For Fmoc-ALF-CONH2, no significant difference in the quality of the crude product as a function of coupling time was found. Based on these results, a 30 second coupling time was concluded to be sufficient.

It is generally known from the literature that, at room temperature, amide-bond formation is 99% complete in less than 100 seconds using HBTU as a coupling agent. If it was assumed that the reaction rate for this process doubled for every 10° C. increase in temperature, at 60° C. amide bond formation would be completed in about 6 seconds, which would have significantly decreased amino acid addition cycle time. Thus, all subsequent coupling studies were carried out at 60° C. to minimize the cycle time without significantly increasing formation of side products. An important feature of this platform was the ability to simply place the reactor and a preheat loop in a temperature controlled water bath. The preheat loop allowed reagents to be stored at room temperature and then immediately heated before entering the reactor, which allowed the thermal degradation of reagents to be minimized.

LYRAG (SEQ ID NO: 2) was selected as a model peptide to determine the minimum coupling time, because the arginine deletion could be monitored. For 90 seconds, 45 seconds, and 30 seconds nominal coupling times, the coupling solution was delivered at 4, 8, and 12 mL/min, respectively. This flow rate allowed the delivery of 2 mmol of amino acid. Flow rates above 12 mL/min were not reliably obtainable in this system (although other systems could be designed to include higher flow rates), so for the 15 second trial, half of the coupling solution was used (1 mmol amino acid in 2.5 mL 0.4M HBTU in DMF, with 0.5 mL N,N-Diisopropylethylamine (DIEA)). At a coupling time of 7 seconds, the time spent manually moving the quick connect (5-6 seconds) was very significant, so 1.2 mL of coupling solution was delivered. This volume was the volume of the preheat loop, so the coupling solution did not reach the reactor until it was cleared from the lines by the DMF wash. The wash, at 10 mL/min, took 7.2 seconds to clear 1.2 mL, giving a 7 second coupling time. In the other runs, the 5 seconds to move the quick connect was added to the nominal coupling time, as was the time required to deliver about a 10% increase over the nominal volume of coupling solution. The difference in the time taken for the DMF wash solvent and coupling solution to clear the inlet line was subtracted. More accurate coupling times were 93 seconds, 53 seconds, 39 seconds, 23 seconds, and 7 seconds. This does not include the time required to wash the coupling solution from the reactor. The seven second coupling showed increased Arginine deletion, so the 30 second protocol was selected as a conservative estimate. Fmoc-ALF was produced with the same procedure, and showed no change in peptide quality with reduction in coupling time. Data are presented in FIG. 3.

It is believed that using an automated system, using higher flow rates, and using a higher temperature would substantially reduce the coupling time.

Example 5

This example describes the minimization of cysteine racemization. The peptides PnlA (A10L) conotoxin, HIV-1 PR (81-99), and GCF were used to explore techniques to minimize cysteine racemization.

In the initial syntheses of PnlA (A10L) conotoxin and HIV-1 PR (81-99), cysteine was activated like all other amino acids (1 eq HBTU, 2.9 eq DIEA), and significant diastereotopic impurities were observed in the products. These were determined to be the result of cysteine racemization. To investigate conditions that reduce racemization, a model system, GCF, was selected because the diastereomer formed upon racemization was resolved by RP-HPLC. The standard synthetic procedure was used, except coupling time was increased to one minute for 60° C. runs and 6 minutes for room temperature (RT) runs. Rink, Gly, and Phe were all activated according to the standard procedure, with one equivalent of HBTU (5 mL, 0.4M) and 2.9 equivalents of DIEA (1 mL). For cysteine, various activation procedures were used as summarized below. For procedures that used less than 1 mL of DIEA, DMF was used to replace this volume. In addition to the activation methods below, an authentic diastereomer was produced using Fmoc-D-Cys (Trt)-OH and the activation procedure of 5. TIC traces are shown for 4, 5, 6, 7, and the authentic diastereomer in FIG. 6. Runs not shown were visually indistinguishable from 4. In all cases, the activator, additive, and 2 mmol amino acid were dissolved in 5 mL DMF, and additional DMF was added as needed. The base was added immediately before use. Reaction 8 employed an isolated C-terminal pentafluorophenyl (Pfp) ester (Fmoc-Cys(Trt)-OPfp) without additional activators, additives, or base. Table 1 summarizes the results, with racemization quantified by integration of the extracted ion current. This enables quantification of racemization below the TIC baseline. The results obtained were consistent with previous reports.

TABLE 1

Reaction conditions and racemization results.

| Reaction | Activator | Additive | Base | Temp | Racemization |
|---|---|---|---|---|---|
| 1 | HBTU (1 eq) | None | DIEA (2.9 eq) | 60° C. | 10% |
| 2 | HBTU (1 eq) | HOBt (1 eq) | DIEA (2.9 eq) | 60° C. | 18% |
| 3 | HBTU (1 eq) | None | DIEA (2.9 eq) | Cys room temp G and F 60° C. | 11% |
| 4 | HBTU (1 eq) | None | DIEA (2.9 eq) | Room temperature | 10% |
| 5 | HBTU (1 eq) | None | DIEA (0.9 eq) | 60° C. | 1% |
| 6 | HBTU (1 eq) | HOBt (1 eq) | DIEA (0.9 eq) | 60° C. | 1% |
| 7 | DCC (0.9 eq) | HOBt (1.1 eq) | None | 60° C. | 1% |
| 8 | OPfp | None | None | 60° C. | 1% |

FIGS. 6A-6E shows GCF produced with various cysteine activation schemes. The peak eluting between the desired product and diastereomer in A and B was hydrolysis of the C-terminal carboxamide. The diastereomer was barely visible. Conditions are listed in table 1. The conditions in FIG. 6A-D show chromatograms for reactions (a) 5, (b) 7, (c) 8, (d) 4, and the (e) the authentic Gly-D-Cys-L-Phe. The total ion current is displayed in each chromatogram.

Example 6

This example describes the synthesis of an affibody. Throughout this section, ligation buffer refers to a 6M GnHCl, 0.2M Sodium Phosphate buffer at the specified pH; buffer P is a 20 mM Tris, 150 mM NaCl solution at pH=7.5.

Oxidation chemistry was used to ligate three fragments into a synthetic, 58 residue protein. Thiozolidine was found to be unstable in the conditions used, so 9.6 mg of fragment Thz-[28-39]-CONHNH$_2$ was converted to a free N-terminal cysteine by treatment with 83 mg methoxyamine hydrochloride in 5 mL of ligation buffer at pH=4 overnight. Quantitative conversion was observed. The N-to-C assembly shown in FIG. 5A was employed instead of the C-to-N synthesis used when thioesters are accessed directly. Fragment [1-27]-CONHNH$_2$ was oxidized to the C-terminal azide by drop wise addition of 0.1 mL of 200 mM aqueous NaNO$_2$ to a solution of 11 mg purified fragment [1-27] CONHNH$_2$ in 1 mL ligation buffer at pH=3 and 0° C. The reaction proceeded for 20 minutes at 0° C., and was then quenched by the addition of 172 mg 4-mercaptophenylacetic acid (MPAA) and 34 mg tris(2-carboxyethyl)phosphine.HCl (TCEP.HCl) dissolved in 4.4 mL ligation buffer (pH=7, room temperature (RT)). To the resulting thioester, 3.4 mL of the crude methoxyamine treated fragment Thz-[28-39]-CONHNH$_2$ were added. After a two hour RT ligation, one half of the crude reaction mixture was purified by RP-HPLC, with 2 mg of highly pure material recovered. Of this, 0.6 mg were oxidized by dissolution in 0.1 mL of ligation buffer and drop wise addition of 0.01 mL of 200 mM aqueous NaNO$_2$ at 0° C. The reaction proceeded for 26 minutes, and was then quenched by addition of 3.1 mg MPAA and 0.78 mg TCEP.HCl dissolved in 0.1 mL ligation buffer (pH=7, RT). The pH was adjusted to 7 and 0.3 mg of fragment Cys-[40-58]-CONH$_2$ were added to the reaction mixture. After a two hour RT ligation, the mixture was diluted with 0.21 mL buffer P, then a further 0.63 mL buffer P to fold the resulting affibody. The crude mixture was concentrated over a 3 kDa membrane to a final volume of 0.075 mL. The crude, folded protein was diluted with 36 mg TCEP.HCl in 3 mL buffer P and purified to homogeneity (FIG. 9).

FIGS. 9A-9E show LC-MS chromatograms of the purified affibody synthesis intermediates and final product. FIGS. 9A-9E are chromatograms of (a) fragment [1-27] CONHNH$_2$, (b) fragment Thz-[28-39]-CONHNH$_2$, (c) fragment Cys-[40-58]-CONH$_2$, (d) ligation fragment [1-39]-CONHNH$_2$, and (e) the final affibody.

Comparative Example 6

This example describes the synthesis of an affibody using a conventional manual Boc in-situ neutralization method.

Comparable affibody fragments were synthesized using manual Boc in-situ neutralization methods. LC-MS data for these crude peptides is shown in FIGS. 8A-8F, next to the crude peptides synthesized on the flow based SPPS platform. In all cases, the quality was comparable. Retention time shifts are due to a change in chromatographic conditions and slightly different peptides prepared for ligation with Boc and Fmoc strategies.

Example 7

This example describes the design of the system used for flow based SPPS. Throughout this example the system is referred to as the synthesizer. A schematic of the synthesizer is shown in FIG. 2A. An HPLC pump was used to deliver either methanol purge solvent for washing the pump heads, reactor, and UV detector after use; DMF wash solvent for removal of reagents and byproducts during synthesis; or 50% (v/v) piperidine in DMF for deprotection of the N-terminus. The positions of valves 1 and 2 determined which fluid was delivered. A syringe pump was used to deliver coupling solution. To switch between the syringe pump and HPLC pump, a quick connect was manually moved from the outlet of the HPLC pump to the syringe on the syringe pump.

A valve would have been generally ineffective because the line between the syringe pump and valve would retain coupling solution, causing incorrect incorporation in the next cycle. The column and a 1.2 mL preheat loop (not shown) were submerged in a water bath to maintain a constant 60° C. Valves 3 and 4 selected a high pressure bypass loop used to clear the UV detector when it was clogged with precipitates, such as the urea byproduct of DCC activation encountered during cysteine racemization studies. The loop was also used to purge the detector without the column in line.

A Varian Prostar 210 HPLC pump, KD Scientific KDS200 syringe pump, Varian Prostar 320 UV detector set to 304 nm, Amersham Pharmacia Biotech chart recorder, and VWR 39032-214 water bath were used in the synthesizer. The HPLC pump delivered about 95% of the nominal flow rate. Disposable 10 mL syringes (BD 309604) were used to deliver coupling solutions. Valve 1 was a Swagelok ⅛" 3-way valve (55-41GXS2). The other valves in the system were Swagelok 1/16" 3-way valves (SS-41GXS1). The methanol, DMF, and 50% (v/v) piperidine lines through valve 1 up to valve 2 were ⅛" OD, 1/16" ID FEP (Idex 1521). The line between valve 3 and 4 was 1/16" OD, 0.010" ID peek (Idex 1531). All other lines were 1/16" OD, 0.030" ID PFA (Idex 1514L). To attach the ⅛" wash and deprotect lines to the 1/16" inlets of valve 2, Swagelok ⅛" to 1/16" (SS-200-6-1) reducing unions were used, followed by a short section of 1/16" tubing. All lengths were minimal, except the tubing between the quick connect and the reactor. This included a 2.6 m (1.2 mL) coil which was submerged along with the reactor and served as a preheating loop to ensure that reactants were at 60° C. before reaching the reactor. Whenever tubing had to be joined, Swagelok 1/16" unions were used (SS-100-6). These were used to attach the preheat loop, join the outlet of the column to a line from valve 4, and repair a severed bypass loop. The manually changed quick connect was a female luer to 10-32 female HPLC fitting (Idex P-659). This connected directly to the syringes on the syringe pump or to a mating male luer to 10-32 female fitting on the line from valve 3 (Idex P-656). The connection between the UV detector and chart recorder was a data link (three 18 ga insulated copper wires).

FIG. 2B shows the reactor assembly. The reactor consisted of a tube with standard compression fittings on each end (⅜" to 1/16" reducing unions). On the downstream end there was also a frit. This was positioned by a support designed to fit inside the reactor and seat against the bottom of the fitting on that end. Various frit porosities were used. The part number below was for a 20 micron frit, the most commonly used. The body was a 3.5 inch segment of PFA tubing with outer diameter ⅜" and inner diameter ¼". The frit was a ¼ "sintered stainless steel disk 1/16" thick. The frit support was a 0.5" length of ¼ "OD PTFE tubing. As the fittings were tightened, the nut compressed the ferrule against the fitting body, sealing the reactor body to the fitting body. This also compressed the reactor body against the frit, forming an internal seal against the frit. The reactor body and frit were purchased from McMaster-Carr as part numbers S1805K73 and 94461314, respectively. The nut, ferrule, and fitting body are available as a set with the 1/16" nut and ferrule from Swagelok as part number SS-600-6-1. Replacement ferrules are available as SS-600-SET. The reactor was assembled by first cutting the body and frit support to length, ensuring the ends were square. A sharp razor blade and steady hand were used for these operations. Next, the outlet (downstream) end was assembled. The frit was placed on a solid, clean surface and the reactor body was pressed onto it. After verifying that the frit was square and flush with the end of the reactor, the frit support was pushed in slightly, pushing the frit up towards its final position. Firmly seating the reactor body in the fitting body forced the frit to its final position. It was verified that the frit was square and properly positioned under the ferrule, then the fitting was installed according to the manufacturer's instructions. Once sealed, the frit could not be removed and reseated. Finally, the inlet fitting was installed according to the manufacturer's instructions. A high pressure reactor with a stainless steel body was also built. In this case, the downstream fitting had to be tightened well beyond specification to affect a seal with the frit. The reactor was typically replaced every 3-8 syntheses. When replacing the reactor, the ferrules, frit and reactor body were not reused. All other parts were reused. The nuts were recovered by cutting the reactor body in half.

To load the reactor, the upstream fitting body was removed and a slurry of resin in methanol was pipetted in. The reactor was completely filled with methanol, and the fitting body was reinstalled. The inlet line and preheat loop were filled with solvent by attaching them to the quick connect and running the HPLC pump before attaching them to the reactor. The reactor was then kept upright in the water bath so that any small bubble would move to the top and not interfere with wetting the resin. Before the first coupling, the resin was washed for two minutes with DMF at 10 ml/min.

Example 8

This example describes the design of a large-scale reactor, used for flow based SPPS in Examples 10-11 and 13-17 that allowed faster cycle times and increased synthetic scale. Throughout the examples, this reactor is referred to as the "second generation" reactor, in contrast to the "first generation" reactor described in Example 7.

Figure 12:
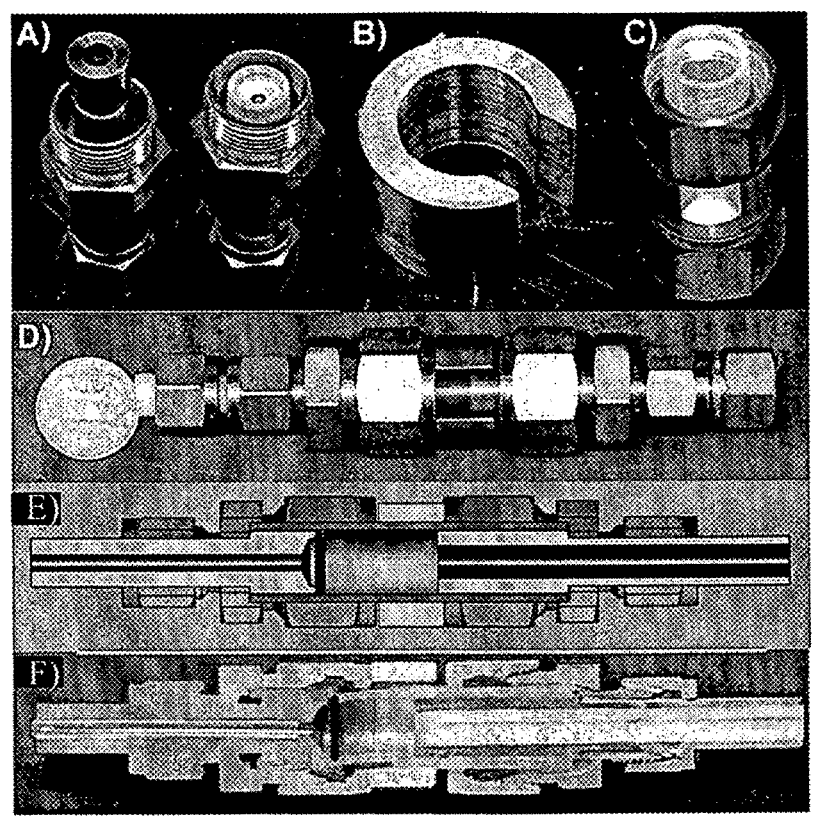
FIGS. 12A-G are, according to one set of embodiments, (A) a photograph of an inlet (left) and outlet (right), (B) a photograph of a spacer, (C) a photograph of a reactor body unit, (D) a photograph of an assembled reactor, and (E) a schematic of the reactor showing the reactor body, frit, and spacer, (F) a cutaway of a reactor, and (G) a synthetic timeline used with a reactor.
Figure 12:
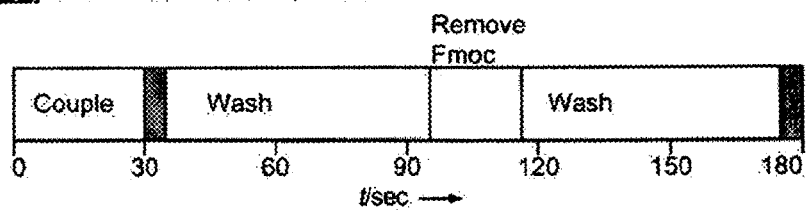

FIG. 12 shows the larger reactor. The design principles of the small-scale reactor (i.e. the first generation reactor) used for all syntheses in Examples 1-7 translated directly to larger scales. In order to preserve comparable cycles, however, the volume of the reactor had to be constant. Two problems were encountered when scaling up to a ⅝" OD, ½" ID tube. First, there were no standard ⅝" to 1/16" compression fittings. Second, the minimum distance between ⅝" fittings is quite large, meaning there is a large minimum volume. To overcome the first problem, a ⅝" to ⅜" fitting followed by a ⅜" to 1/16" fitting was used, but this necessitated a joining length of ⅜" tubing that greatly increased the already large volume of the reactor.

To reduce the reactor volume, a 316SS insert was machined that consisted of a nominal ½" OD segment followed by a ⅜" OD segment with a ¼" through hole. A ⅝" to ⅜" reducing union was bored out to give a ⅜" through hole, the insert was seated, and the ⅜" ferrule swaged on. After this, the insert could not be separated from the fitting. When installed, the ½" part of this insert-fitting sat in the top of the reactor and limited the volume.

This was effective, but there was still a large volume from the ¼" through hole. This volume was reduced by inserting a ¼" OD, ⅛" ID PFA tube and cutting it flush. To further reduce the volume, a ⅛" OD, 1/16" ID PFA tube was inserted by heating and drawing a section of tubing to a narrower diameter, threading it through, and pulling until all tubing in the insert was of the proper diameter. Both sides of the tube were cut flush and the drawn section was discarded. A ⅜" to 1/16" reducing union was installed on the open end of the ⅜" segment to interface with the rest of the system. This insert-fitting is pictured in FIG. 12A (left). To prevent the upstream insert fitting from becoming permanently sealed into the tube like the frit, the nominal ½" segment was machined to 0.496" and polished.

A similar piece was machined for the outlet side, with a ½" section the proper length to seat the frit under the ferrule. To prevent all of the solvent from being forced through a small central section of the frit, a ⅜" diameter step 0.05" deep was cut. The bottom of this step tapered to a ⅛" through hole at 31 degrees from horizontal (a standard drill bit taper). A ⅛" OD, 1/16" ID PFA tube was inserted to further limit the volume. The ½" section of the outlet insert positioned the frit and sat largely below the ferrule, so a standard finish was adequate. The one pictured in FIG. 12A was PTFE, and was installed in a bored through ⅝" to ⅜" reducing union in exactly the same way as the upstream insert. Subsequent reactors, including the one in the cutaway pictured in FIG. 12F, used stainless steel outlet inserts. A ⅜" to 1/16" reducing union was installed on the open end of the ⅜" segment to interface with the rest of the system.

Tubing was used to limit the internal volume of the inserts, rather than directly making inserts with small holes, to simplify fabrication.

To assemble the reactor, the frit was pressed in and the downstream insert-fitting installed as a regular fitting. The upstream insert-fitting was then installed as a regular fitting. Despite cutting it undersize and polishing, the upstream inset-fitting was very tight and difficult to remove. For subsequent reactors, an aluminum spacer, shown in FIG. 12B, was used to allow the reactor to have a consistent volume. The spacer set the internal volume to 2 mL and enabled reproducible assembly of the reactor. Furthermore, the spacer helped remove the inlet insert-fitting after synthesis. The spacer prevented the nut from moving down, and instead ejected the insert-fitting when the nut was turned. A vertical window was added to the spacer to maintain adequate optical access. A picture of the assembled large reactor is shown in FIG. 12D.

To load the reactor, the inlet insert-fitting was removed, the resin was added dry, and the reactor filled with methanol. The inlet insert-fitting was then attached to the heat exchanger and purged with methanol. Without removing it from the heat exchanger, the purged inlet insert-fitting was installed, causing excess methanol to exit the reactor through the outlet insert-fitting. If there was a large bubble, the reactor was turned upside down (with the inlet below the outlet) and purged. If this failed to dislodge the bubble, the reactor was disassembled and the loading procedure was repeated. To remove the resin after synthesis, a syringe filled with 10 mL of air was attached to the luer-lock quick connect on the heat exchanger inlet (where reagent syringes are attached) and used to deliver the air. This removed solvent from the heat exchanger, reactor, and waste line. The heat exchanger and waste line were then disconnected from the reactor and the inlet insert-fitting removed. The resin was suspended in DCM and decanted into a fritted syringe (Toviq), washed four times with DCM, and either cleaved immediately or dried under reduced pressure for storage.

Example 9

This example describes techniques used to reduce pressure in the first generation reactor. Pressure drop was inherently caused by the resin. Pressure drop was overcome by employing a rest period after high pressure flows or using a large reactor.

A low pressure polymer reactor was used, so an overpressure alarm on the HPLC pump was set to shut off the pump at 240 psi, which was occasionally triggered. When the alarm was triggered, the system was allowed to rest for 30 seconds, and the pumps were restarted without further incident. During this resting phase, the resin visibly expanded. By observing the HPLC pump pressure, it was concluded that if too much pressure was applied to the beads, they begin to compact. This increased the pressure drop across the bed, and the rate of compaction, which quickly triggers the over pressure alarm. Similar 1% divinyl benzene crosslinked polystyrene resin available for gel permeation chromatography from Bio-Rad was recommended for gravity driven separations only, because it is very soft once swollen.

When the reactor was disassembled immediately after such an event, the resin looked like a solid block and, when probed with a pipette tip, felt like a hard mass. It was difficult to immediately pipette it out. After a few tens of seconds, the resin relaxed and could be pipetted out. A high pressure stainless steel reactor was built and tested, but the very high pressure necessary to maintain a high flow through a compacted bed (>1000 psi) was reminiscent of previous continuous flow SPPS that struggled with extrusion of the resin through the frit.

It was believed that the initial compaction took place at the boundary of the frit and the resin, such that the resin was able to mechanically block the pores of a course frit with relatively little deformation. To test this theory, the original 40 micron frit was replaced with a 20 micron frit, and, in more limited trials, 10 micron frits and 2 micron frits. Smaller pores did not eliminate the problem, but seemed to qualitatively reduce its severity. From this it was concluded that the problem was inherent in the resin, and can only be eliminated by running at lower flow rates or reducing the bed height (using smaller scales and/or larger reactors).

The use of harder, more highly crosslinked resin has been reported, but the resulting peptides were of inferior quality. The solution used here was to wait 30 seconds following a high pressure event. This was effective and expedient, allowing progress on a reasonable scale without further optimizing the dimensions of the reactor. Trials with a ½" ID reactor (described in Example 8) showed no overpressure with up to 200 mg of resin, operating on the same cycle.

To overcome these problems, accelerate synthesis, and increase synthetic scale, the large scale reactor described in example 8 was constructed.

Example 10

This example describes the preparation of ALFALFA-CONHNH$_2$ (SEQ ID NO: 48) in six minutes. A high capacity pump head for the HPLC pump used in previous examples was used to deliver 100 ml/min of DMF during the wash step, 100 ml/min of 50% piperidine in DMF during the deprotection step, and 12 ml/min of activated amino acids during the coupling step. The reactor and preheat loop were maintained at 60° C. by immersion in a water bath.

Figure 13:
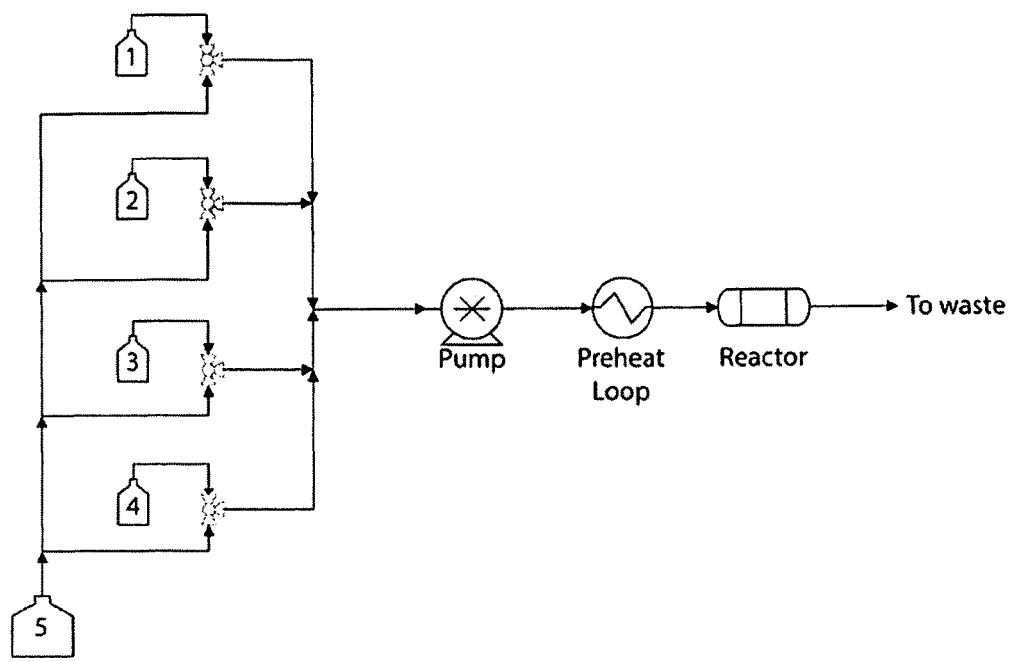
FIG. 13 is a schematic illustration of an exemplary system for performing peptide synthesis, according to one set of embodiments.

The apparatus shown in FIG. 13 was constructed. Reservoir 1 contained activated alanine, reservoir 2 contained activated leucine, reservoir three contained activated phenylalanine, reservoir 4 contained 50% piperidine in DMF, and reservoir 5 contained DMF. Each activated amino acid was prepared by combining 50 ml of 0.4M HBTU in DMF with 20 mmol Fmoc protected amino acid. Immediately before the start of the run, 10 mL of DIEA was added to each of the amino acid reservoirs. To obtain the desired flow rates, 1.5 bars of nitrogen head pressure was applied to each reservoir. All tubing upstream of the pump was 1/8" OD, 1/16" ID PFA. The three way valves were Swagelok 1/8" three way valves. The common lines of three way valves were routed into a switching valve (Valco C25-6180) which selected between the reagents. All valves were manually controlled. The pump was a Varian Prostar 210 with a 100 ml/min pump head. The preheat loop was 1.8 m of 1/16" OD, 0.030" ID PFA tubing. The reactor used was the larger reactor shown in FIG. 12 and described in Example 8. The reactor contained 120 mg of chlorotrityl hydrazide functionalized polystyrene resin, prepared from commercial chlorotrityl chloride resin using standard methods known to those of ordinary skill in the art. Using the larger reactor helped in maintaining a manageable pressure drop at 100 ml/min.

Figure 14:
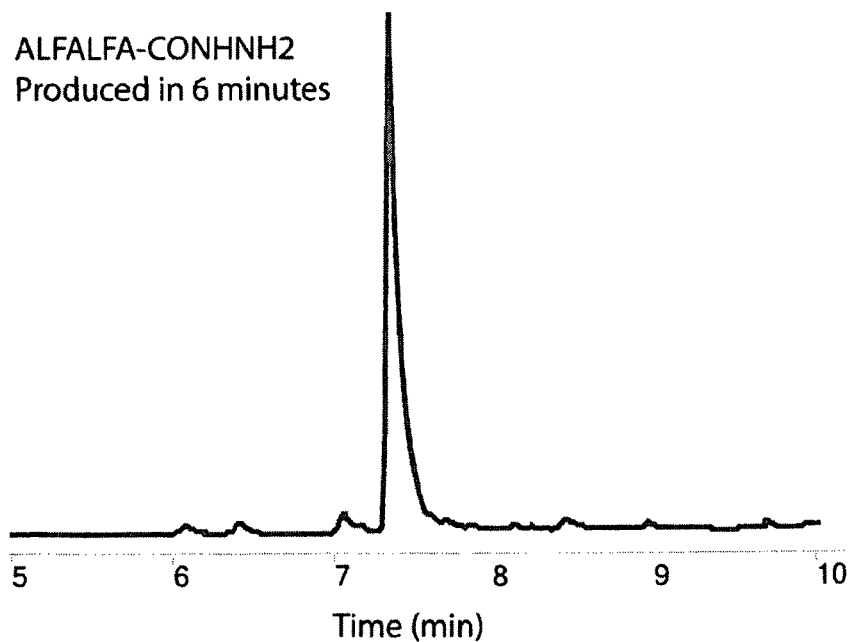
FIG. 14 is, according to certain embodiments, an exemplary total ion chromatogram of a synthesized peptide ALFALFA-CONHNH$_2$ (SEQ ID NO: 48)

One synthetic cycle was performed as follows. First a 20 second coupling was performed at 12 ml/min. The multiport valve was set to the desired amino acid and the three way valve was set to amino acid. All other three way valves were set to DMF. After twenty seconds, the selected three way valve was switched from amino acid to DMF and the pump flow rate was set to 100 ml/min. After five seconds, the multiport valve was switched to piperidine. After another five seconds, the selected three way valve was switched from DMF to piperidine. After 10 seconds the selected three way valve was switched back to DMF. After five seconds, the multiport valve was moved to the next desired amino acid. After another five seconds, the flow rate was reduced to 12 ml/min and the selected three way valve was switched from DMF to the next desired amino acid, starting the next cycle. The total time for each step was as follows: 20 second coupling, 10 second wash, 10 second deprotection, and 10 second wash. The total time for each cycle was 50 seconds. The total ion chromatogram from the LC-MS analysis of the crude material is shown in FIG. 14.

All of the above-listed times are believed to be conservative estimates of what would be required to achieve 99%+ yields. It is now known that at a flow rate of 20 ml/min the deprotection is finished in 5 seconds, and it is expected that at 100 ml/min the deprotection requires substantially less than 5 seconds. Longer peptides, such as the common model peptide ACP (65-74), could be prepared, for example, by integrating additional 3-way valves. The general strategy described in this example is expected to be viable for the production of any peptide, including those produced using the cycles described in Example 1.

Example 11

This example describes an improved synthesis scheme, in which the synthesis times (relative to Example 1) were substantially reduced. The cycle time for the synthesis in this example was less than 3 minutes. To reduce the cycle time relative to Example 1, the wash step was adjusted. All tubing upstream of the pump was replaced with 1/8" OD 1/16" ID PFA, and the two valves upstream of the pump were replaced with 1/8" Swagelok three way valves. All tubing lengths except the preheat loop were minimal, and the reactor described in Example 8 was used. All other system components were substantially unchanged relative to Example 1. Unless explicitly mentioned below, all procedures remained the same, relative to Example 1.

The larger tubing and a high capacity pump head (maximum 50 ml/min) were used to deliver DMF and deprotection reagent at 20 ml/min. As expected based on FIG. 11, a one minute wash at 20 ml/min proved to be adequate in all cases. Furthermore, a 5 second deprotection step was found to be adequate at these flow rates. The coupling step was unchanged. This yielded a total cycle time of 2 minutes 35 seconds to about 2 minutes and 50 seconds, depending on the speed with which the manual steps are performed. The wash was set at 20 ml/min instead of the maximal 50 ml/min because most users have difficulty manually operating the system at the higher flow rate. It is expected that automation can be used to overcome this human limitation and allow for the implementation of cycles of about 10 seconds per residue with sufficiently large pumps.

Figure 15:
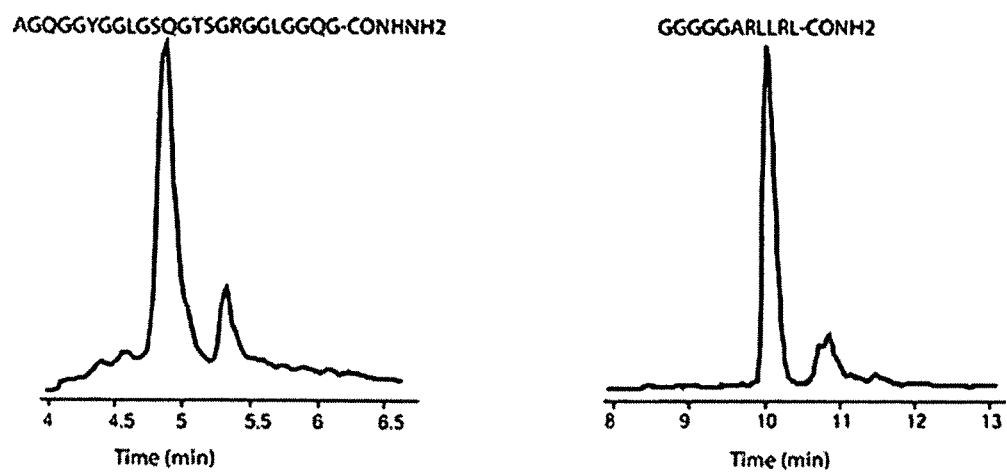
FIG. 15 shows two exemplary chromatograms of peptides made using certain of the peptide synthesis systems described herein (sequences from left to right correspond to SEQ ID NOs.: 16 to 17, respectively)
Figure 16:
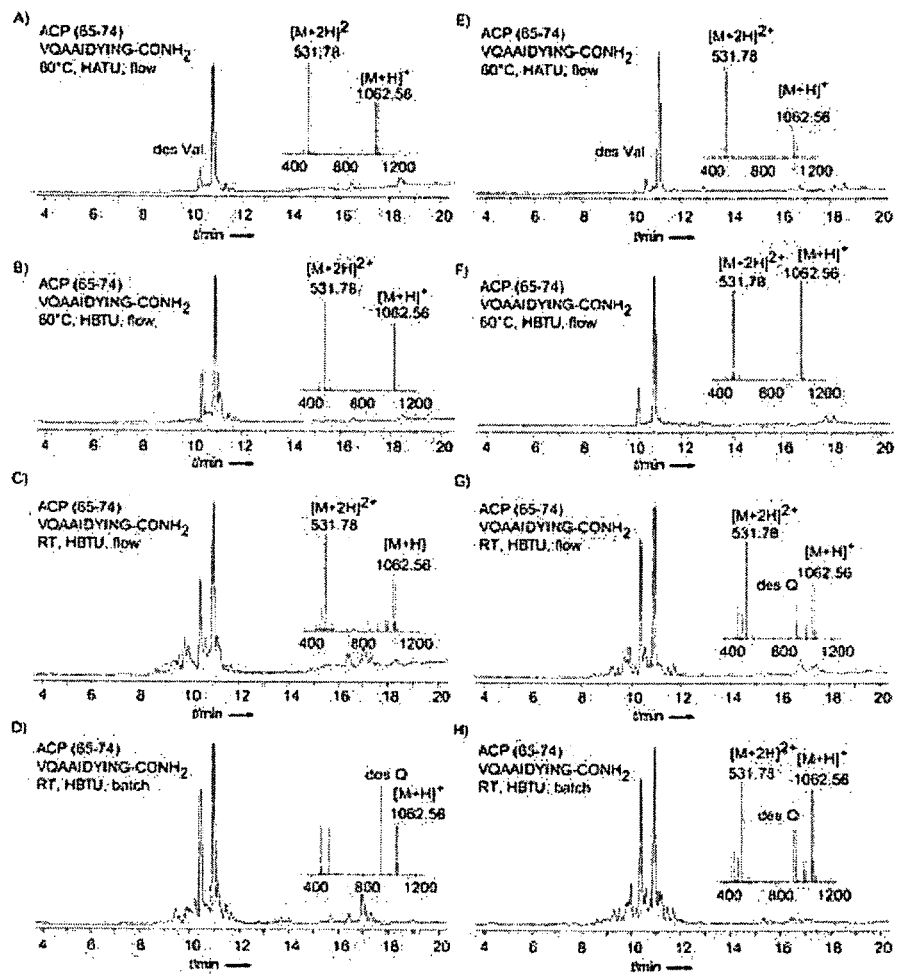
FIGS. 16A-H are, according to one set on embodiments, crude LCMS chromatograms for ACP (65-74) (SEQ ID NO: 3) synthesized with a second generation protocol at (A) 60° C. using HATU, (B) 60° C. using HBTU, (C) room temperature using HBTU, and (D) room temperature using a comparable manual batch method, and ACP (65-74) synthesized with a first generation protocol at (E) 60° C. using HATU, (F) 60° C. using HBTU, (G) room temperature using HBTU, and (H) room temperature using a comparable manual batch method.

Two chromatograms of peptides made using this cycle are shown in FIG. 15. In each case the main peak is the desired product. These are typical results for peptides of this length.

Example 12

This example describes in more detail the materials used in Examples 1-11 and 13-18 and the methods used in Examples 1-11.

2-(1H-Benzotriazol-1-yl)-1,1,3,3-tetramethyluronium hexafluorophosphate (HBTU), 2-(7-Aza-1Hbenzotriazole-1-yl)-1,1,3,3-tetramethyluronium hexafluorophosphate (HATU), hydroxybenzotriazole (HOBT), and Nα-Fmoc protected amino acids were from Chem-Impex International, IL, NovaBioChem, Darmstadt, Germany, and Peptide Institute, Japan. 4-methylbenzhydrylamine functionalized crosslinked polystyrene (MBHA resin) and p-Benzyloxybenzyl alcohol functionalized crosslinked polystyrene (Wang resin) were from Anaspec, CA. N,N-Dimethylformamide (DMF), dichloromethane (DCM), diethyl ether, methanol (MeOH) and HPLC-grade acetonitrile were from VWR, PA. Triisopropyl silane (TIPS) and 1,2 Ethanedithiol were from Alfa Aeser, MA. Trifluoroacetic acid (TFA) was purchased from NuGenTec, CA, Halocarbon, NJ, and Sigma-Aldrich, MO. Solvents for LC-MS were purchased from T J Baker and Fluka. All other reagents were purchased from Sigma-Aldrich, MO.

Common solvent mixtures used throughout these experiments were: 0.1% (v/v) TFA in water (A), 0.1% (v/v) Formic acid in water (A'), 0.1% (v/v) TFA in acetonitrile (B), and 0.1% (v/v) formic acid in acetonitrile (B').

Figure 4A:
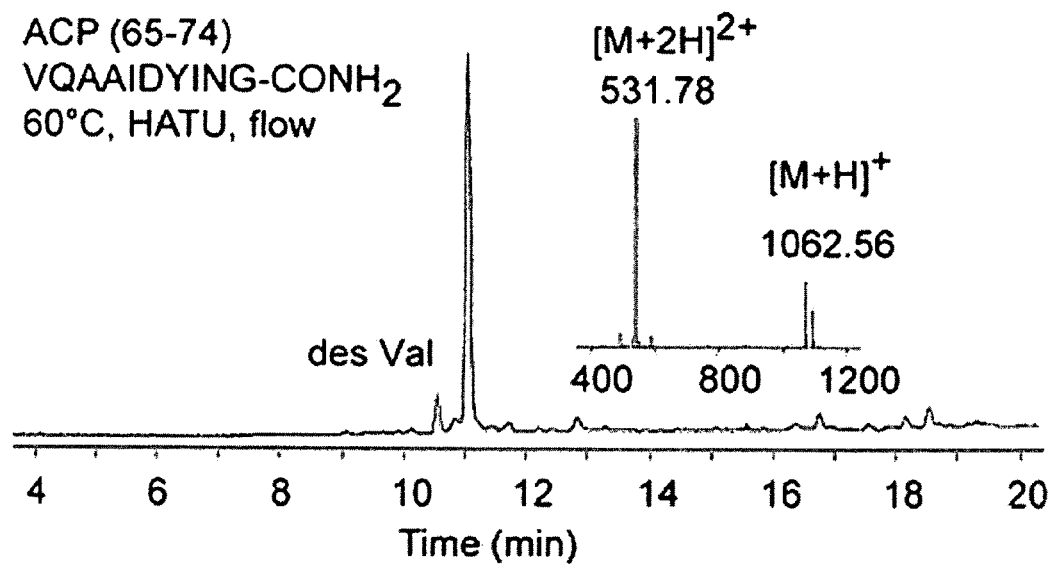
FIGS. 4A-4D are, according to certain embodiments, chromatograms and mass spectra for ACP (65-74) peptides (SEQ ID NO: 3) (A) synthesized using HATU at 60° C. and (B) synthesized using HBTU at 60° C., (C) synthesized using HBTU at RT and (D) synthesized using HBTU under batch conditions using the same synthetic timeline.
Figure 4B:
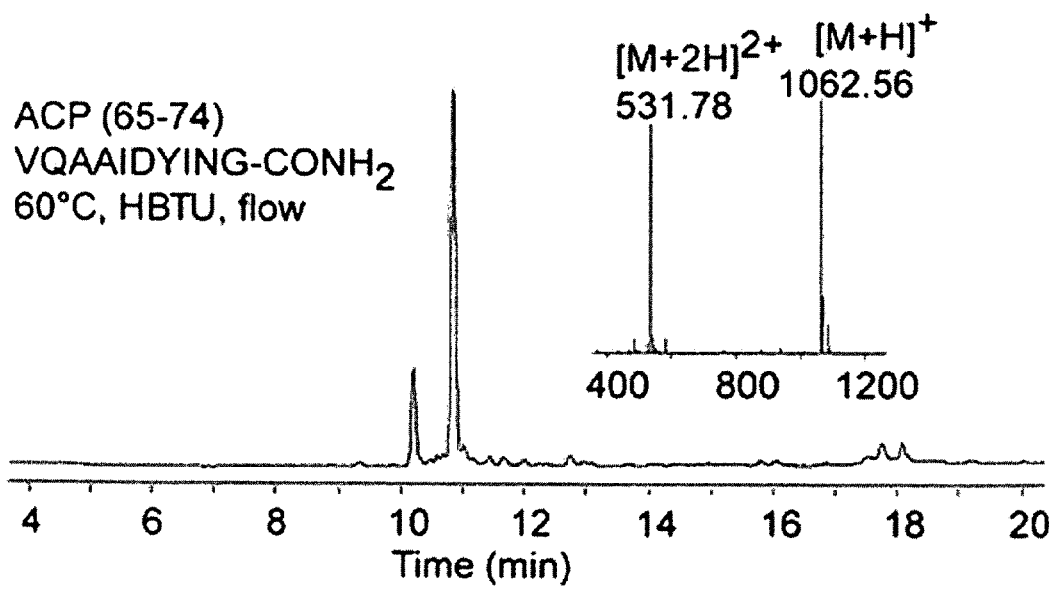
Figure 4C:
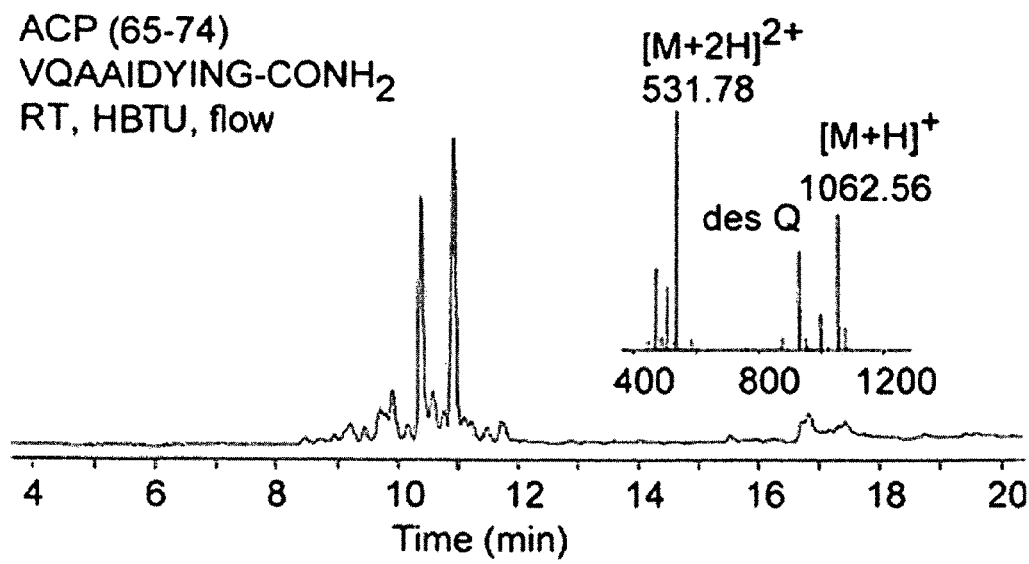
Figure 4D:
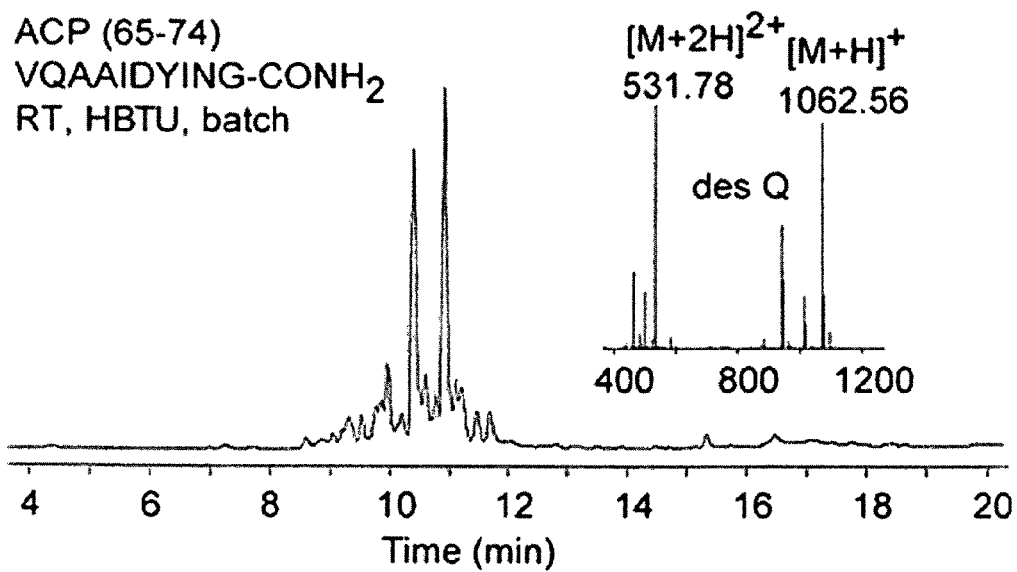
Figure 6A:
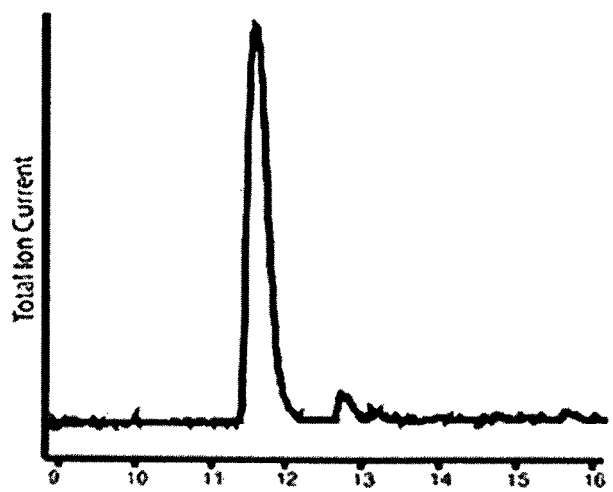
FIGS. 6A-6E are, according to certain embodiments, total ion current chromatographs for GCF peptides synthesized under various conditions (A) 5, (B) 7, (C) 8, and (D) 4, as shown Table 1, and (E) is an exemplary total ion current chromatograph for an authentic Gly-D-Cys-L-Phe sample.
Figure 6B:
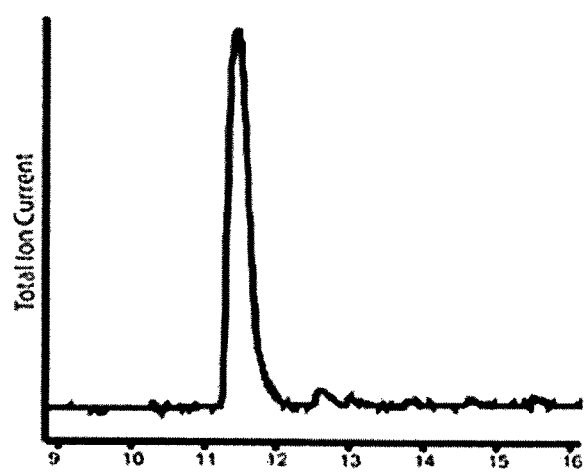
Figure 6C:
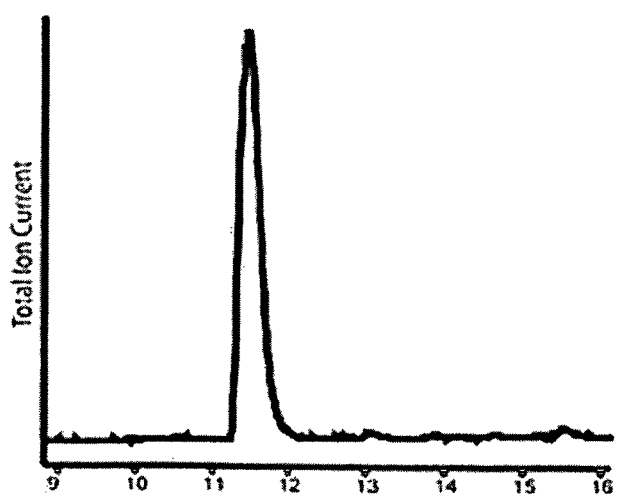
Figure 6D:
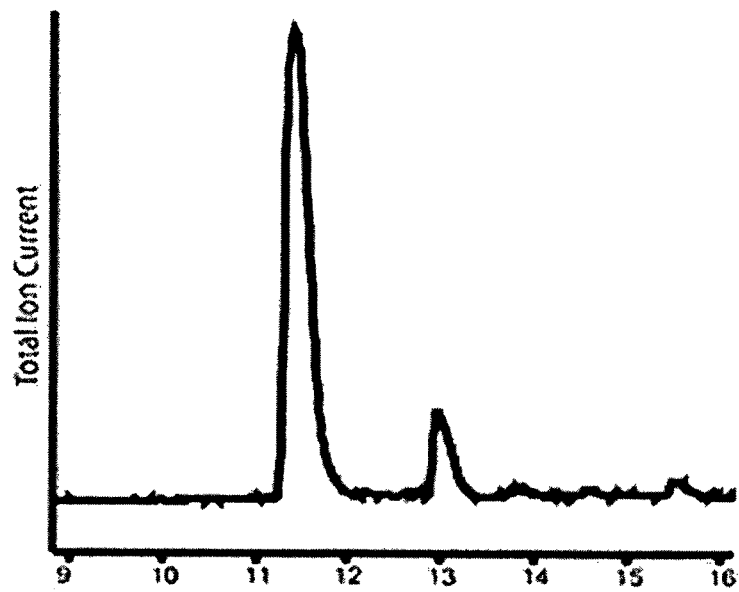
Figure 6E:
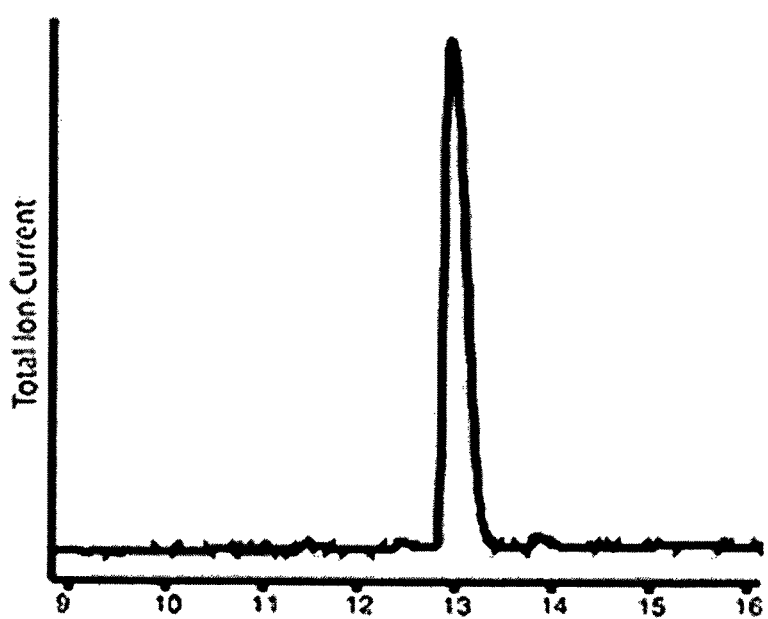

All peptides except the ACP (65-74) batch in FIG. 4D were synthesized on the flow based SPPS system. All peptides except ACP (65-74) batch and ACP (65-74) flow RT in FIGS. 4D and 4C were synthesized at 60° C., with reagents preheated immediately before use via a preheat loop (see synthesizer design). One synthetic cycle consisted of an amino acid exposure step (e.g., amide bond formation, also referred to as coupling in the examples), an amino acid removal step (e.g., removal of the coupling reagent, also referred to as a wash step in the examples), a deprotection agent exposure step (e.g., Nα Fmoc removal, also referred to as deprotection in the examples), and a deprotection agent removal step (e.g., removal of deprotection reagent and reaction product, piperidine-dibenzofulvene (piperidine-DBF), also referred to as a wash in the examples).

Unless noted, coupling was performed by delivering the following coupling solution at 12 ml/min (for approximately 30 seconds) in Examples 1-7. The activated coupling solution consisted of 2 mmol of Nα-Fmoc and side chain protected amino acid dissolved in 5 ml of 0.4M HBTU in DMF and 1 mL of DIEA. Cysteine was dissolved in 5 mL 0.4M HBTU in DMF, 0.687 mL neat DMF, and 0.313 mL DIEA. In both cases, amino acids were dissolved in HBTU solution up to several hours before use, and DIEA was added within two minutes of use. Volumetric measurements were made at RT (20° C.). The ACP (65-74) shown in FIG. 4A was synthesized by substituting HATU for HBTU in the above solution.

Next, the coupling solution was removed with 20 mL of DMF delivered at 10 mL/min over 2 minutes, and then the Nα-Fmoc protection group was removed with 3.3 mL of 50% (v/v) piperidine in DMF delivered at 10 mL/min over 20 seconds. Excess piperidine and piperidine-DBF were removed with 20 mL of DMF delivered at 10 ml/min over 2 minutes to complete one cycle.

All peptides were synthesized on 100 mg of 1% divinyl benzene crosslinked polystyrene resin. To produce C-terminal carboxamide peptides, MBHA functionalized resin with a loading of 1 mmol per gram was used, and the first residue coupled was the TFA labile Rink linker. To produce C-terminal hydrazide peptides for ligation, Wang resin, functionalized as below, was used. The loading was 0.6 mmol/g (0.06 mmol scale).

Non-cysteine containing carboxamide peptides were cleaved from the resin and side-chain deprotected by treatment with 2.5% (v/v) water and 2.5% (v/v) TIPS in TFA for two hours. Cysteine containing carboxamide peptides were cleaved from the resin and side chain deprotected with 2.5% (v/v) EDT, 2.5% (v/v) TIPS, and 1% (v/v) water in TFA for two hours. Hydrazide peptides were cleaved with 5% (v/v) EDT, 5% (v/v) TIPS, and 2.5% (v/v) water in TFA for two hours. In all cases, the resin was removed and compressed air was used to evaporate the cleavage solution to dryness at RT. The resulting solids were washed three times with cold diethyl ether, dissolved in 50% A/50% B (v/v), and lyophilized. Side chain protection was as follows: Arg(Pbf), Tyr(tBu), Lys(Boc), Asp(OtBu), Gln(Trt), Ser(tBu), His(Trt), Asn(Trt), Trp(Boc), Glu(OtBu), Thr(tBu), Cys(Trt).

The Wang resin was functionalized as follows: 5.47 g Wang resin was added to a 500 ml round bottom flask and suspended in 98 mL of DCM and 1.12 mL of N-Methyl morpholine. This was stirred in an ice bath for 5 min and 2.03 g p-nitrophenol chloroformate was added as a powder. This mixture was stirred for 8.5 hours. The ice in the bath was not replenished, which allowed the reaction to slowly reach RT. The mixture was filtered and the solids washed with DCM, DMF, MeOH, and DCM to give a white resin. The resulting resin was placed in a clean 500 ml round bottom flask in an ice bath, and suspended in a prepared mixture of 210 mL DMF, 54 mL DCM, and 1.1 mL hydrazine monohydrate pre-chilled to 0° C. This yielded a bright yellow solution. The reaction proceeded for 18 hours in an ice bath that was allowed to melt. The mixture was then filtered, and the solids washed as before to give hydrazine-functionalized Wang resin.

All peptides were analyzed on an Agilent 6520 Accurate Mass Q-TOF LC-MS under one of four conditions, as indicated below. Condition 1: an Agilent C3 Zorbax SB column (2.1 mm×150 mm, 5 μm packing) was used (condition 1). The flow rate was 0.4 mL/min of the following gradient: A' with 1% B' for 3 minutes, 1-61% B' ramping linearly over 15 min, and 61% B' for 4 minutes. Condition 2: For GCF and LYRAG (SEQ ID NO: 2) as well as other peptides, an Agilent C18 Zorbax SB column (2.1 mm×250 mm, 5 μm packing) was used. The flow rate was 0.4 mL/min of the following gradient: A' with 1% B' for 5 minutes, 1-61% B' ramping linearly over 15 min, and 61% B' for 4 minutes. Condition 3: an Agilent C3 Zorbax SB Column (2.1 mm×150 mm, 5 μm packing) was used with a flow rate of 0.8 mL/min of the following gradient: A' with 5% B' for 3 minutes, 5-65% B' ramping linearly over 9 min, and 65% B' for 1 minute. Condition 4: An Agilent C3 Zorbax SB column (2.1×150 mm, 5 μm packing) was used with a flow rate of 0.4 mL/min of the following gradient: A' with 5% B' for 3 minutes, 5-95% B' ramping linearly over 15 min, and 95% B' for 4 minutes. Unless noted, peptides were analyzed under condition 1. LYRAG (SEQ ID NO: 2) used in the coupling time study and GCF used in the cysteine activation studies were analyzed under condition 2. Peptides in FIGS. 23C, 21A-B, 20, and 17 were analyzed under condition 3. Peptides in FIGS. 23E, 22, and 21C were analyzed under condition 4. Total ion current is displayed in all chromatograms.

The peptides were purified as follows. Crude peptides were dissolved in 95% A/5% B (v/v) and purified on a Waters preparative HPLC with an Agilent Zorbax SB C18 column (21.2 mm×250 mm, 7 μm packing), a linear gradient from 5%-45% B in A over 80 min, and a flow rate of 10 mL/min. The crude affibody Fragment 1-39 ligation product was purified on a Beckman System Gold semi-preparative HPLC with a Zorbax C18 column (9.4 mm×250 mm, 5 μm packing), a linear gradient from 10% to 55% B in A over 90 minutes, and a flow rate of 5 mL/min. The final affibody was purified on the same system with the same gradient, using a Jupiter C18 column (4.6 mm×250 mm, 5 μm packing) and a flow rate of 2.3 mL/min.

For all purifications, one minute fractions were collected and screened for the correct mass on a PerSpective Biosystems Voyager-DE MALDI-TOF using 2 μL of the fraction co-crystallized with 2 μL of 50% A'/50% B' (v/v) saturated with alpha-cyano-4-hydroxycinnamic acid matrix. The purity of pooled fractions was confirmed by LC-MS, as above.

The UV detector response was quantified as follows. To understand the UV traces produced and the wash efficiencies they represent, the response of the UV detector was quantified. To determine the approximate concentration of amino acid in the UV traces, a serial dilution of Fmoc-Ala-OH coupling solution was prepared. The initial concentration of amino acid was about 0.3M (2 mmol in 6.5 mL total volume) 10×, 100×, 1000×, 10,000 and 100,000× dilution standards were prepared and injected directly into the UV detector. The 100× dilution ($3\times10^{-3}$M) was just below saturation. The 10,000× dilution ($3\times10^{-5}$M) standard was just above baseline, about 1% of scale, as expected. The 100,000× dilution was below the detection limit. The highly reproducible washout traces (FIG. 10) show that this is representative of all amino acids (qualitatively different traces between cycles would be expected if the absorbance was vastly different).

Example 13

This example describes the general conditions for peptide synthesis with the second generation reactor. This method was sufficiently robust that all of these peptides were synthesized without UV monitoring of the reactor effluent.

Increasing the diameter of the reactor reduced the backpressure, and maintaining a comparable volume allowed the same volumes of solvents and reagents to be used as the first generation reactor. The second generation reactor accommodated up to 200 mg of resin and accommodated flow rates up to 100 mL/min. More resin was not used, because the selected resin swelled as the peptide was elongated and the volume limiting inserts restricted the swollen volume of the resin to 2 mL. Higher flow rates were not tested, but the observed backpressure indicated that higher flow rates could be achieved.

With the second generation reactor, cycle time was reduced by washing at a higher flow rate. As expected, the required wash time continued to decrease with increasing flow rate, with 99% of the amino acid removed in 36 seconds at 20 mL/min and 20 seconds at 40 mL/min. However, to accommodate manual operation and allow operators adequate time to prepare each subsequent amino acid, one minute washes at 20 mL/min or 30 second washes at 40 mL/min were used.

Peptides in FIGS. 16A-B, 17, 18 A-B, 19 A-C, 20, 21, 22A, and 24A were synthesized using the second generation reactor described in Example 8 and the synthesizer described in Example 1 at 60° C. under conditions described in this Example, with reagents heated immediately before use via a coil of tubing in a water bath. ACP (65-74) shown in FIG. 16C was synthesized as below, but at room temperature, and ACP (65-74) shown in FIG. 16D was synthesized in a standard glass reactor. In all cases, one synthetic cycle consisted of amide bond formation (coupling), removal of coupling reagent (wash), Nα Fmoc removal (deprotection), and removal of the deprotection reagent and reaction product, piperidine-dibenzofulvene (piperidine-DBF) (wash).

Unless noted, coupling was performed by delivering the following coupling solution at 6 mL/min (for approximately 30 seconds). The coupling solution consisted of 1 mmol of Nα-Fmoc and side chain protected amino acid dissolved in 2.5 mL of 0.4 M HBTU in DMF and 0.5 mL of DIEA. Cysteine was dissolved in 2.5 mL 0.4 M HBTU in DMF and 0.157 mL DIEA. In both cases, amino acids were dissolved in HBTU solution up to several hours before use, and DIEA was added within two minutes of use. Volumetric measurements were made at RT (18-20° C.). The ACP (65-74) shown in FIG. 16A, and the protease sites in FIG. 17 were synthesized by substituting HATU for HBTU in the above solution. Next, the coupling solution was removed with 20 mL of DMF delivered at 20 mL/min over 1 minute, and then the Nα-Fmoc protecting group was removed with 6.6 mL of 50% (v/v) piperidine in DMF delivered at 20 mL/min over 20 seconds. Excess piperidine and piperidine-DBF were removed with 20 mL of DMF delivered at 20 mL/min over 1 minute to complete one cycle. Peptides were synthesized on 1% divinyl benzene crosslinked polystyrene resin. To produce C-terminal carboxamide peptides, 175 mg of MBHA functionalized resin with a stated loading of 1 mmol per gram was used, and the TFA labile Rink linker was coupled as the first amino acid. To produce C-terminal hydrazide peptides, 200 mg of chlorotrytyl hydrazide (hydrazide) resin, prepared as below, was used.

Non-cysteine containing peptides were cleaved from the resin and side-chain deprotected by treatment with 2.5% (v/v) water and 2.5% (v/v) TIPS in TFA for two hours at RT. Cysteine containing peptides were cleaved from the resin and side chain deprotected with 2.5% (v/v) EDT, 2.5% (v/v) water, and 1% (v/v) TIPS in TFA for two hours at RT. In all cases, the resin was removed and nitrogen was used to evaporate the cleavage solution to dryness at RT. The resulting solids were washed three times with cold diethyl ether, dissolved in 50% A/50% B (v/v), and lyophilized. Side chain protection was as follows: Arg(Pbf), Tyr(tBu), Lys (Boc), Asp(OtBu), Gln(Trt), Ser(tBu), His(Trt), Asn(Trt), Trp(Boc), Glu(OtBu), Thr(tBu), Cys(Trt).

For studies conducted with the second generation reactor, a different resin was used to generate C-terminal hydrazides, because the Wang resin, used above, was found to promote significant double incorporation of glycine. We were unable to solve this problem, so changed resins. The hydrazide resin was produced as follows: 16 grams of chlorotrytyl chloride resin with a stated loading of 1.2 mmol/gram were suspended in 150 mL of dry, amine free DMF and stirred for 15 minutes. To this, a suspension of 25 mL of DIEA, 50 mL of DMF, and 10 mL of anhydrous hydrazine was added drop wise. During addition, two layers formed and the bottom was added first. After addition was complete, the mixture was allowed to stir for one hour, and was then quenched with 50 mL of methanol. The resin was removed and washed with five 100 mL portions of each of DMF, water, DMF, methanol, and diethyl ether (for a total wash volume of 2.5 L). The resin was then dried for three hours at reduced pressure (≈5 torr), resulting in a free flowing powder with lumps. The lumps were gently broken before use, taking care not to generate fines that could clog the reactor's frit.

FIGS. 16A-D show crude LCMS chromatograms for ACP (65-74) synthesized with the second generation protocol at (A) 60° C. using HATU as an activator, (B) 60° C. using HBTU as an activator, (C) room temperature using HBTU as an activator, and D) room temperature synthesis using a comparable manual batch method. For comparison, FIGS. 16E-H show ACP (65-74) synthesized under comparable conditions with the first generation reactor and protocol: (E) 60° C. using HATU as an activator, (F) 60° C. using HBTU as an activator, (G) room temperature using HBTU as an activator, and (H) room temperature using a comparable manual batch method. The total ion current is displayed in each chromatogram.

Example 14

This example compares the synthesis of ACP (65-74), conotoxin, HIV-1 protease fragment, and affibody fragments in the second generation reactor using the synthetic timeline in FIG. 12G to the synthesis of ACP (65-74), conotoxin, HIV-1 protease fragment, and affibody fragments in the first generation reactor as described in Examples 1, 5, and 6. The peptides formed in the second generation reactor were of comparable quality to the peptides synthesized in the first generation reactor.

To compare the performance of the first and second generation synthesis protocols and reactors, ACP (65-74) was synthesized with the second generation reactor and cycle with HATU activation, HBTU activation, and HBTU activation at room temperature. For comparison, the data in FIG. 4 is reproduced, and the accelerated room temperature batch experiment was repeated. The standard second generation syntheses with HBTU and HATU are slightly worse than the first generation synthesis, but the second generation RT control has significantly reduced co-eluting Gln deletion product. The performance of the two protocols is different, but comparable. Overall, the second generation system is preferred for its reduced cycle time and vastly improved mechanical reliability. As of this writing, our lab exclusively uses the second generation protocol and reactor for peptide synthesis.

Figure 18:
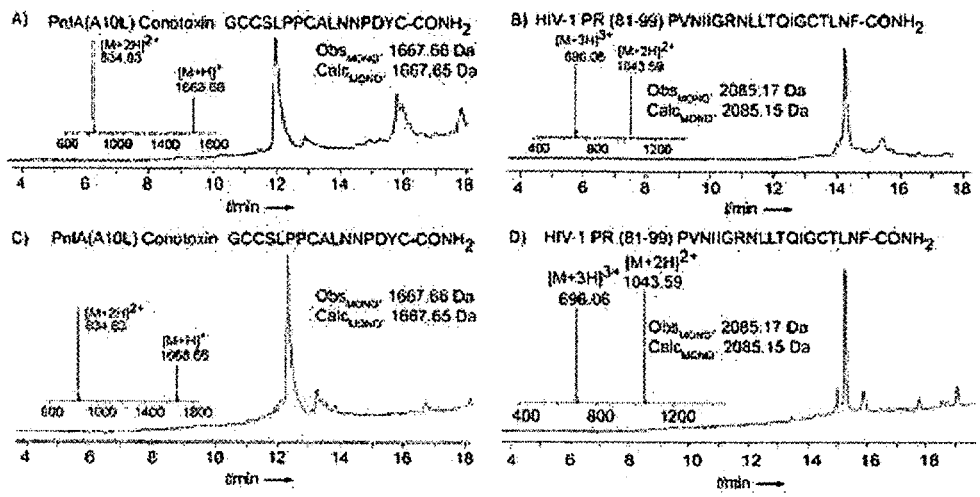
FIGS. 18A-D are, according to one set of embodiments, chromatograms of (A) PnIA (A10L) conotoxin (SEQ ID NO: 4) synthesized with a second generation protocol, (B) HIV-1 PR (81-99) (SEQ ID NO: 5) synthesized with a second generation protocol, (C) PnIA (A10L) conotoxin (SEQ ID NO: 4) synthesized with a first generation protocol, and (D) HIV-1 PR (81-99) (SEQ ID NO: 5) synthesized with a first generation protocol.

To further compare the performance of the first and second generation synthesis protocols and reactors, the syntheses of the HIV-1 protease fragment and the PnI (A10L) Conotoxin were repeated. The data is shown in FIG. 18, along with the data from FIG. 5 for comparison. The performance of the two protocols is comparable.

Figure 19:
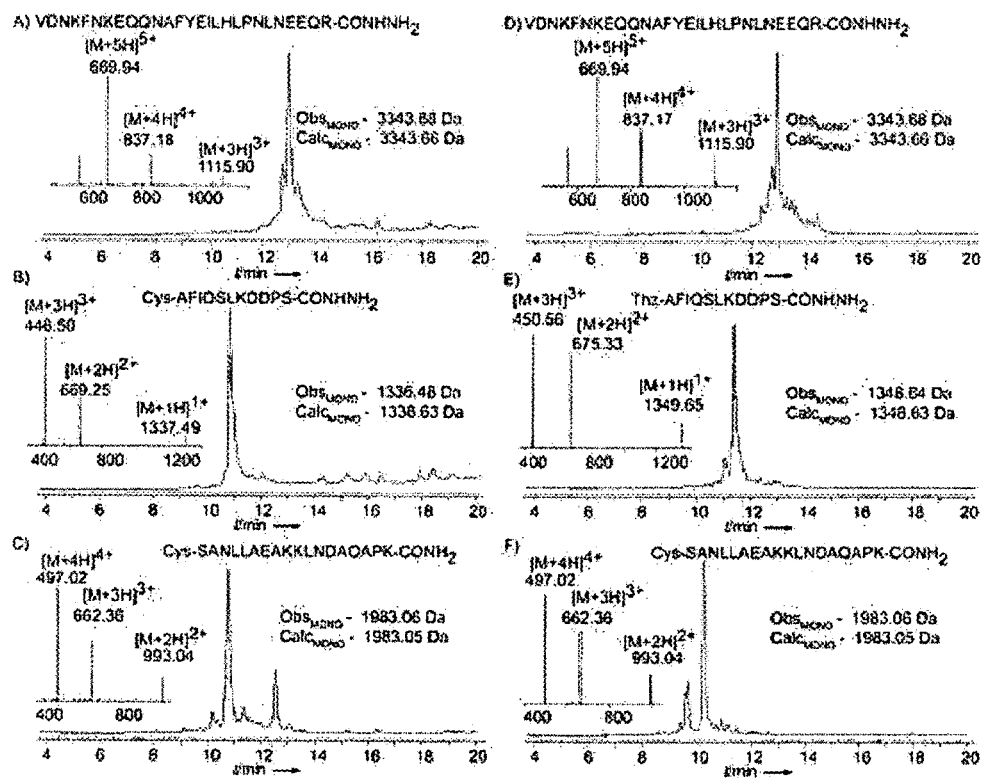
FIGS. 19A-F are chromatograms, according to certain embodiments, of (A-C) affibody fragments synthesized on chlorotrytyl hydrazide functionalized polystyrene with a second generation protocol (sequences in FIGS. 19A-19C correspond to SEQ ID NOs.: 6, 20, and 8, respectively) and (D-F) affibody fragments synthesized on modified Wang resin with a first generation protocol (sequences in FIGS. 19D-19F correspond to SEQ ID NOs.: 6, 7, and 8, respectively.

To validate the performance of the chlorotrytyl hydrazide resin and further explore synthesis with the second generation reactor and cycle, the synthesis of the affibody fragments was repeated. The data is shown in FIG. 19, along with the data from FIG. 7 for comparison. The performance of the two linkers is comparable when synthesizing fragments without glycine. The modified Wang resin promotes significant double incorporation of glycine, which motivated our move to hydrazide resin. In both cases, pure material suitable for ligation was obtained after preparative chromatography.

To further highlight the utility of the second generation synthesizer, a library of 10 glutathione analogues (see FIG. 20), several cysteine rich peptides (see FIG. 21), and two biotinylated protease recognition sites (see FIG. 17) were synthesized. The glutathione analogues were all produced in one day. In FIG. 21, all cysteines were acetamidomethyl (Acm) protected, to prevent side reactions during cleavage and side chain deprotection. Cysteine in these peptides was activated with 0.190 mL of DIEA rather than 0.157 mL. In all cases, peptides were produced on a 0.2 mmol scale, the major peak is the desired product, and crude material was successfully purified in one preparative RP-HPLC step (purified material is not shown).

Figure 17:
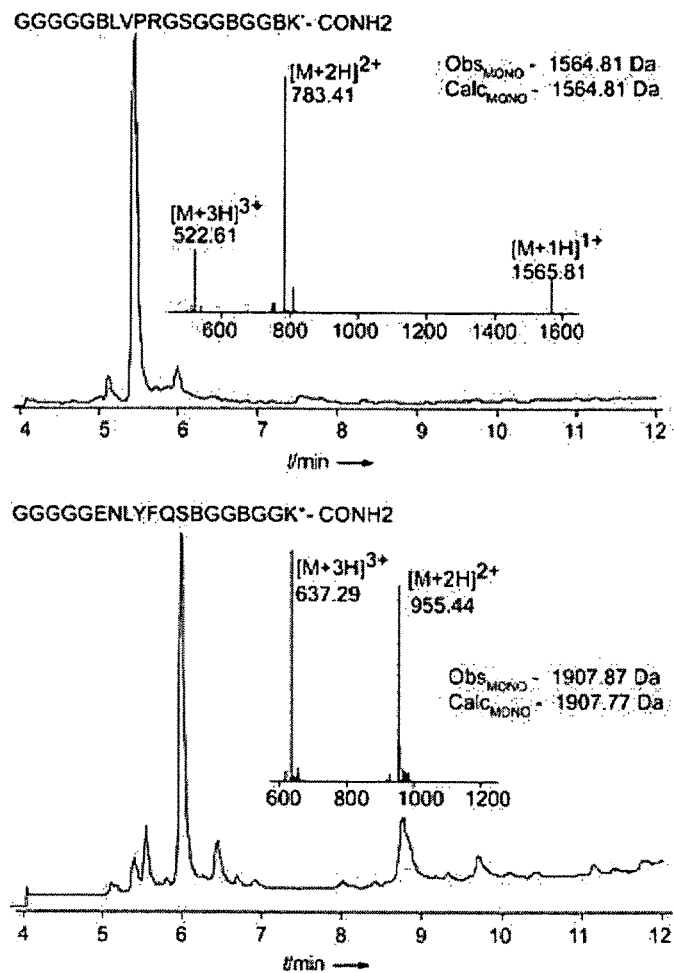
FIG. 17 includes chromatograms of synthesized biotinylated peptides, according to some embodiments (sequences from top to bottom correspond to SEQ ID NOs.: 18 and 19, respectively)

FIG. 17 shows chromatograms of synthesized biotinylated protease recognition sites. B is β-alanine, K* is biotinylated lysine, and K' is alloc protected lysine. The alloc protected peptide was hydrogenated in batch on-resin to give free lysine, and biotin was coupled in batch. Material eluting after 8 minutes is non-peptidic.

FIG. 18 shows chromatograms for the resynthesis of HIV-1 protease fragment and PnI (A10L) conotoxin. Specifically, FIG. 18A-D show (A) conotoxin synthesized with the second generation reactor and conditions, (B) HIV-1 PR (81-99) synthesized with the second generation reactor and conditions, (C) conotoxin synthesized with the first generation reactor and conditions, and (D) HIV-1 PR (81-99) synthesized with the first generation reactor and conditions. Late eluting material was side chain protected products. Retention times differ slightly because the LC/MS column was replaced between first and second generation reactor studies. Material eluting after 15 minutes was non-peptidic.

FIG. 19 shows chromatograms of affibody fragments. FIGS. 19A-C show fragments synthesized on chlorotrytyl hydrazide functionalized polystyrene with the second generation protocol and FIGS. 19D-F show fragments synthesized on modified Wang resin with the first generation protocol.

Figure 20:
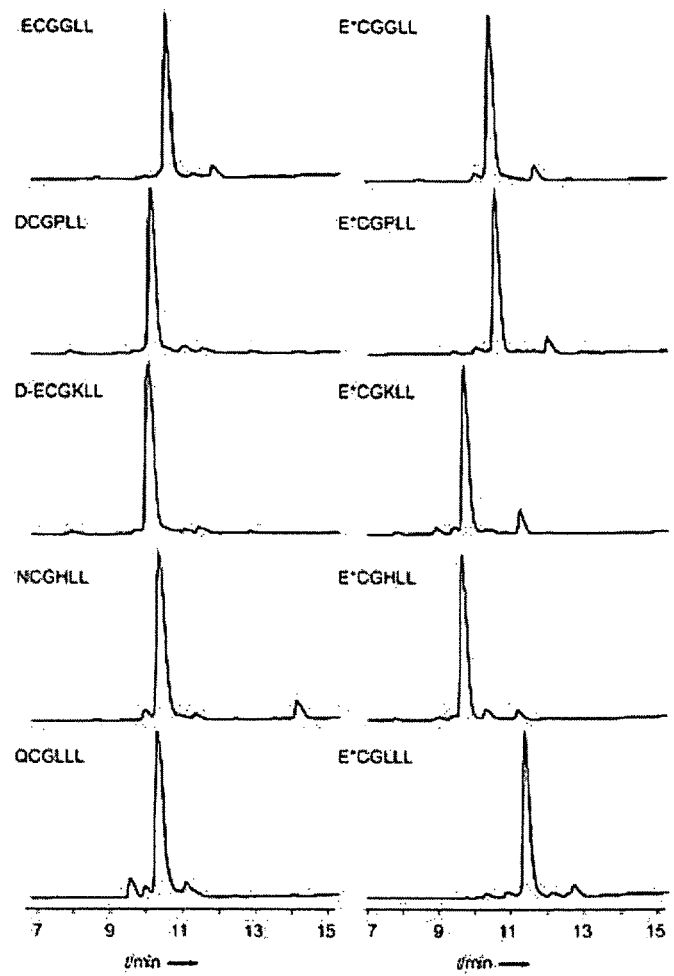
FIG. 20 includes chromatograms of a library of glutathione analogues synthesized according to one set of embodiments (sequences from left to right and top to bottom correspond to SEQ ID NOs.: 21-30, respectively)
Figure 21:
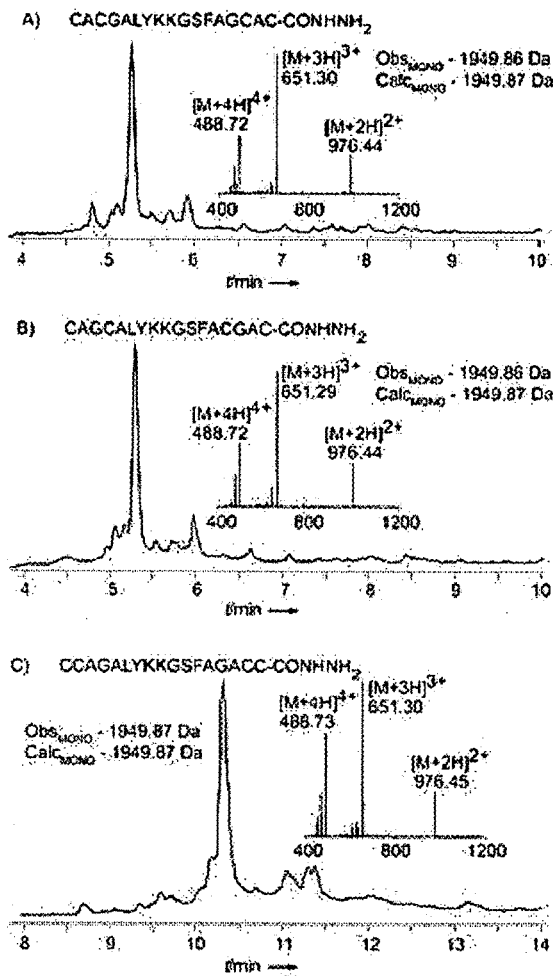
FIGS. 21A-C are chromatograms of cysteine rich peptides synthesized according to certain embodiments (sequences in FIGS. 21A-21C correspond to SEQ ID NOs.: 31-33, respectively)

FIG. 20 shows chromatograms for a library of glutathione analogues synthesized in 18 minutes each. E* represents glutamic acid coupled to the polypeptide through the side chain carboxylate. All peptides were analyzed under condition 3, and the main peak has the desired mass.

FIG. 21 shows chromatograms for several cysteine rich peptides. All cysteine was Acm protected. Material in FIGS. 21A and B was analyzed under condition 3, and material in FIG. 21C was analyzed under condition 4.

Example 15

This example describes the design and construction of the automated flow platform.

The automated platform was designed to perform to the same standard as the manual system, without the restrictions on cycle time imposed by a human operator. To accomplish these goals, we assembled the system shown in FIG. 23A. The automated flow based platform contained two HPLC pumps, a static mixer, a microcontroller (not shown), a heat exchanger, a second generation reactor, and a UV detector amongst other components. The two HPLC pumps delivered reagents. One HPLC pump delivered solutions of amino acids and HBTU dissolved in DMF, the other delivered DIEA to complete activation. Amino acids were stored as 0.4 M solutions with equimolar HBTU in DMF, and were stable for weeks without the activating base if stored in sealed reactors.

A static mixer was used to ensure effective mixing of DIEA and the amino acid solutions, and the valve positions and pump flow rates were controlled by an Arduino microcontroller. The static mixer blended these two fluids, and the heat exchanger, second generation reactor, and UV detector described above were used without modification. To increase the residence time between the static mixer and reactor, an additional six feet of 0.030" ID tubing was used. The increased residence time may promote complete activation, and peptides produced with this extra length of tubing in the system were observed to be of slightly higher crude purity than peptides without it.

All of the valves shown in FIG. 23A were contained in two manifolds and were actuated by 24 V solenoids. The manifolds were designed to have minimal internal volume and give zero cross talk between reagents. One manifold consisted of valves to select one of five reagents, and one valve to turn the manifold on or off. When de-energized, the reagent valves selected DMF and the on/off valve turned the manifold off. These features prevented any incorrect incorporation of amino acids, minimized the volume of solvent required to wash the manifold, and prevented siphoning solvent. The entire flow path was PTFE. Inlet lines were protected by 2 micron inlet filters.

The pumps were both Knauer Smartline model 100 with 50 mL/min pump heads. These pumps were selected because they were readily available and easily controlled with an analog voltage. However, the pumps had a relatively low pumping capacity and required about 10 mL of solvent to wash the pump heads. The cycle time could be further decreased by selecting pumps that have a higher pumping capacity and require a lower volume of solvent to wash the pump heads.

The static mixer was supplied by StaMixCo, and consists of 6 of their smallest elements (6 mm). The heat exchanger, described previously, was placed between the mixer and second generation reactor. All three of these elements, and the extra length of tubing, were placed in a 60° C. water bath. The UV detector described previously was used to monitor the absorbance of the waste stream. This device was controlled by an Arduino Mega2560 microcontroller, selected for its simplicity and stability. To supply a 0-10V analog signal to control the pumps, the Arduino's 0-5 V pulse width modulated outputs were used. The signal was filtered and amplified to generate a 0-10 V analog control voltage. To control the valves, the Arduino's digital outputs were used to actuate power transistors that then supplied 24V DC power from an external supply. All grounds were common with building ground.

Figure 23:
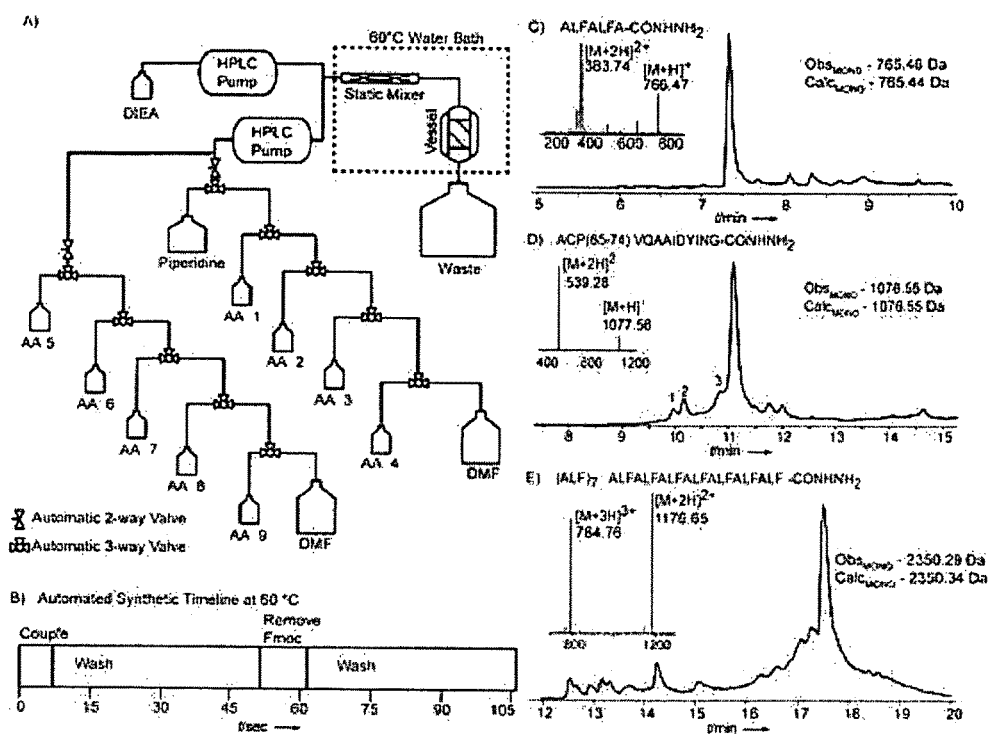
FIGS. 23A-D are (A) a schematic of an automated flow platform, (B) a synthetic timeline used by the automated flow platform to incorporate an amino acid residue, (C) a chromatogram showing ALFALFA (SEQ ID NO: 48), (D) a chromatogram showing ACP (65-74) (SEQ ID NO: 3), and (E) a chromatogram showing (ALF)7 (SEQ ID NO: 34), according to one set of embodiments.

FIG. 23 shows the automated peptide synthesis platform and several model peptides synthesized with it. FIG. 23A-E are (A) a schematic of the device, (B) the synthetic timeline used by this device to incorporate an amino acid residue every 107 seconds, (C) a chromatogram showing ALFALFA (SEQ ID NO: 48) assembled in 12 minutes, (D) a chromatogram showing ACP (65-74) assembled in 18 minutes (1,2=Ile deletion, 3=hydrolysis of the C-terminus), and (E) a chromatogram showing (ALF)7 assembled in 37 minutes. Total ion chromatograms are shown.

Example 16

This example describes the synthesis of peptides using the automated system. The automated cycle time was not limited by the rate at which a user could complete manual tasks or a syringe pump could infuse, so the timeline was substantially accelerated (see FIG. 23B). Two 45 second washes at 50 mL/min (the maximum available), a seven second coupling, and a ten second deprotection resulted in the incorporation of an amino acid residue every 107 seconds (1.8 minutes). The coupling time and deprotection time represent such a small fraction of the total time that the times were not optimized. However, even faster times can be achieved by optimizing the coupling time and deprotection time. Faster addition cycles can also be achieved by eliminating one or more of the wash steps. Using these cycles, ALFALFA (SEQ ID NO: 48) was produced in 12.5 minutes, ACP (65-74) was produced in 17.8 minutes, and (ALF)7, a model 21-mer synthesized to demonstrate that the system is mechanically robust, was produced in 37.5 minutes. The crude quality of (ALF)7 was nearly identical to a synthesis using the manual second generation synthesis protocol (see FIG. 24).

The following control cycle was used to synthesize peptides with the automated system. The desired solution of amino acid and activator was selected and delivered at 50 mL/min by the first HPLC pump. Four seconds later, the second HPLC pump began delivering DIEA at 9 mL/min. After three more seconds (for a total coupling of 7 seconds) the manifolds selected DMF wash solvent. Sixteen seconds later, when the amino acid was almost completely washed out of the manifold and pump, the second HPLC pump was deactivated. After another 31 seconds (for 45 seconds of total wash time at 50 mL/min), 50% piperidine in DMF was delivered for 10 seconds at 50 mL/min. Finally, DMF was delivered for another 45 seconds at 50 mL/min, completing the final wash and the cycle. Solutions of amino acid and activator were prepared by dissolving 40 mmol of Nα-Fmoc protected amino acid in 100 mL of 0.4 M HBTU in DMF. Side chain protection was as follows: Arg(Pbf), Tyr(tBu), Asp(OtBu), Gln(Trt), Asn(Trt). No correction was made for the change in volume upon dissolution of the amino acids.

Figure 22:
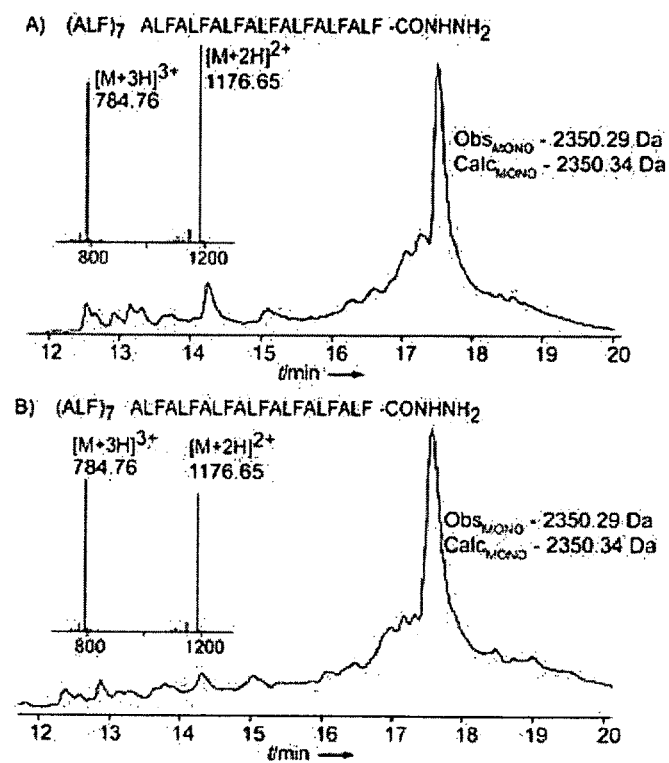
FIGS. 22A-B are chromatograms for (A) (ALF)7 synthesized using an automated process and (B) (ALF)7 synthesized using a manual process, according to certain embodiments (sequences in FIGS. 22A and 22B correspond to SEQ ID NO: 34)
Figure 24:
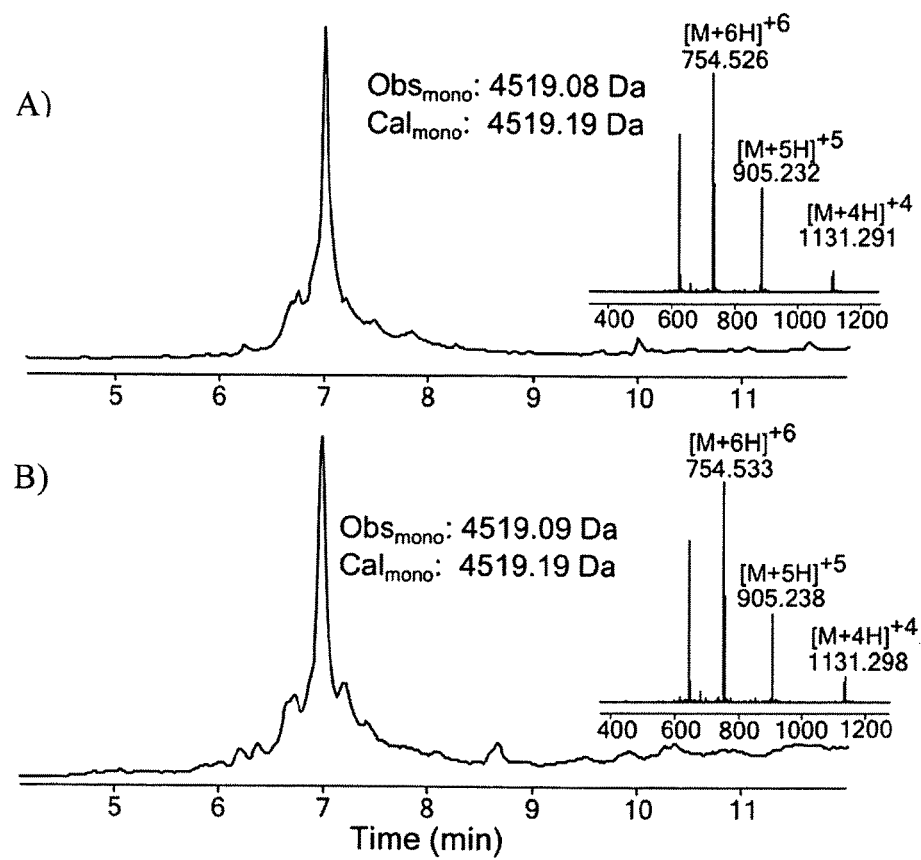
FIGS. 24A-B show (A) a chromatogram of a peptide (SEQ ID NO: 35) synthesized using addition cycles including removal steps and (B) a chromatogram of a peptide synthesized using addition cycles lacking one or more removal step.
Figure 25:
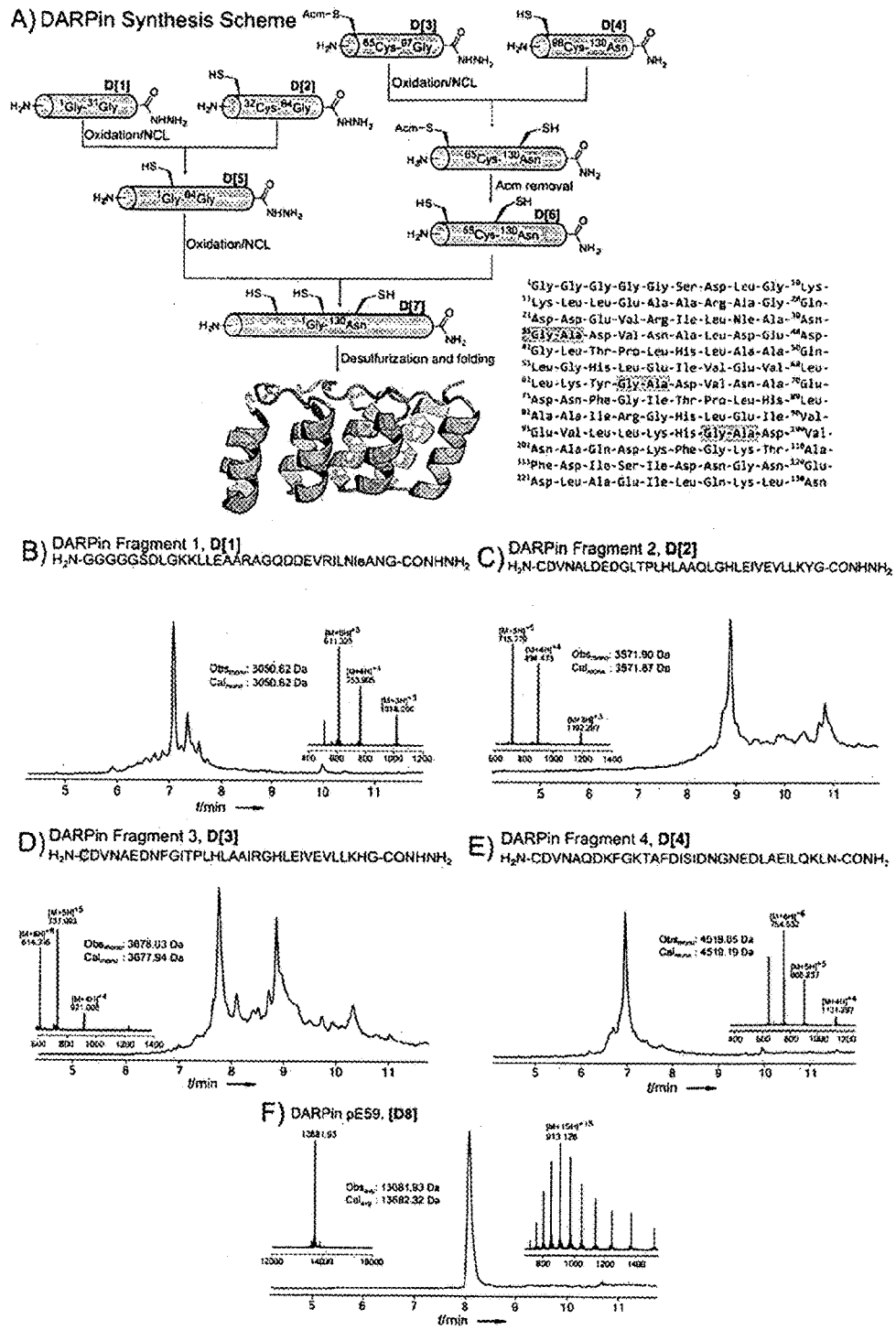
FIGS. 25A-F show (A) a synthetic scheme for DARPin (SEQ ID NO: 36) synthesis, (B-E) chromatograms of fragments DARPin (sequences in FIGS. 25B to 25E correspond to SEQ ID NOs.: 37-40, respectively), and (F) a chromatogram of DARPin, according to one set of embodiments.
Figure 26:
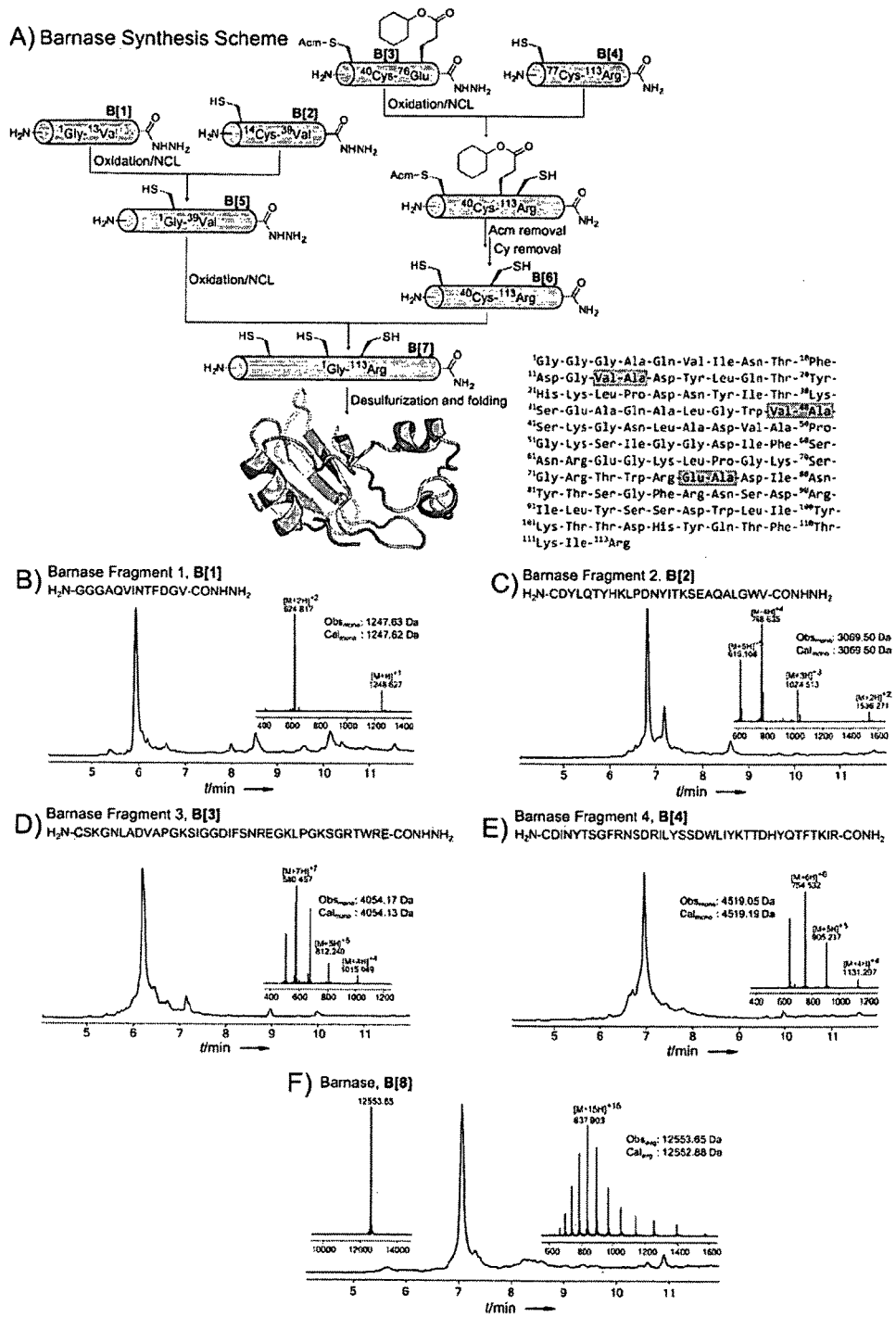
FIGS. 26A-F show (A) a synthetic scheme for Barnase (SEQ ID NO: 41) synthesis, (B-E) chromatograms of fragments Barnase (sequences in FIGS. 26B to 26E correspond to SEQ ID NOs.: 42-44 and 35, respectively), and (F) a chromatogram of Barnase, according to certain embodiments.

Three peptides, ALFALFA (SEQ ID NO: 48), ACP (65-74), and (ALF)7 were produced with the fully automated system. ALFALFA (SEQ ID NO: 48) was of extremely high crude purity, and ACP (65-74) has been synthesized many times under many conditions with the manual system. To compare the automated synthesis of (ALF)7 to the manual system, (ALF)7 was produced with the second generation reactor and protocol. The chromatograms are shown in FIG. 24. The quality of the two crude products is very similar. FIG. 22 shows chromatograms for (ALF)7 synthesized with (A) the automated 1.8 minute cycle and (B) manual three minute cycle.

Example 17

This example describes the synthesis of a peptide using addition cycles that lacked one or more reagent removal step. In some cases, as illustrated in this FIG. 24, one or more reagent removal step is optional and the absence of the removal step does not negatively affect the performance of subsequent steps and/or addition cycles.

Two peptides differing only in the steps included in addition cycle were synthesized. The sequence of the peptide was H$_2$N-CDINYTSGFRNSDRILYSSDWLIYKTTD-HYQTFTKIR-CONH$_2$ (SEQ ID NO: 35). One peptide was synthesized as described in Example 13 and served as the control. The addition cycles consisted of amide bond formation (coupling), removal of coupling reagent (wash), Nα Fmoc removal (deprotection), and removal of the deprotection reagent and reaction product, piperidine-dibenzofulvene (piperidine-DBF) (wash). The chromatogram for the synthesized peptide is shown in FIG. 24A. Another peptide was synthesized as described in Example 13, except the additional cycles did not include the coupling agent removal step (i.e., coupling agent wash step). The incoming solvent from the subsequent step (e.g., deprotection step) served to wash away at least a portion of the coupling reagent and/or reaction byproducts and the remaining coupling reagent was destroyed by the excess incoming deprotection reagent. The chromatogram of the peptide synthesized using addition cycles that lacked a coupling reagent wash step is shown FIG. 24B. No significant difference was observed between the peptide lacking the optional wash step and the peptide that included the optional wash step.

Example 18

This example describes the synthesis of the 130 residue DARPin pE59 and the 113 residue Barnase. Each of these proteins was synthesized from four peptide fragments using ligation chemistry known to those of ordinary skill in the art and substantially similar to that described in Example 6 for the affibody.

The DARPin was synthesized from four fragments, with total ion chromatograms shown in FIG. 25B-E:
D[1] (H2N-[1Gly-31Gly]-CONHNH2),
D[2] (H2N-[32Cys-64Gly]-CONHNH2),
D[3] (H2N-[65Cys-97Gly]-CONHNH2), and
D[4] (H2N-[98Cys-130Asn]-CONH2).
These were synthesized using the second generation reactor described in Example 8, methods described in Example 13, and the HBTU coupling agent with the following exceptions. All cysteines were Acm protected.

D[1] was synthesized in two minutes per residue with two 30 second washes at 40 ml/min. Further, the deprotection was performed for 20 seconds at 40 ml/min due to difficulties in manually changing the pump flow rate. It is believed that shorter deprotections and/or lower flow rate deprotections and/or deprotections with more dilute deprotection reagent (e.g. 20% piperidine in DMF) would be effective with this accelerated cycle and conserve deprotection reagent.

D[2] and D[3] were synthesized as described in Examples 8 and 13. D[4] was synthesized on aminomethyl-polystyrene resin, rather than MBHA-polystyrene resin. The resin was prepared as described in Example 20. 114Ser and 113Ile were incorporated as a 2,2 dimethyl pseudoproline dipeptide, and coupled for 10 minutes by pausing the addition cycle after complete delivery of the coupling reagent. It is believed that this pause is unnecessary. 116Asp was incorporated with 3-methyl pentyl ester side chain protection, rather than standard t-butyl ester side chain protection. Finally, deprotections were performed for 20 seconds at 20 ml/min with 20% piperidine and 0.1M HOBt in DMF.

Barnase was synthesized from four fragments, with total ion chromatograms shown in FIG. 26B-E:
B[1] (H2N-[1Gly-13Val]-CONHNH2)
B[2] (H2N-[14Cys-39Val]-CONHNH2).
B[3] (H2N-[40Cys-76Glu]-CONHNH2) and
B[4] (H2N-[74Cys-113Arg]-CONH2).
These were synthesized using the reactor described in Example 8, methods described in Example 13, and the HATU coupling agent with the following exceptions. All peptides were synthesized using 20% piperidine in DMF as the deprotection reagent. All cysteines were Acm protected, and 76Glu was incorporated as the cyclohexyl ester. For the synthesis of B[1], the c-terminal valine was coupled to the resin for 10 minutes by pausing the addition cycle after delivery of the valine coupling reagent. It is believed that a shorter coupling and/or a coupling at higher temperature can be used, however it was found that the 30 second coupling at 60° C. described in Example 13 was not adequate to quantitatively bond sterically hindered valine to sterically hindered trityl hydrazide resin.

For the synthesis of B[2], the c-terminal valine was coupled to the resin for 10 minutes, as in B[1], and 33Ala was incorporated with hydroxy methoxy benzyl (HMB) backbone protection. This residue was activated with DCC/HOBt rather than HATU and coupled for 25 minutes by pausing the amino acid addition cycle for 25 minutes after complete delivery of the coupling reagent. The subsequent glutamic acid was coupled for 30 minutes by pausing the amino acid addition cycle for 30 minutes after complete delivery of the coupling reagent. It is believed that incorporation of HMB protected amino acids can be accelerated by operating at higher temperature.

B3 was synthesized as described above and in Examples 8 and 13.

B4 was synthesized on Rink-PEG resin supplied by ChemMatrix, and 90Arg was activated with DCC/HOBt rather than HATU.

After preparation of the crude protein fragments, they were purified by RP-HPLC using methods known to those of ordinary skill in the art and substantially similar to those described in Example 12. The purified fragments were then ligated according to the schemes in FIGS. 25A and 26A to afford the full length proteins shown in FIGS. 25F and 26F, respectively. Ligation was performed with methods known to those of ordinary skill in the art, following the procedure of Liu and co-workers with minor modifications.

Example 19

Figure 27:
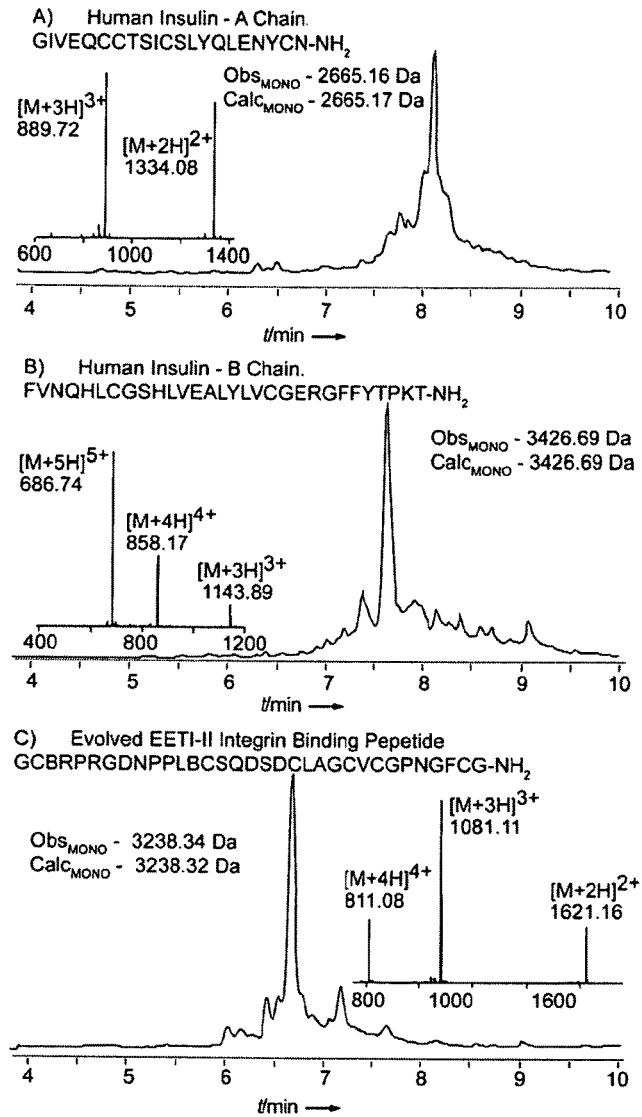
FIGS. 27A-C show (A) a chromatogram of human insulin A chain (SEQ ID NO: 45), (B) a chromatogram of human insulin B chain (SEQ ID NO: 46), and (C) a chromatogram of evolved EETI-II integrin binding peptide (SEQ ID NO: 47), according to certain embodiments.

This example describes the synthesis of the A and B chains of human insulin and an evolved integrin binding scaffold based on the EETI-II trypsin inhibitor. Total ion chromatograms of the crude synthetic products are shown in FIG. 27A-C, respectively. All of these peptides were synthesized using amino methyl functionalized polystyrene instead of MBHA functionalized polystyrene. The amino methyl functionalized polystyrene was prepared using methods known to those of ordinary skill in the art and as described below in Example 20.

The A chain of human insulin was synthesized using the second generation reactor described in Example 8 and the methods described in Example 13, except the synthesis was conducted at 85° C. and all cysteines were Acm protected. The B chain of human insulin was synthesized using the reactor described in Example 8 and the methods described in Example 13, except the synthesis was conducted at 85° C. The integrin binding scaffold was synthesized using the reactor described in Example 8 and the methods described in Example 13, except all chiral amino acids were of inverted chirality (i.e. dextrorototory).

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used.

Example 20

This example describes a procedure for preparation of amino methyl resin used in Examples 18 and 19.

To prepare amino methyl resin, 25 g of Bio-Rad, Biobeads S-X1 (styrene-divinylbenzene copolymer, 1% crosslinkage) and 4.9 g (27.6 mmol) of N-hydroxymethylphthalimide were added to 450 mL of DCM in a 1 L round bottom flask. To this, 50 mL of methanesulfonic acid was added and the reaction was stirred gently for 5 hours at room temperature. After 5 hours of stirring, the slurry was transferred to a coarse fritted glass funnel and washed with DCM (1500-2000 mL) and ethanol (1500 mL). The resin was then dried under vacuum for 1 hour. After drying, the phthalimidomethyl-resin was transferred to a 500 mL round bottom flask and suspended in a 200 mL solution of hydrazine monohydrate (20% v/v) in absolute ethanol. A reflux condenser was attached and the solution was refluxed gently for at least 8 hours. The resulting gelatinous material was transferred hot to a glass fritted funnel and washed with boiling ethanol (1000-2000 mL) and then hot methanol (1000 mL) in order to completely wash away the white pthalhydrazide precipitate. The resin was then washed with DMF (800 mL), DCM (800 mL), 10% (v/v) DIEA in DMF (500 mL), DMF (600 mL), and DCM (1000 mL). The resin was then dried under vacuum and determined to have a loading of 1.2 mmol/g.

Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or"

as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A process for adding amino acid residues to peptides, comprising:
   providing a plurality of peptides comprising protection groups, each peptide immobilized on a solid support;
   performing a first amino acid addition cycle comprising exposing the immobilized peptides to a first heated fluid stream comprising first activated amino acids such that a first amino acid residue is added to at least about 99% of the immobilized peptides, wherein the first activated amino acids are activated prior to and within 30 seconds of exposing the immobilized peptide to the first heated fluid stream and a pressure drop across the solid support does not exceed about 700 psi for more than about 5% of the time period during which the first amino acid addition cycle is performed; and
   performing a second amino acid addition cycle comprising exposing the immobilized peptides to a second heated fluid stream comprising second activated amino acids such that a second amino acid residue is added to at least about 99% of the immobilized peptides, wherein the second activated amino acids are activated prior to and within 30 seconds of exposing the immobilized peptide to the second heated fluid stream and a pressure drop across the solid support does not exceed about 700 psi for more than about 5% of the time period during which the second amino acid addition cycle is performed;
   wherein:
      the total amount of time between the ends of the first and second amino acid addition cycles is about 10 minutes or less and the protection groups comprise fluorenylmethyloxycarbonyl protection groups and/or
      the total amount of time between the ends of the first and second amino acid addition cycles is about 5 minutes or less.

2. A process for adding amino acid residues to peptides, comprising:
   providing a plurality of peptides comprising protection groups, each peptide immobilized on a solid support;
   exposing a deprotection reagent to the immobilized peptides to remove protection groups from at least a portion of the immobilized peptides;
   removing at least a portion of the deprotection reagent;
   exposing the immobilized peptides to a heated fluid stream comprising activated amino acids such that at least a portion of the activated amino acids are bonded to the immobilized peptides to form newly-bonded amino acid residues, wherein the activated amino acids are activated prior to and within 30 seconds of the exposing step, and wherein, during the exposing step, a pressure drop across the solid support does not exceed about 700 psi for more than about 5% of the time period during which the exposing step is performed; and
   removing at least a portion of activated amino acids that do not bond to the immobilized peptides;
   wherein an amino acid residue is added to at least about 99% of the immobilized peptides during the amino acids exposing step; and
   wherein:
      the total amount of time taken to perform the combination of all of the deprotection reagent exposing step, the deprotection reagent removal step, the activated amino acid exposing step, and the activated amino acid removal step is about 10 minutes or less and the protection groups comprise fluorenylmethyloxycarbonyl protection groups and/or
      the total amount of time taken to perform the combination of all of the deprotection reagent exposing step, the deprotection reagent removal step, the activated amino acid exposing step, and the activated amino acid removal step is about 5 minutes or less.

3. A process for adding amino acid residues to peptides, comprising:
   providing a plurality of peptides immobilized on a solid support; and
   exposing the immobilized peptides to a heated fluid stream comprising activated amino acids such that at least a portion of the activated amino acids are bonded to the immobilized peptides to form newly-bonded amino acid residues,
   wherein the activated amino acids are activated prior to and within 30 seconds of the exposing step,
   wherein, during the exposing step, a pressure drop across the solid support does not exceed about 700 psi for more than about 5% of the time period during which the exposing step is performed; and
   wherein an amino acid residue is added to at least about 99% of the immobilized peptides within about 1 minute or less.

4. The process of claim 3, wherein an amino acid residue is added to at least about 99.9% of the immobilized peptides within about 1 minute or less.

5. The process of claim 3, wherein an amino acid residue is added to at least about 99% of the immobilized peptides within about 30 seconds or less.

6. The process of claim 3, wherein the solid support is contained within a packed column and/or a fluidized bed.

7. The process of claim 3, wherein the solid support comprises polystyrene and/or polyethylene glycol.

8. The process of claim 3, wherein the solid support comprises a resin.

9. The process of claim 8, wherein the solid support comprises a microporous polystyrene resin.

10. The process of claim 3, wherein multiple copies of the amino acid residue are bonded to fewer than about 1% of the immobilized peptides during the exposing step.

11. The process of claim 3, wherein adding an amino acid residue to the immobilized peptides comprises adding a single amino acid residue to the immobilized peptides.

12. The process of claim 3, wherein adding an amino acid residue to the immobilized peptides comprises adding a peptide comprising two or more amino acid residues to the immobilized peptides.

13. The process of claim 3, wherein the heated fluid stream has a temperature that is at least about 10° C. greater than room temperature.

* * * * *